(12) United States Patent
Fist et al.

(10) Patent No.: US 10,791,691 B2
(45) Date of Patent: *Oct. 6, 2020

(54) PAPAVER SOMNIFERUM WITH HIGH CONCENTRATION OF CODEINE

(71) Applicant: Tasmanian Alkaloids Pty. Ltd., Westbury, Tasmania (AU)

(72) Inventors: Anthony J. Fist, Norwood (AU); James A. C. Miller, Craters (AU); Davina Gregory, Tasmania (AU)

(73) Assignee: Tasmanian Alkaloids Pty. Ltd., Westbury (AU)

( * ) Notice: Subject to any disclaimer, the term of this patent is extended or adjusted under 35 U.S.C. 154(b) by 281 days.

This patent is subject to a terminal disclaimer.

(21) Appl. No.: 15/493,988

(22) Filed: Apr. 21, 2017

(65) Prior Publication Data
US 2017/0280647 A1    Oct. 5, 2017

Related U.S. Application Data

(60) Continuation of application No. 13/833,999, filed on Mar. 15, 2013, now Pat. No. 9,648,815, which is a division of application No. 12/470,604, filed on May 22, 2009, now Pat. No. 9,541,647.

(60) Provisional application No. 61/160,749, filed on Mar. 17, 2009, provisional application No. 61/160,532, filed on Mar. 16, 2009, provisional application No. 61/056,880, filed on May 29, 2008.

(51) Int. Cl.
| | | |
|---|---|---|
| *A01H 5/02* | (2018.01) | |
| *A01H 5/04* | (2018.01) | |
| *C07D 489/02* | (2006.01) | |
| *A01H 4/00* | (2006.01) | |

(52) U.S. Cl.
CPC ............ *A01H 5/02* (2013.01); *A01H 4/001* (2013.01); *A01H 5/04* (2013.01); *C07D 489/02* (2013.01)

(58) Field of Classification Search
CPC .................................................... A01H 5/02
See application file for complete search history.

(56) References Cited

U.S. PATENT DOCUMENTS

| | | | |
|---|---|---|---|
| 3,812,132 A | 5/1974 | Grew et al. | |
| 4,613,668 A | 9/1986 | Rice | |
| 4,795,813 A | 1/1989 | Schwartz | |
| 6,067,749 A | 5/2000 | Fist et al. | |
| 6,376,221 B1 | 4/2002 | Fist et al. | |
| 6,570,063 B1 | 5/2003 | Butler | |
| 6,723,894 B2 | 4/2004 | Fist et al. | |
| 8,541,647 B2 | 9/2013 | Fist et al. | |
| 9,648,815 B2 * | 5/2017 | Fist | A01H 5/02 |
| 2002/0083491 A1 | 6/2002 | Peele | |
| 2004/0197428 A1 | 10/2004 | Fist et al. | |

FOREIGN PATENT DOCUMENTS

| | | |
|---|---|---|
| AU | 646074 | 3/1992 |
| AU | 200148054 A1 | 8/2001 |
| AU | 2005201353 B2 | 4/2005 |
| AU | 2003204625 | 12/2006 |
| AU | 2009253741 A1 | 10/2017 |
| DE | 112648 C | 4/1975 |
| EP | 1525789 | 4/2005 |
| HU | 216772 A | 12/1995 |
| HU | 216771 | 12/1999 |
| WO | 9802033 A1 | 1/1998 |
| WO | 9911765 A1 | 3/1999 |
| WO | 9935902 A1 | 7/1999 |
| WO | 0058333 A1 | 10/2000 |
| WO | 2005107436 | 11/2005 |
| WO | 2007022561 | 3/2007 |
| WO | 2009092134 | 7/2009 |
| WO | 2009109012 A1 | 9/2009 |
| WO | 2009143574 A1 | 12/2009 |

OTHER PUBLICATIONS

Tookey, H.L. et al. Planta Medica; vol. 30, 1976; pp. 340-348.*
Prajapati, S. et al. Genetic Resources and Crop Evolution (2002), vol. 49, No. 2; pp. 1-6.*
Ziegler, J. and Facchini, P. J.; Annual Rev. of Plant Biol. (2008) vol. 59, pp. 735-769.*
Oluk, E. A., Plant Tissue Cult. & Biotech., (Jun. 2006) vol. 16, No. 1; pp. 1-4.*
Le Flem-Bonhomme,V., Planta, 2004; vol. 218: pp. 890-893.*
In Tookey, H.L. et al., Plant Medica; vol. 30, 1976; pp. 340-348. (Year: 1976).*
Yoshimatsu Kayo et al "Transformation of opium poppy (*Papaver somniferum* L.) with *Agrobacterium rhizogenes* MAFF 03-01724" Plant Cell Rep 11:132-136 (1992).
Ziegler Jorg et al "Alkaloid Biosynthesis: Metabolism and Trafficking" Annu Rev Plant Biol 59:735-769 (2008).
Millgate Anthony G "A genomic study of morphinan biosynthesis in the 'opium poppy' *Papaver somniferum* L." a Thesis, School of Biochemistry and Molecular Biology, Faculty of Science, Australian National University, Acton, ACT 2601, Australia, 295 pgs (Dec. 2004).
"Codeine Poppy Takes Off in Tasmania" ABC Rural News (http://www.abc.net.au/site-archive/rural/news/content/200904/s2556882.htm), 2 pages (Apr. 30, 2009).
Allen Robert S et al "RNAi-mediated replacement of morphine with the nonnarcotic alkaloid reticuline in opium poppy" Nat Biotechnol 22(12):1559-1566 (Dec. 2004).
Allen Robert S et al "Metabolic engineering of morphinan alkaloids by over-expression and RNAi suppression of salutaridinol 7-O-acetyltransferase in opium poppy" Plant Biotechnol J 6:22-30 (2008).
Australian Patent Application No. 2009253741 Patent Examination Report No. 1, dated Feb. 12, 2014 (3 pp).

(Continued)

*Primary Examiner* — Russell Kallis
(74) *Attorney, Agent, or Firm* — Fitch Even Tabin & Flannery LLP

(57) ABSTRACT

A poppy straw of *Papaver somniferum*, wherein the poppy straw includes codeine constituting about 40% by weight or greater of an alkaloid combination.

34 Claims, 4 Drawing Sheets

(56) References Cited

OTHER PUBLICATIONS

Australian Patent Application No. 2009253741 Statement of Grounds and Particulars, dated Dec. 7, 2015 (7 pp).
Australian Patent Application No. 2009253741 Statement of Grounds and Particulars, dated Dec. 11, 2015 (22 pp).
Bernath Jeno et al "The Effect of Environmental Factors on Growth. Development and Alkaloid Production of Poppy (*Papaver somniferum* L.) I. Responses to Day-length and Light Intensity" Biochem Physiol Pflanzen 174:468-478 (1979).
Brochmann-Hanssen E "A Second Pathway for the Terminal Steps in the Biosynthesis of Morphine" Planta Medica pp. 343-345 (1984).
Catchpole Heather "Meet Norman, the no-morphine poppy" News in Science (ABC Science) (http://www.abc.net.au/science/articles/2004/09/23/1203133.htm), 2 pp (Sep. 23, 2004).
Chauhan SP et al "Mutagenic Effects of Combined and Single Doses of Gamma Rays and EMS in Opium Poppy" Plant Breeding 110(4):342-345 (1993).
Chitty Julie A et al "Genetic transformation in commercial Tasmanian cultivars of opium poppy, *Papaver somniferum*, and movement of transgenicpollen in the field" Funct Plant Biol 30:1045-1058 (2003).
Chitty Julie A et al "Opium Poppy (*Papaver somniferum*)" Methods Mol Biol 344(2):383-391.
European Patent Application No. 09753338.4 Extended European Search Report, dated Sep. 9, 2011 (6 pp).
Facchini Peter J et al "Opium poppy: a model system to investigate alkaloid biosynthesis in plants" Can J Bot 83 (10):1189-1206 (2005).
Facchini Peter J et al "Synthesis and trafficking of alkaloid biosynthetic ezymes" Curr Opin Plant Biol 8:657-666 (2005).
Facchini Peter J "Regulation of Alkaloid Biosynthesis in Plants" The Alkaloids: Chemistry and Biology, Ch 1 63:1-44 (2006).
Facchini Peter J et al "Opium poppy: blueprint for an alkaloid factory" Phytochem Rev 6(1):97-124 (2007).
Filippetti A et al "Improvement of Seed Yield in *Vicia faba* L. By Using Experimental Mutagenesis. II. Comparison of Gamma-Radiation and Ethyl-Methane-Sulphonate (EMS) in Production of Morphological Mutants" Euphytica 35:49-59 (1986).
Fist AJ "The Tasmanian Poppy Industry: A Case Study of the Application of Science and Technology" Tasmanian Alkaloids Pty Ltd, 10 pp (2001).
Fist A et al "Identification of seven new mutant poppy lines" Agricultural R&D Report, 11 pgs (Mar. 23, 2004).
Ghiorghita et al "Gamma Irradiation Ethylmethanesulfonate and Diethylsulfate Treatments Induced Changes in Morphine Content and other Biochemical Parameters in *Papaver somniferum* L.", Revue Roumaine De Biologie Serie De Biologie Vegetale, Editura Academiei Romane, Bucharest 27(2):121-126 (Jan. 1982).
Gumuscu Ahmet et al "Evaluation of selected poppy (*Papaver somniferum* L.) lines by their morphine and other alkaloids contents" Eur Food Res Technol 226:1213-1220 (2008).
Hagel JM et al "II.2 Opium Poppy" Transgenic Crops VI, Biotechnology in Agriculture and Forestry 61:169-187 (2007).
Henikoff Steven et al "TILLING. Traditional Mutagenesis Meets Functional Genomics" Plant Physiol 135:630-636 (Jun. 2004).
Report of International Narcotics Control Board for 2006 "Narcotic Drugs. Estimated World Requirements for 2007. Statistics for 2005".
Report of International Narcotics Control Board for 2014 "Narcotic Drugs. Estimated World Requirements for 2015. Statistics for 2013".
Khanna KR et al "HPLC Investigation of the Inheritance of Major Opium Alkaloids" Planta Medica pp. 157-158 (1986).
Kodym Andrea et al "Physical and Chemical Mutagenesis" Ch 12 Methods Moi Biol 236:189-203 (2003).
Koorneef M et al "EMS- and radiation-induced mutation frequencies at individual loci in *Arabidopsis thaliana* (L.) Heynh." Ch 5 Mutation Res 93:109-123 (1982).

Larkin Philip J et al "Increasing morphinan alkaloid production by over-expressing codeinone reductase in transgenic *Papaver somniferum*" Plant Biotechnol J 5(1):26-37 (2007).
Leary Sarah "New strain of poppy could transform industry" Burnie Advocate p. 5 (Mar. 20, 2009).
Levy A "Natural and Induced Genetic Variation in the Biosynthesis of Alkaloids and Other Secondary Metabolites in the Biosynthesis of Alkaloids and Other Secondary Metabolites" Institute of Field and Garden Crops pp. 213-222 (1980).
Levy Arieh et al "Genetics and Breeding of *Papaver somniferum*" Ch 4 Poppy, the Genus Papaver, Harwood Academic Publishers, Edited by Jeno Bernath pp. 93-103 (1998).
Li Xin et al "A fast neutron deletion mutagenesis-based reverse genetics system for plants" The Plant J 27(3):235-242 (2001).
Liscombe David K et al "Evolutionary and cellular webs in benzylisoquinoline alkaloid biosynthesis" Curr Opin Biotechnol 19:173-180 (2008).
Memelink Johan "Putting the opium in poppy to sleep" Nat Biotechnol 22(12):1526-1527 (Dec. 2004).
Millgate Anthony G et al "Morphine-pathway block in top 1 poppies" Nat 431:413-414 (Sep. 23, 2004).
Nelsen B et al "Oripavine—A New Opium Alkaloid" Planta Medica 48:205-206 (1983).
Nyman Ulf et al "Some varieties of *Papaver somniferum* L. with changed morphinane alkaloid content" Hereditas 84:69-76 (1976).
Nyman Ulf "Selection for high thebaine/low morphine content in *Papaver somniferum* L. II. Studies of the I4 and I5 generations from a spontaneous mutant" Hereditas 93:121-124 (1980).
Parker Harriet I et al "Biosynthetic Conversion of Thebaine to Codeine" J Am Chem Soc 94(4):1276-1282 (Feb. 23, 1972).
Prajapati Seema et al "Alkaloid profiles of the Indian land races of the opium poppy *Papaver somniferum* L." Genetic Research and Crop Evolution 00:1-2 (2002).
Roberts Margaret F "Production of Alkaloids in Plant Cell Culture" Alkaloids. Biochemistry, Ecology, and Medicinal Applications, Plenum Press, Ch 7 pp. 159-197 (1998).
Staba EJ et al "Alkaloid Production from Papaver Tissue Cultures" J Nat Prod 45(3):256-262 (1982).
"New poppy strain revolutionises" Burnie Advocate p. 31 (Mar. 26, 2009).
"Poppies: no bed of roses" The Furrow, Australian and New Zealand Edition p. 30 (2006).
Tookey HL et al "Codeine and Morphine in Papaver Somniferum Grown in a Controlled Environment" Planta Medica 30(4):340-348 (Dec. 1976).
Williams Rachel "Codeine poppy crop grown for first time" Launceston Examiner p. 21 (Mar. 20, 2009).
Winzer Thilo et al "Morphinan biosynthesis in opium poppy requires a P450-oxidoreductase fusion protein" Sci 349 (6245):309-312 (Jul. 17, 2015).
International Patent Application No. PCT/AU2009/000666 International Search Report, dated Jul. 17, 2009, 3 pgs.
Apuya, Nestor, R., et al., "Enhancement of alkaloid production in opium and California poppy by transactivation using heterologous regulatory factors." Plant Biotechnology Journal, 2008, vol. 6, pp. 160-175.
Brezinová, Beáta, et al., "The Morphological Diversity of Selected Traits of World Collection of Poppy Genotypes (*Genus papaver*)." Journal of Central European Agriculture, vol. 10, 2009, No. 2, pp. 183-190.
Dittbrenner, A., et al., "Variability of Alkaloid Content in *Papaver somniferum* L.", Journal of Applied Botany and Food Quality, vol. 82, 2009, pp. 103-107.
Dubey, Mukesh K., et al., "Genetic Variation Revealed in the Chloroplast-Encoded RNA Polymerase Beta' Subunit of Downy Mildew-Resistant Genotype of Opium Poppy." Journal of Heredity, 2009, vol. 100, No. 1, pp. 76-85.
English translation dated Apr. 9, 2001 of Jonsson B. and Jönsson R, Sveriges Utsädesförenings Tidskrift, 96, 1986, pp. 243-249.
European Patent Application No. EP 09718439.4. Extended European Search Report dated Feb. 24, 2011 including the European Supplementary Search Report dated Feb. 17, 2011 and European Search Opinion for EP 09718439.4, 6 pages.

(56) References Cited

OTHER PUBLICATIONS

Facchini, Peter J., et al., "Differential and Tissue-specific Expression of a Gene Family for Tyrosine/Dopa Decarboxylase in Opium Poppy." Journal of Biological Chemistry, 1994, vol. 269, No. 43, Issue of Oct. 28, pp. 26684-26690.
Facchini, Peter J., et al., "Molecular Characterization of Berberine Bridge Enzyme Genes from Opium Poppy." Plant Physiol., 1996, vol. 112, pp. 1669-1677.
Indian Application 5030/KOLNP/2010, Decision, dated Feb. 21, 2019, 48 pages.
Indian Application 5030/KOLNP/2010, Examination Report, dated Jul. 24, 2017, 7 pages.
Indian Application 5030/KOLNP/2010, Hearing Notice, dated Jun. 20, 2018, 4 pages.
International Patent Application No. PCT/AU2009/000270, International Search Report, dated Apr. 14, 2009, 4 pages.
International Patent Application No. PCT/AU2009/000270, Written Opinion, dated Apr. 14, 2009, 4 pages.
International Patent Application No. PCT/AU2009/00666, Written Opinion, dated Jul. 17, 2009, 5 pages.
Intodia, S.K., et al., "Effect of Sulphur Fertilization on Growth of Opium Poppy in Calcareous Soils of South Rajasthan." Indian J. Plant Physiol., 2005, vol. 10, No. 1, pp. 90-93.
Li, Xin, et al., "Deleteagene: A Fast Neutron Deletion Mutagenesis-Based Gene Knockout System for Plants." Comparative and Functional Genomics, 2002, vol. 3, pp. 158-160.
Liscombe, David K., et al., 'Erratum to "Evidence for the monophyletic evolution of benzylisoquinoline alkaloid biosynthesis in angiosperms."' Phytochemistry, vol. 66, 2005, pp. 2500-2520.
Nemeth, E., et al., "New Results of Poppy (*Papaver somniferum* L.) Breeding for Low Alkaloid Content in Hungary." Acta Hort., 2002, vol. 576, pp. 151-158.
Pauli, Hubert H., et al., "Molecular Cloning and Functional Heterologous Expression of Two Alleles Encoding (S)-N-methylcoclaurine 3'-hydroxylase (CYP80B1), a New Methyl Jasmonate-Inducible Cytochrome P-450-dependent Mono-oxygenase of Benzylisoquinoline Alkaloid Biosynthesis." The Plant Journal, 1998, vol. 13, No. 6, pp. 793-801.
Seddigh, Majid, et al., "*Papaver bracteatum*, Potential Commercial Source of Codeine," Economic Botany, 36, 1982, pp. 433-441.
Singh, H.P., et al., "Inheritance of Light Yellow Leaf Colour in Opium Poppy (*Papaver somniferum* L.)." Indian J. Genet., 2002, vol. 62, No. 2, pp. 181-182.
Unterlinner, Bernhard, et al., "Molecular Cloning and Functional Expression of Codeinone Reductase: the Penultimate Enzyme in Morphine Biosyntheses in the Opium Poppy Papaver Somniferum." The Plant Journal, 1999, 18(5), pp. 465-475.
Zenk, Meinhart H., et al., "Evolution and Current Status of the Phytochemistry of Nitrogenous Compounds." Phytochemistry, vol. 68, 2007, pp. 2757-2772.

\* cited by examiner

PAPAVER SOMNIFERUM WITH HIGH CONCENTRATION OF CODEINE

CROSS-REFERENCE TO RELATED APPLICATIONS

This is a continuation application of U.S. application Ser. No. 13/833,999 filed Mar. 15, 2013, which is a divisional application of U.S. application Ser. No. 12/470,604 filed May 22, 2009, which claims the benefit of U.S. Provisional Application No. 61/056,880 filed May 29, 2008; U.S. Provisional Application No. 61/160,532 filed Mar. 16, 2009; and U.S. Provisional Application No. 61/160,749 filed Mar. 17, 2009, the contents of each of which are hereby incorporated by reference in their entirety.

FIELD OF THE INVENTION

The present invention is directed to the improved production of codeine. More particularly, the present invention relates to the use of an improved *Papaver somniferum* poppy plant to produce codeine in higher yield, allowing codeine to be produced without the need to grow poppies containing morphine.

BACKGROUND OF THE INVENTION

Codeine is an opiate used for its analgesic, antitussive and antidiarrheal properties. It is by far the most widely used opiate in the world and very likely the most commonly used drug overall according to numerous reports over the years by organizations such as the World Health Organization.

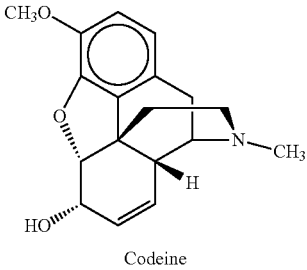

Codeine

Codeine is a natural alkaloid of the opium poppy plant *Papaver somniferum* L. but normally constitutes only a minor fraction of the total alkaloids e.g. typically only 5-20% of the level of morphine. While codeine can be extracted from opium and poppy straw, the demand for codeine far exceeds the current available natural supply so most of the codeine currently being manufactured (85-90 percent) is obtained from morphine through the process of O-methylation. The major part of the world's licit morphine production is to support the manufacture of codeine. If codeine could be sourced from non-morphine-containing poppies it would greatly decrease the growing of morphine poppies with the potential for diversion and abuse. Codeine is used to manufacture Active Pharmaceutical Ingredients (APIs) such as Codeine Phosphate, Codeine Sulphate, Codeine Hydrochloride and Codeine Base, which are in turn used to manufacture e.g. high-volume, over-the-counter, dosage forms for the relief of pain (analgesics) and cough (antitussives). Codeine is also the starting material and prototype of a large class of mainly mild to moderately strong opioids such as dihydrocodeine and hydrocodone and its derivatives such as nicocodeine and oxycodone. Thus catalytic hydrogenation of codeine yields dihydrocodeine (used to manufacture APIs such as Dihydrocodeine Tartrate) that in turn can be converted by Oppenauer oxidation to dihydrocodeinone (Hydrocodone, used to manufacture APIs such as Hydrocodone Bitartrate).

The industrial-scale methylation of morphine, at the phenolic hydroxyl group at position 3, to give codeine is usually conducted using quaternary ammonium methylating agents, typically trimethylphenylammonium chloride, in the presence of various bases such as alkali hydroxides, alkoxides, or carbonates/bicarbonates. Use of the quaternary ammonium methylating agent greatly diminishes the competing methylation of the alkaloid tertiary amine function which is a major problem with other methylating agents such as methyl halides or dimethyl sulphate, where the formation of the alkaloid quaternary salts causes loss of yield and the generation of other impurities such as alpha- and beta-codimethine via the Hofmann elimination reaction. However this solution to the quaternisation problem comes at the cost of generating the objectionally-odiferous and toxic byproduct N,N-dimethylaniline (DMA); this must be completely removed from the product and imposes waste disposal, occupational health and safety (OHS) and environmental concerns.

Most methylation procedures using trimethylphenylammonium reagents in essence involve the exposure of the trimethylammonium morphinate ion pair to high temperatures (exceeding 90 deg C.) in a non-polar, water-immiscible solvent such as toluene or xylene, where the ion pair rapidly collapses to codeine and DMA. The necessity for such solvents creates further OHS and environmental burdens on the manufacture and imposes costs associated with solvent recovery and purification. Under the vigorous conditions necessary, it is imperative that the stoichiometry of the reagents be carefully controlled to avoid on the one hand, undermethylation, leaving too much unreacted morphine, or on the other hand overmethylation, leading to formation of codeine-O(6)-methyl ether ("methylcodeine"). Both situations lead to yield losses both directly, through lower codeine formation, and indirectly through further codeine losses attending the removal of the unreacted morphine or the methycodeine impurities; morphine is relatively easy to remove e.g. by washing a toluene solution of the codeine with aqueous alkali but this process also sacrifices some codeine to the washes, while methylcodeine is difficult to remove and may require extensive processing to achieve desired limits. Another problematic impurity created by the synthesis from morphine is dimethylpseudomorphine, created by methylation of a common impurity in Concentrate of Poppy Straw Morphine, pseudomorphine (2,2'-bismorphine). Dimethylpseudomorphine is particularly difficult to remove from codeine and imposes high yield losses due to the additional processing required.

The manufacture of codeine from morphine requires extensive processing at some stage to remove colour bodies originating either in opium or in the Concentrate of Poppy Straw Morphine (CPS-M); in the latter case the colour bodies derive from the initial extraction process that produces morphine from poppy straw; the extraction conditions required to recover morphine from poppy straw are such that there is considerable, unavoidable extraction of coloured materials from the poppy and the CPS-M may typically have several percent of non-alkaloid material. With opium as input, the raw material is grossly impure (e.g. 5-24% morphine) and it is mandatory to purify and separate the morphine from the other alkaloids and colour bodies before input to codeine manufacture, while with Concentrate of Poppy Straw Morphine, some manufacturers upgrade the morphine to Technical quality before manufacture of codeine, while others enter the material directly into the methylation and then process to remove colour post-methylation; both approaches have considerable cost penalties associated with the additional processing, inevitable yield losses, capacity and opportunity costs. Codeine is more soluble than morphine in virtually all common media and is consequently easier to extract from poppies and easier to purify; hence the yield and quality and cost of natural codeine obtained from a codeine poppy are all improved relative to synthetic codeine obtained from natural morphine.

Alkaloids are extracted from the poppy capsules of *Papaver somniferum* by two commercial methods. In one method, the immature capsule is cut and the latex collected from the wound. The air-dried latex is opium which, according to the Merck Index, 11th edition, contains alkaloids in the amounts shown in Table I. In a second method, the mature poppy capsules and the poppy capsule stems are collected, and threshed to remove the seeds and form a straw. When necessary, the straw is dried to a water content below 16%. Solvent or water extraction is employed to remove the alkaloids from the straw. For the varieties of *Papaver somniferum* normally grown, the straw, on a dry basis, contains alkaloids in the amounts shown in Table 1.

TABLE 1

|  | opium | straw |
| --- | --- | --- |
| morphine, % | 10-16 | 1-3 |
| codeine, % | 0.8-2.5 | 0.05-0.3 |
| oripavine, % | 0-0.1 | 0-0.05 |
| thebaine, % | 0.5-2 | 0.15-0.65 |

As can be seen, the yield of codeine is confounded with that of other alkaloids. A poppy producing predominantly codeine, e.g., as 55% or more of the total alkaloids, would enable a simpler extraction/purification process, resulting in higher yields, better quality and throughput and lower costs.

Where solvent or water or super critical fluid, such as $CO_2$, extraction is employed to remove the alkaloids from the straw, such method, as practiced, involves the production of "Concentrate of Poppy Straw". Concentrate of Poppy Straw (or "CPS") is described as "The material arising when poppy straw has entered into a process for the concentration of its alkaloids, when such material is made available in trade," (Multilingual dictionary of narcotic drugs and psychotropic substances under international control, United Nations, New York, 1983). Not inconsistent with the foregoing description, Concentrate of Poppy Straw is described as "the crude extract of poppy straw in either liquid, solid or powder form which contains the phenanthrene alkaloids of the opium poppy," 45 U.S. Federal Register 77466, Nov. 24, 1980. When in liquid form, the liquid is preferably concentrated before entering into commerce. The generally preferred Concentrate of Poppy Straw is the powder form which results from removing the solvent or water following extraction of the poppy straw. According to the United Nations publication '*Narcotic Drugs: Estimated World Requirements for* 2007; *Statistics for* 2005 (E/INCB/2006/2)', "Concentrate of Poppy Straw is the dried residue obtained through the extraction of alkaloids from poppy straw. Until the second half of the 1990s, only concentrate of poppy straw containing morphine as the main alkaloid was manufactured. Since then, concentrate of poppy straw containing mainly thebaine or oripavine has started to be manufactured."

Some relatively small quantities of CPS codeine are produced in a few countries as a by-product of CPS morphine extraction. These quantities are not significant in world trade. The claimed invention now provides codeine CPS which has great commercial potential because it allows production of codeine CPS and derivatives without the need to grow poppies containing morphine.

SUMMARY OF THE INVENTION

The present invention is directed to a *Papaver somniferum* plant, which upon the harvesting of its poppy capsules will yield a poppy straw having codeine constituting about 40% (preferably about 50%, more preferably about 75%, still more preferably about 90%, and most preferably, about 96%) by weight or greater of an alkaloid combination, or alternatively, which upon the collection and drying of the latex from its immature poppy capsules will yield an opium having codeine constituting about 40% (preferably about 55%, more preferably about 75%, still more preferably about 90%, and most preferably, about 96%) by weight or greater of the alkaloid combination, wherein the alkaloid combination comprises morphine, codeine, thebaine and oripavine. Preferably, the codeine content is above 0.8% (preferably, above 2.0%, more preferably, above 2.5%, still more preferably, above 3.0%, and most preferably, above 3.5%) in the poppy straw on a dry weight basis. In another embodiment, the codeine content is between 0.8% to about 4.2% (preferably, between about 2.5% and about 4.2%, more preferably, between about 3.0% and 4.2%, most preferably, between 3.5% and 4.2%) on a dry weight basis. In an embodiment of the present invention, the poppy straw and opium of the *Papaver somniferum* plant will have thebaine constituting about 40% (preferably about 25%, more preferably about 10%, and most preferably about 2%) by weight or less of the alkaloid combination. One of ordinary skill in the art will understand that the total alkaloid content in the poppy straw or opium in any of the embodiments of the present invention will total (but will not exceed) 100%. In a preferred embodiment, there is substantially no morphine, thebaine or oripavine in the alkaloid combination. In another embodiment of the present invention, the alkaloid combination further comprises salutaridine, reticuline, laudanine, papaverine and noscapine. In still another embodiment, the plant is stably reproducing.

In another embodiment of the invention is a plant of *Papaver somniferum*, which upon the harvesting of its poppy capsules will yield a poppy straw having codeine content of about 0.8% to about 4.2% (preferably, between about 2.5% and about 4.2%, more preferably, between about 3.0% and 4.2%, most preferably, between 3.5% and 4.2%) on a dry weight basis. Preferably, the morphine content in the plant is about 0.05% of the straw weight or less on a dry weight basis. Alternatively, the plant is a plant of *Papaver somniferum* which upon the collection and drying of the latex from their immature poppy capsules will yield an opium having codeine constituting about 10% by weight or greater. Preferably, the *Papaver somniferum* plants are stably reproducing.

In another embodiment of the invention is a plant of *Papaver somniferum*, which upon the harvesting of its poppy capsules will yield a poppy straw wherein the ratio of codeine and thebaine to an alkaloid combination comprising morphine, codeine, thebaine and oripavine is between about 0.90 and about 1.00 (preferably between about 0.98 and about 1.00, more preferably between about 0.99 and about 1.00). In additional aspects of the invention, the alkaloid combination may further comprise salutaridine, reticuline, laudanine, papaverine and noscapine, and the *Papaver somniferum* plants are stably reproducing.

In still another embodiment of the invention is a plant comprising a plant of *Papaver somniferum*, which upon the harvesting of its poppy capsules will yield a poppy straw wherein the ratio of codeine to an alkaloid combination comprising morphine, codeine, thebaine and oripavine is about 0.40 or greater. Preferably, the ratio is between about 0.65 and about 0.97, more preferably, between about 0.75 and about 0.97. In additional aspects of the invention, the alkaloid combination may further comprise salutaridine, reticuline, laudanine, papaverine and noscapine, and the *Papaver somniferum* plants are stably reproducing.

The invention is also directed to a stand of any of the poppy plants described above.

Also included in the invention is seed of any of the poppy plants described above. In one particular embodiment, the seed is a *Papaver somniferum* seed which is ATCC PTA-9294.

The invention also provides a poppy straw, concentrate of poppy straw and opium of any of the *Papaver somniferum* plants described above.

In another embodiment of the invention is a method for the production of codeine which comprises the steps of: a) harvesting poppy capsules of any of the *Papaver somniferum* plants described above to produce a poppy straw; and b) extracting the codeine from the poppy straw.

In still another embodiment is a method for the production of codeine which comprises the steps of: a) collecting and drying the latex of the immature poppy capsules of any of the *Papaver somniferum* plants described above to produce opium e; and b) extracting the codeine from the opium.

The invention also includes a poppy straw of *Papaver somniferum* having codeine constituting between about 0.8% and about 4.2% (preferably, between about 2.0% and about 4.2%, more preferably, between about 2.5% and about 4.19%) of the alkaloid content of the poppy straw, on a dry weight basis.

Another embodiment of the invention is a poppy straw of *Papaver somniferum* wherein the ratio of codeine to an alkaloid combination comprising morphine, codeine, thebaine and oripavine is between about 0.40 and about 1.00 (preferably, between about 0.65 and about 0.97, more preferably, between about 0.75 and about 0.97), on a dry weight basis. Preferably, the alkaloid combination further comprises salutaridine, reticuline, laudanine, papaverine and noscapine.

The invention is also directed to a poppy straw comprising a poppy straw of *Papaver somniferum* wherein the ratio of codeine to an alkaloid combination comprising morphine, codeine, thebaine and oripavine is greater than 0.4, and the ratio of codeine and thebaine to an alkaloid combination comprising morphine, codeine, thebaine and oripavine is between about 0.90 and about 1.00 (preferably, between about 0.98 and about 1.00, more preferably, between about 0.99 and about 1.00). Preferably, the alkaloid combination further comprises salutaridine, reticuline, laudanine, papaverine and noscapine.

There is also provided by the present invention a method to improve the codeine yield of a stably reproducing *Papaver somniferum*, the method comprising the steps of:
a) exposing at least one poppy seed of *Papaver somniferum* to a mutagenizing agent, b) growing at least one mutagenized poppy seed to produce a plant bearing a leaf or an immature poppy capsule, optionally through multiple self-fertilized generations, c) sampling the leaf or poppy capsule (or any other latex-containing tissue) of the plant(s) grown in b) for the presence of thebaine, oripavine, morphine and codeine, d) repeating steps a) to c) until a poppy plant of *Papaver somniferum* is obtained having codeine constituting about 40% (preferably, about 55%) by weight or greater, and having thebaine constituting about 40% by weight or less, of the alkaloid combination, wherein the alkaloid combination comprises morphine, codeine, thebaine and oripavine; and e) collecting the seed from the plant obtained in "d" and growing another generation of plants to ensure that the subsequent generation stably re-produces the high codeine and low morphine characteristic.

The present invention also provides a method to improve the codeine yield of a stably reproducing *Papaver somniferum*, the method comprising the steps of:
a) exposing at least one poppy seed of *Papaver somniferum* containing the Norman mutation (at least one poppy seed of a Norman poppy) to a mutagenizing agent, b) growing at least one mutagenized poppy seed to produce a plant bearing a leaf or an immature poppy capsule, optionally through multiple self-fertilized generations, c) sampling the leaf or poppy capsule (or any other latex-containing tissue) of the plant(s) grown in b) for the presence of thebaine, oripavine, morphine and codeine, d) repeating steps a) to c) until a poppy plant of *Papaver somniferum* is obtained having thebaine as the predominant alkaloid, and substantially no oripavine in the alkaloid combination, wherein the alkaloid combination comprises morphine, codeine, thebaine and oripavine;

e) collecting the seed from the plant obtained in "d" and optionally grow another generation of plants to ensure that the subsequent generation stably re-produces the high thebaine and low oripavine characteristic;

f) cross pollinating the plant obtained in "d" (or a similar plant obtained in subsequent generations) with a *Papaver somniferum* plant containing morphine;

g) growing an F1 generation, allowing the buds to self pollinate, and collecting the seed produced;

h) growing the F2 seed and sampling the leaf or poppy capsule (or any other latex-containing tissue) for the presence of thebaine, oripavine, morphine and codeine, i) identifying poppy plants having codeine constituting about 40% (preferably, about 55%) by weight or greater, and having thebaine constituting about 40% by weight or less, of the alkaloid combination, wherein the alkaloid combination comprises morphine, codeine, thebaine and oripavine, and having substantially no morphine; and j) collecting the seed from the plant obtained in "i" and growing another generation of plants to ensure that the subsequent generation stably re-produces the high codeine (codeine constituting about 40%, preferably about 55%, by weight or greater of the alkaloid combination) and low thebaine (thebaine constituting about 40% by weight or less of the alkaloid combination) and morphine (substantially no morphine) characteristic.

The present invention also provides a plant of *Papaver somniferum*, preferably a stably reproducing plant of *Papaver somniferum*, which upon the harvesting of their poppy capsules will yield a poppy straw having codeine content of about 0.81% to about 4.19%, and having morphine constituting about 0.05% of the straw weight or less each on a dry weight basis, or alternatively, which upon the collection and drying of the latex from their immature poppy capsules will yield an opium having codeine constituting about 10% by weight or greater. The present invention provides poppy straw which in addition to the codeine contents presented above, contain thebaine constituting from about 0.02% of the poppy straw to about 2.24% of the poppy straw on a dry weight basis.

The invention is also directed to progeny of *Papaver somniferum* selected from the group consisting of ATCC PTA-9147 and ATCC PTA-9294, said progeny yielding a poppy straw having codeine constituting about 40% (preferably about 55%) by weight or greater of an alkaloid combination wherein the alkaloid combination comprises morphine, codeine, thebaine and oripavine.

The invention also includes a mutant or variant of a *Papaver somniferum* selected from the group consisting of ATCC PTA-9147 and ATCC PTA-9294, said mutant or variant yielding a poppy straw having codeine constituting about 40% (preferably about 55%) by weight or greater of an alkaloid combination wherein the alkaloid combination comprises morphine, codeine, thebaine and oripavine.

Another embodiment of the invention is plant cells, shoots or roots derived from any of the plants described above.

DETAILED DESCRIPTION OF THE INVENTION

Figure 1:
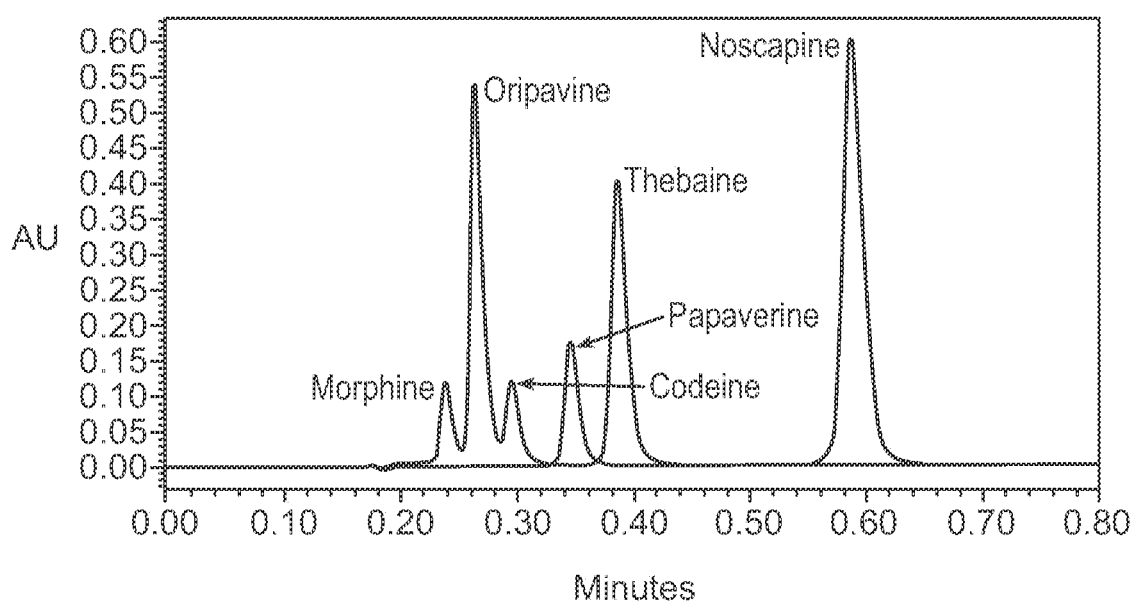
FIG. 1 provides a chromatogram showing separation of the alkaloids using the isocratic UPLC method.

Utilizing the mutagenized plants of *Papaver somniferum* as described herein, persons skilled in the art easily know how to grow them, reproduce them, collect the latex or the dried straw and purify the desired alkaloid, e.g., thebaine, codeine. As one enablement of the present invention, seeds to the mutagenized plants of *Papaver somniferum* (FN1-1242-3), as described herein, have been deposited under the Budapest Treaty with the American Type Culture Collection, 10801 University Boulevard, Manassas, Va. 20110-2209, on Mar. 20, 2008, under Accession No. ATCC PTA-9109, and will be made available upon the maturation of this application into a patent. In another enablement of the present invention, seeds to the mutagenized plants of *Papaver somniferum* (FW08-0039), as described herein, have been deposited under the Budapest Treaty with the American Type Culture Collection, 10801 University Boulevard, Manassas, Va. 20110-2209, on Apr. 9, 2008, under Accession No. ATCC PTA-9147, and will be made available upon the maturation of this application into a patent. In another enablement of the present invention, seeds to the mutagenized plants of *Papaver somniferum* (PH08-0002), as described herein, have been deposited under the Budapest Treaty with the American Type Culture Collection, 10801 University Boulevard, Manassas, Va. 20110-2209, on Jun. 26, 2008, under Accession No. ATCC PTA-9294. All restrictions on access to these deposits will be irrevocably removed at the time a patent issues in the United States on the basis of this application.

The availability of these seeds is not to be construed as a license to practice this invention in contravention of rights granted under the authority of any government in accordance with its patent or breeder's rights laws. Regardless of the enablement provided by these deposit, persons skilled in the art of mutagenizing seed, can obtain the seed herein by employing the mutagenesis process as described below.

The production of mutagenized seed is well known in the art. Methods of seed mutagenesis as well as mutagens suitable for use in these methods, such as, ethyl methanesulfonate (EMS), are described in the Manual on Mutation Breeding, 2nd ed., I.A.E.A., Vienna 1977 or in Plant Breeding, Principles and Prospects, Chapman and Hall, London 1993. For X-ray mutagenized seeds, hydrated seeds might be treated with 20,000 rads, (30 cm from the source for 45 minutes using a filter). X-ray mutagenesis is described and compared to EMS mutagenesis by Filippetti, A. et al., "Improvement of Seed Yield in *Vicia Faba* L. By Using Experimental Mutagenesis II Comparison of Gamma-Radiation and Ethyl-Methane-Sulphonate (EMS) in Production of Morphological Mutants", Euphytica 35 (1986) 49-59. DEB, diepoxybutane, mutagenized seeds might be obtained by soaking the seeds in water overnight, then soaking in 22 mM DEB for 4 hours, followed by extensive washing. Further mutagens include ethyl-2-chloroethyl sulphide, 2-chloroethyl-dimethylamine, ethylene oxide, ethyleneimine, dimethyl sulphonate, diethyl sulphonate, propane sulphone, beta-propiolactone, diazomethane, N-methyl-N-nitrosourethane, acridine orange and sodium azide.

Mutagenesis utilizing EMS is well described in the literature. The Manual on Mutation Breeding, supra, reports a preferred EMS mutagenesis process for barley seeds as practiced by K. Mikaelson. In this preferred process, the seeds are prepared, pre-soaked, treated with the mutagen and post-washed.

U.S. Pat. No. 6,067,749, incorporated by reference herein in its entirety, describes the use of EMS for the preparation of a *Papaver somniferum* strain with a high concentration of thebaine and oripavine.

Irradiation methods such as fast neutron mutagenesis may also be used to produce mutagenized seed. (See, Li, X. et al., A fast neutron deletion mutagenesis-based reverse genetics system for plants, The Plant Journal 27(3), 235-242 (2001)). Applicants employed and prefer fast neutron mutagenesis ("FNM") as the mutagen herein.

Fast neutron mutagenesis is described by Kodym and Afza (2003), Physical and Chemical Mutagenesis, pp 189-203, in Methods in Molecular Biology, vol 236: Plant Functional Genomics: Methods and Protocols (Ed. E. Grotewold), Humana Press Inc, Totowa, N.J.

Gamma (γ) Rays are electromagnetic waves of very short wavelengths and are obtained by disintegration of radioisotopes Co or Cs. γ sources can be installed in a γ cell, a γ room, or γ field. These are shielded by lead or concrete. Most γ sources as suitable for seed irradiation, as long as the size of irradiation space is sufficient and the dose rate allows practical irradiation times.

Fast neutrons are uncharged particles of high kinetic energy and are generated in nuclear reactors or in accelerators. The scientist should assess the feasibility for seed irradiation with the operators, since not all facilities are suitably equipped and can produce fast neutrons at a low degree of contamination with other radiation.

The two radiation types differ in their physical properties and, hence, in their mutagenic activity. γ Rays have a lower relative biological effectiveness (RBE) than fast neutrons, which implies that in order to obtain the same biological effect, a higher dose of γ radiation must be given. RBE is mainly a function of the linear energy transfer (LET), which is the transfer of energy along the ionizing track. γ Rays produce a few ionizations per micron of path (low LET) and belong to the category of sparsely ionizing radiation. Fast neutrons (high LET, densely ionizing radiation) impart some of their high kinetic energy via collisions, largely with protons within the material.

When radiation passes through tissue, physical events such as ionizations (ejection of electrons from molecules) and excitations (process of raising electrons to a higher energy state) occur and lead to effects in the DNA, membranes, lipids, enzymes, etc. Secondly, chemical events are induced that start with the formation of activated molecules, so-called free radicals (OH· and H·) that arise from OH− and H+. If oxygen is present, it reacts readily with radiation-induced free radicals to form peroxyradicals. In the case of low LET radiation, the formation of peroxyradicals is favoured. In high LET radiation, the formation of hydrogen peroxide ($H_2O_2$) by recombination of free radicals is favoured. All radicals and hydrogen peroxide can react with biological molecules. Primary damage caused by radiation occurs randomly and is both physiological and genetic. Physiological recovery and repair of DNA are possible to some extent, as non-damaged molecules may take over metabolic processes and DNA repair mechanisms are activated.

Before starting any mutation induction studies, it is most crucial to select suitable doses. For mutation induction, it is advisable to use two to three doses along with a control. The applicable doses will depend on the breeding or research objective, the radiation type and the particular plant material. It is known that plant genera and species and, to a lesser extent, cultivars differ in their radiosensitivity. Radiosensitivity (radiation sensitivity) is a relative measure that gives an indication of the quantity of recognizable effects of the radiation exposure on the irradiated object. The radiosensitivity is influenced by biological factors (such as genetic differences, nuclear and interphase chromosome vol) and by environmental modifying factors (oxygen, water content, post-irradiation storage, and temperature).

Modifying factors greatly affect mutagenic efficiency and reproducibility of results. Oxygen is the major modifying factor, while moisture content, temperature, and storage appear to be secondary, interacting with the oxygen effect. Oxygen shows synergistic action with sparsely ionizing radiation, but oxygen effects during irradiation and post-irradiation storage can easily be prevented by adjustment of seed water content to 12-14% in cereals and most other seeds. In oilseeds such as poppies, the seed water content should be lower, around 7-8%. The critical region is the embryo, but it can be assumed that the water content of the seed and the embryo of most species will be similar. Environmental factors are less important with densely ionizing radiation; thus, for fast neutron radiation, no seed moisture adjustment is necessary.

Unless data on the radiosensitivity of a given plant are already published or known from experience, the mutation induction program should be preceded by a radiosensitivity test. This is done by irradiating the seeds with a range of doses and by growing out the plants under greenhouse conditions. Radiosensitivity is assessed based on criteria such as reduced seedling height, fertility, and survival in the M1 generation. A seedling height reduction of 30-40% is generally assumed to give a high mutation yield. The usefulness of radiation can be judged by mutagenic efficiency, which is the production of desirable changes free from association with undesirable changes. A high dose will increase mutation frequency (the frequency at which a specific kind of mutation or mutant is found in a population of cells or individuals), but will be accompanied by negative features, such as sterility. When selecting the doses, it will be necessary to find a treatment regime providing high mutagenic efficiency.

For fast neutron radiation, dosimetric measurements have to be done during each radiation treatment, e.g., by performing the sulphur threshold detector method, since the neutron flux in the seed irradiation unit is not constant.

The Gray (symbol Gy), the SI (Systeme Internationale) unit used to quantify the absorbed dose of radiation (1 Gy=1 J/kg) replaced the old unit rad; 1 Gy=100 rads or 1 krad=10 Gy. The absorbed dose rate (Gy/s or Gy/min) indicates how much energy the irradiated material absorbs during a given unit of time. The length of exposure and the dose rate determines the radiation dose. Exposure during short times (s to a few h) at a high dose rate is referred to as acute and is most applied in irradiation programs.

We used the Atomic Energy Research Institute, Konkoly Thebe ut 29/33, X.epulet, H-1121 Budapest, Hungary to irradiate our seeds.

Fast neutrons have been shown to be a very effective mutagen. Kornneef et al. (1982) found that about 2500 lines treated with fast neutron at a does of 60 Gy are required to inactivate a gene once on average (Koornneef, M., Dellaert, L. W. M. and van der Veen, J. H. (1982) EMS- and radiation-induced mutation frequencies at individual loci in *Arabidopsis thaliana* (L.) Heynh. Mutat. Res. 93, 109-123). If the plant genome contains about 25000 genes, it is estimated that about 10 genes are randomly deleted in each line.

FNM offers a number of advantages over using chemical treatment such as EMS. Notably, the treatment is applied to the dried seed, which can be sown at a later date, while with EMS the seed needs either to be sown immediately after treatment, or carefully re-dried for sowing later.

After the seeds have been exposed to the mutagen, the seeds are grown to maturity in controlled conditions and self-pollinated. The seeds from the mature plant are taken and at least one seed is planted to grow an M2 generation. The M2 generation is screened for alkaloid production. Of course, it is possible to screen the M1 generation, but there are several advantages to screening the M2 generation. Firstly, screening the M2 generation insures that the trait resulting from mutagenesis can be inherited. Secondly, by growing the M2 generation, the basic hardiness of the plant is proven before screening. Thirdly, traits resulting from mutagenesis are generally inherited as recessive genes. Typically the mutated gene will be in the heterozygous state in the M1 generation, and thus the mutation will be masked by the dominant (non-mutated) form of the gene. In the M2 generation, however, in a proportion of the plants the gene will be in the homozygous state, and the affect of the mutation apparent. The M2 plants can be grown to produce an immature capsule, but it is possible to save time and labor if the plants are screened at an earlier stage of growth. It is recommended that the plants be screened at a point beginning at the 6 leaf stage, up to the 10 leaf stage. Screening at this early stage allows many plants to be managed in a small space. The screening process itself is the most labor intensive. Thus, to improve return on labor, only plants that appear healthy should be screened.

In the screening process, the objective is to measure each plant for morphine, codeine, thebaine and oripavine content. Additional alkaloids which can also be measured during the screening process include salutaridine, reticuline, laudanine, papaverine and noscapine. This can be accomplished by extracting, for example, a dry leaf into a liquid buffer or by dissolving a latex sample into a buffer. The buffer solutions are placed onto 96 well trays and fed mechanically through any of the high-throughput HPLCs available on the market. In a preferred embodiment, an isocratic Ultra high performance Liquid Chromatography (UPLC) method, as described herein, is utilized which provides very rapid latex screening.

A very rapid and efficient screening method is required in order to easily test sufficient plants to have a high probability of finding the required mutation. In the method described herein, the plant sampling method is very rapid because the latex droplet from the leaf sample bleeds out into the extraction buffer. There is no need for the technician to wait for each leaf to bleed out a latex sample, collect the latex droplet and transfer it to the buffer as done previously. Furthermore, using the Waters Acquity UPLC, the very sensitive UV detector allows very small alkaloid contents to be quantified, which means that even very small plants can be tested. Additionally, the very rapid 0.8 minute UPLC method allows over 1000 samples to be analysed daily, which means that the whole screening part of the project could be conducted in a few weeks.

Plants with altered alkaloid profiles are grown further and examined in more detail. According to the procedure herein, a second sample is taken from about 3% of plants to clarify or confirm the results of the initial screen. A more precise gradient UPLC method as described herein is used to obtain more accurate peak identification and quantification. Plants confirmed to have an unusual alkaloid profile are transplanted to 200 mm (approx 8 inch) pots for growing to maturity.

Twenty one plants having high thebaine and substantially no oripavine, morphine or codeine were found after screening approximately 34,358 plants. Fifty two high thebaine selections (including 9 of the 21 having substantially no oripavine, morphine or codeine) were cross pollinated with 3 different morphine-containing poppy lines. The F2 generation of plants from these crosses were then tested, and many were found to contain high contents of codeine, variable contents of thebaine and substantially no oripavine or morphine.

A more direct method of mutagenising a morphine-containing poppy line and then using an efficient screening method as described above (except that the screen would select morphine free plants containing high proportions of codeine) could alternatively be used to produce the same outcome. The proponents prefer the indirect method starting with a Norman poppy phenotype because there are fewer alkaloid peaks to separate in the LC method, which may permit a faster run-time.

As used herein, the term "poppy straw" or "straw" shall mean the straw material which results when the mature poppy capsules and the poppy capsule stems of a *Papaver somniferum* plant are collected, and threshed to remove the seeds to form a straw.

The term "opium", as used herein, shall refer to the air-dried, milky exudation (i.e., the latex) from incised, unripe poppy capsules of a *Papaver somniferum* plant.

As used herein, the term "concentrate of poppy straw" or "CPS" shall mean the material arising when poppy straw has entered into a process for the concentration of its alkaloids in either liquid, solid or powder form which contains the phenanthrene alkaloids of the opium poppy.

The phrase "stand of *Papaver somniferum*" or "stand of stably reproducing *Papaver somniferum*", as used herein, refers to a group of two or more *Papaver somniferum* plants or stably reproducing *Papaver somniferum* plants located together.

As used herein, the term "alkaloid combination" shall refer to a combination of alkaloids wherein the alkaloid comprises morphine, codeine, thebaine and oripavine. In another embodiment of the present invention, the alkaloid combination further comprises salutaridine, reticuline, laudanine, papaverine and noscapine in addition to morphine, codeine, thebaine and oripavine.

A "stably reproducing" *Papaver somniferum* poppy plant as described herein refers to a poppy plant that is stably reproducing as required to plant and harvest seed poppy crop over multiple generations where each generation would be suitable, without seed selection, for commercial planting of a field crop or stand of plants exhibiting the desired alkaloid characteristics. A stably reproducing poppy plant contains the desired alkaloid characteristics as described herein, and when self pollinated, or cross pollinated by a plant with the same genes controlling alkaloid content, produces a subsequent generation of plants which substantially all have the same desired alkaloid characteristics as the parent plant. Moreover, in the absence of pollination with pollen from other chemotypes (e.g., conventional morphine accumulating plants), the line will continue to produce similar plants over multiple generations, without the need for selection to maintain the desired alkaloid characteristic. Examples of desired alkaloid characteristics which can be passed on to future generations by a stably reproducing *Papaver somniferum* poppy plant include: (a) the improved thebaine characteristics (e.g., wherein thebaine constitutes about 90% (preferably, 95%, more preferably, 96% and most preferably, 97%) by weight or greater, and oripavine constitutes about 10% (preferably, 5%, more preferably, 1%, still more preferably, 0.8% and most preferably, 0.7%) by weight or less of the alkaloid combination) and wherein thebaine constitutes about 3.0% or greater of the poppy straw on a dry weight basis, and (b) the improved codeine characteristics (e.g., wherein codeine constitutes 55% (preferably, 75%, more preferably, 90% and most preferably, 96%) by weight or greater of the alkaloid combination, as described herein.

As used herein, the term "substantially no" when referring to thebaine content means that thebaine constitutes less than 5.0% by weight, preferably less than 2% by weight, and most preferably, less than 1% of the alkaloid combination of the poppy straw, concentrate of poppy straw or opium.

The term "substantially no", when referring to morphine, oripavine salutaridine, reticuline, laudanine, papaverine or noscapine, as used herein, means that each of the specified alkaloids constitutes less than 1% by weight, preferably, less than 0.5% by weight, more preferably, less than 0.3% by weight, and most preferably, between 0% and 0.2% by weight of the alkaloid combination of the poppy straw, concentrate of poppy straw or opium.

As used herein, the "M1 population" is the seeds and resulting plants exposed to a mutagenic agent, while "M2 population" is the progeny of self-pollinated M1 plants, "M3 population" is the progeny of self-pollinated M2 plants, "M4 population" is the the progeny of self-pollinated M3 plants, and generally "Mn population" is the progeny of self-pollinated Mn−1 plants.

The term "trait", as used herein, mean a distinct heritable phenotypic characteristic. The desired traits, i.e., high thebaine content versus oripavine, morphine or codeine content, or high codeine content versus oripavine, morphine or thebaine content, once established are consistently inherited by substantially all the progeny. To maintain the desired traits, care should be taken to prevent cross-pollination with normal plants unless such cross-pollination is part of a controlled breeding program.

The desired traits can be transferred into poppy lines having other characteristics (e.g. different height, early or late maturity or having disease resistance) by cross pollinating the high thebaine plant with the second parent plant, collecting F1 seed, growing a F1 plant which is allowed to self-pollinate and collect the F2 seed. The F2 seed would then be grown, and individual plants that have the high thebaine or codeine characteristic could be selected according to the methods herein, along with the other desired characteristics such as disease resistance. Further selection could then occur if desired in the F3 and/or subsequent generations in order to produce highly uniform lines. Alternatively, a high codeine plant can be used as the first parent in a crossing program. A skilled operator will be able to apply variations to this method as known in plant breeding.

Conducting test crosses with plants of known genotype can provide information regarding the genetic changes introduced through mutation. The characteristics of the F1 generation produced by crossing to a normal (wild type) parent will indicate whether a trait inherits as a recessive or dominant gene. Self pollinating the F1 plants and determining the phenotypes of the subsequent F2 population of plants will provide information regarding the numbers of genes responsible for particular characteristics.

The theory whereby mutagenesis has been found to be capable of raising the thebaine content of *Papaver somniferum* relative to the oripavine, morphine and codeine content is not capable of a certain or definite explanation at this time. The mutagenesis might have modified the biosynthesis pathway in any number of ways to minimize the production of oripavine. Despite the fact that definite answers are not now available, there are good reasons to believe that the correct answer is known.

*Papaver somniferum* is postulated to have two biosynthetic pathways from thebaine to morphine as shown in Scheme 1. Pathway A via neopinone, codeinone and codeine was proposed by Parker, H. I., J. Am. Chem. Soc., 94, 1276-1282 (1972). Pathway B via oripavine and morphinone was proposed by Brochmann-Hanssen, E., Planta Med., 50, 343-345 (1984). The enzyme codeinone reductase (NADPH) is believed to be active in both pathways, reducing codeinone to codeine and morphinone to morphine. Further, the TOP1 mutation (Millgate et al., Morphine-pathway block in top1 poppies. Nature, Vol. 431, 413-414, 2004) affects both pathways, preventing thebaine being converted to neopinone in Pathway A, and preventing oripavine being converted to morphinone in Pathway B. The TOP1 mutation appears to block demethylation of the enol ether which converts thebaine to neopinone, as well as the demethylation of the same enol ether in oripavine.

By the methods herein, plants of *Papaver somniferum* were obtained having a high thebaine content and substantially no oripavine, morphine or codeine. Both Pathway A and Pathway B were inoperative to produce morphine or any other alkaloids downstream of thebaine and oripavine in the parent line using the TOP1 mutation. The most probable step that has been affected by mutation is the phenolic 0-demethylation step between thebaine and oripavine. Thus, it is believed, for the *Papaver somniferum* plants described herein, that the production or activity of the phenolic O-demethylase enzyme that converts thebaine to oripavine has been substantially inhibited. Stably reproducing *Papaver somniferum* in accordance with the present invention may also be obtained by recombinant DNA techniques. In particular, after isolation and sequencing of the gene coding for thebaine demethylase, the gene may be modified or deleted to inhibit or prevent the production of thebaine demethylase. Techniques for modifying gene activity such as RNAi, antisense and other techniques are well known to those skilled in the art. Once the gene coding is established, a TILLING technique may be used to more efficiently recover mutants from populations (Henikoff, S., Till, B. J. and Comai, L. (2004) TILLING. Traditional mutagenesis meets functional genomics. Plant Physiology 135, 630-636).

By the methods herein, plants of *Papaver somniferum* were also obtained having codeine as the predominant alkaloid and substantially no oripavine or morphine. Plants were also obtained having codeine as the predominant alkaloid and substantially no oripavine, morphine, thebaine or any other alkaloids. These plants were derived from plants containing thebaine and having substantially no oripavine, morphine or codeine, by crossing said plants with plants of *Papaver somniferum* containing morphine. Whilst we cannot be certain of the reason that the new plants accumulate codeine, reference to the metabolic pathway suggests that the step between codeine and morphine has been substantially blocked. This suggests that the gene controlling the step between thebaine and oripavine that appears to have been blocked in the high thebaine poppy described above, is also responsible for the conversion of codeine to morphine. Therefore, when the gene responsible for producing thebaine-only poppies in conjunction with the TOP1 or Norman mutation is introduced into plants lacking that mutation, a codeine phenotype is produced. Knowing that there are genetic means of reducing the conversion of thebaine to oripavine and codeine to morphine in poppies, and that now that we have shown that these poppies are achievable and viable, even conventional breeding approaches may ultimately be used to develop such plants.

Scheme 1

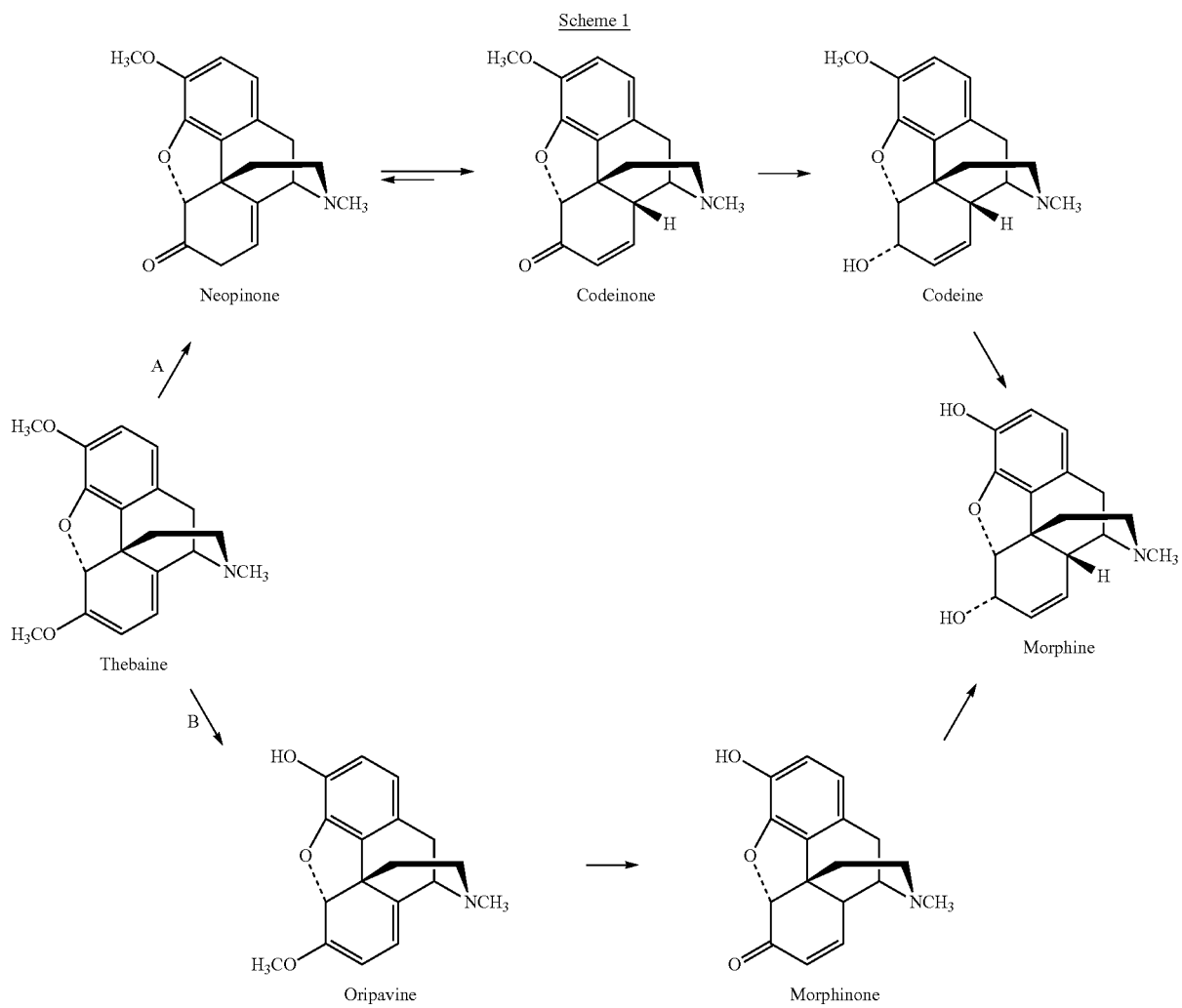

Postulated biosynthetic pathways in *Papaver somniferum*
A; Parker et al., 1972
B; Brochmann-Hanssen, 1984

A person skilled in the art of plant breeding will be able to further increase the codeine content, and vary the content of other alkaloids in plants of this invention, by using well know methods of plant breeding. For instance, by crossing with a wide range of poppy lines, and testing the progeny at the F2 or F3 or subsequent generations, it is likely that progeny will be able to be selected that have higher codeine content in the straw, through incorporation of genes from the new parent that contribute to codeine accumulation in some way.

Recovering the desired alkaloid, e.g., thebaine or codeine, from either the dried straw or from the opium of *Papaver somniferum* is a process well established in the art. Until now, thebaine has been extracted from this plant species either as a part of the process of extracting morphine and codeine, or more recently as part of the process of extracting thebaine and oripavine.

In one process, the straw is treated with a small amount of lime and water to soften the capsules and to form a free base of the alkaloids. Countercurrent extraction of the softened straw with methanol, ethanol or other suitable solvent forms a solvent/water extract or "miscella" containing the alkaloids, with morphine at a concentration of about 1 g/L where the straw is from standard *Papaver somniferum*. The volume of the miscella is reduced about 30× under vacuum to produce an aqueous concentrate. Thebaine is extracted from aqueous concentrate using a liquid/liquid extraction with toluene, adjusting pH for the best separation of thebaine. The thebaine is recovered from the toluene. Of course, recovering thebaine from the improved *Papaver somniferum* provided herein will be facilitated by the fact that the concentration of the thebaine in the miscella will be much higher than that of other alkaloids and thus can be more easily collected by precipitation. Also, in the substantial absence of oripavine, morphine and codeine, the thebaine might be directly extracted from the straw using toluene, xylene or other organic solvent in which thebaine has solubility.

In the case of codeine, any thebaine could be separated from codeine by one or more partitioning steps using an organic solvent (e.g. toluene or xylene), leaving codeine in the aqueous phase. Codeine CPS could then be precipitated from the aqueous phase by pH adjustment.

An alternative means of producing alkaloids is to grow plant cells or plant organs such as shoots or roots in culture.

Cell culture or organ culture are means of producing alkaloids without being subject to the vagaries of climate and other uncertainties associated with crop production. The general methods of establishing cell cultures, root cultures and shoot cultures for the purpose of alkaloid production are provided by M. F. Roberts, Production of alkaloids in plant cell culture. In Alkaloids, Biochemistry, Ecology, and Medicinal Applications, Edited by Roberts and Wink, Plenum Press, New York 1998, pages 159-197, the contents of which is hereby incorporated by reference in its entirety. The first step in producing cell cultures is to establish growth of callus. One way of achieving this for *Papaver somniferum* is provided by Chitty et al. (2003). (Genetic transformation in commercial Tasmanian cultivars of opium poppy, *Papaver somniferum* L., and movement of transgenic pollen in the field. Functional Plant Biology 30: 1045-1058.) In this method, seeds are surface sterilized by washing for 30-60 seconds in 70% ethanol, then in 1% (w/v) sodium hypochlorite solution plus 1-2 drops of autoclaved Tween 20 for 20 minutes with agitation. Seeds are then rinsed three to four times in sterile distilled water, or until no smell of bleach remains, and placed on B50 agar medium (Gamborg et al. 1968 Nutrient requirements of suspension cultures of soybean root cells. *Experimental Cell Research* 50, 151-158). Dishes are sealed with Parafilm and imbibed at 4° C. for 24 to 48 hours. Seeds are germinated at 24° C. in a 16 hour light-8 hour dark cycle. Hypocotyls are excised from seedlings after 7-8 days of culture, cut into 3-6 mm pieces (usually 1-3 explants per seedling) and placed onto callusing media. Culture media consists of B50 macronutrients, micronutrients, iron salts and vitamins (Gamborg et al. 1968) and sucrose at 20 g/L. pH can be adjusted with 1M KOH to pH 5.6 and 0.8% Sigma agar (A1296) can be used as a gelling agent.

All media should be autoclaved at 121° C. for 20 minutes. B50 medium contains no growth regulators and is used to germinate seeds aseptically, maintain embryogenic callus, and regenerate shoots and plantlets. Callusing Medium (CM) is B50 medium plus 2,4-dichlorophenoxy acetic acid (2,4-D) at 1 mg/l, added prior to the medium being autoclaved.

To generate a cell suspension culture (method from Staba et al. 1982, Alkaloid production from Papaver tissue cultures, Journal of Natural Products, 43, 256-262), callus cultures can be transferred into 125 mL Erlenmeyer flasks containing 25 mL of liquid RT medium (Khanna and Khanna 1976, Ind J Exp Biol 14, 628) supplemented with either 5 ppm BA for the growth of shoots or 0.1 ppm 2,4-D for the development of cell suspensions. Cultures can be grown at 28° C. on an orbital shaker (78 rpm) with 15 hours of light per day. Cell cultures can be grown as a batch culture where the cells multiply in a liquid medium which is being continuously agitated to maintain the cells as small aggregates and to maintain oxygen levels. Typically, after the initial inoculation there is a lag phase, followed by an exponential growth phase, which is then followed by a stationary phase where the growth becomes limited by lack of some components of the medium. Often, secondary plant products such as alkaloids are accumulated while the culture is in the stationary phase. For some products, alkaloid production can be induced by adding elicitors such as fungal cell extracts. There are also systems of continuous or semi-continuous culture where fresh medium is added either continuously or semi-continuously while cells or media are likewise removed for alkaloid recovery. Critical to the success of any cell culture system is the establishment of high yielding cell lines. Generally, selection is required to select individual plants, or individual cell cultures that produce the required alkaloid. For the production of codeine, a rapid HPLC or UPLC method such as those described in this application could be modified to test cell lines for codeine production.

Techniques such as root culture including hairy root culture where roots are transformed with *Agrobacterium rhizogenes* may also be a viable means of producing codeine in culture. A method for transformation of *Papaver somniferum* cultures with *A. rhizogenes* is provided by Yoshimatsu and Shimomura (1992) (Transformation of opium poppy (*Papaver somniferum* L.) with *Agrobacterium rhizogenes* MAFF 03-01724. Plant Cell Reports 11, 132-136. A person skilled in the art of cell and organ culture would also be able to envisage other means of growing plant cells derived from the plants described in this application in order to produce codeine.

The following Examples are set forth to aid in the understanding of the invention, and are not intended and should not be construed to limit in any way the invention set forth in the claims which follow thereafter.

Example 1

Thebaine Plant

A selection of *Papaver somniferum* poppy, WF03-0802 is used as the starting material. This line contains the TOP1 mutation and therefore has the characteristics of containing thebaine and oripavine in its poppy straw and opium, and is substantially free of morphine and codeine. Seeds of WF03-0802 have been deposited under the Budapest Treaty with the American Type Culture Collection, 10801 University Boulevard, Manassas, Va. 20110-2209, on Mar. 20, 2007, under Accession No. ATCC PTA-9110, and will be made available upon the maturation of this application into a patent. The availability of these seeds is not to be construed as a license to practice this invention in contravention of rights granted under the authority of any government in accordance with its patent or breeder's rights laws.

Six seed samples each of 10 g were prepared. One sample was retained as a control. After obtaining the necessary inspections and permits, the 5 samples were sent to the Atomic Energy Research Institute, Budapest, Hungary for irradiation. At the Institute, the samples were removed from their vials, packed into plastic bags and cadmium holders and irradiated with fast neutrons. The dose rates and exposure times were as follows:

| | |
|---|---|
| Treatment 1 | 10 Gy 13 minutes 17 seconds |
| Treatment 2 | 20 Gy 26 minutes 30 seconds |
| Treatment 3 | 25 Gy 33 minutes 16 seconds |
| Treatment 4 | 35 Gy 46 minutes 27 seconds |
| Treatment 5 | 50 Gy 66 minutes 13 seconds |

The reported parameters of the irradiation were as follows:

Irradiation geometry at BIF of BRR at AERI: 2 Y/Cd, rotated

Monitored by U-235, Th-232 fission chambers and GM counter.

The dose homogeneity within one package is better than 1%

The overall dose uncertainty is less than 5%.

Total surface gamma activity of samples after irradiation: ~695 BGND

Total surface gamma activity of samples on 20 Oct. 2005: <2 BGND
(1 BGND (background) is ~90 nGy/h)

The seeds were returned to applicants by the Institute, reweighed, and found to have lost an average mass of 1.1%. This is compatible with being transferred into and out of plastic bags, as well as losing some moisture during irradiation.

Samples of the seeds were placed on damp filter paper in a Petri dish. After 3 and 7 days, the seeds were examined. Treatments 1 to 4 germinated well, while treatment 5 had very short radicles and only a small percentage of plants with shoots.

A pot trial was grown to evaluate the effect of the FNM treatment on plant growth. Two pots were sown with 10 seeds from each of treatments 1, 2, 3, 5 and control. These pots were observed for emergence and plant growth. Irradiation reduced plant emergence and survival from a mean of 9 plants per pot in the control treatment to 8.5 plants in Treatment 1, 7.5 plants in treatment 2, 7 plants in treatment 3, and 4 plants in treatment 5. Development was also delayed with increasing dose, and plant height was reduced by about 10% in treatment 1, 20% in treatment 2, and 40% in treatment 3.

The seeds from the treatments 2 and 3 were sown into 200 mm pots filled with potting mix from Forestry Commission Nursery at Perth, Tasmania. 10 seeds were sown per pot, and were covered with vermiculite. The plants were grown through to maturity in a greenhouse. The plants were thinned out to 6 poppies per pot when poppies were at the cotyledon to two leaf stage. A fungicide drench (Previcur) was applied a few days and five weeks after sowing at a rate of 15 mL per 72 pots to protect against *Pythium* spp. and other fungal diseases. A nutrient solution was applied 3-4 times during the growing season to provide all essential plant nutrients. Overhead irrigation was used during the first four weeks of the plant growth and drip irrigation was used thereafter with each multi-outlet dripper supplying 8 pots. The greenhouse was maintained between 15 and 25° C. using a combination of ventilation and heating.

All flowers were self pollinated by transferring pollen from the anthers onto the stigmatic disc. The mature capsules were harvested into large paper bags labeled with the treatment number, keeping the different treatments separate. Where there were 2 or more capsules on one plant, these were picked into a small paper bag so they stayed together. Distinctive plants were harvested into separate bags and notes made on their appearance. The harvested capsules were stored for a week or so to ensure that the seed was air dry.

The seed was separated from the capsules in the laboratory, and weighed into paper envelopes labeled with FN1-X where FN1 refers to Fast Neutron experiment 1, and X is the sequence number of the seed sample. The seed from multiple capsules from the same plant was combined into the one sample.

The seed from a total of 8,495 plants was harvested. 7,280 of these were from radiation treatment 2. The median weight of seeds harvested per M1 plant was 0.41 g.

Growth and Screening of M2 Generation

Plant Growth

M2 plants were grown in a greenhouse in trays each with 288 cells. 12 cells were sown with seed from each M1 plant. Two seeds were sown in each cell, and thinned to one plant per cell after 1-2 weeks. The plants were sown in batches of 4-17 trays each week to spread the workload over 17 weeks. The plants were watered using spray irrigation, and the greenhouse was maintained at 15-25° C.

Leaf Sampling

When the plants were approximately 6 weeks old, they were analysed for alkaloid profile using the latex from the youngest fully expanded leaf (YFEL). 240 µL of latex extraction solution (23 g $NH_4H_2PO_4$ dissolved in 800 mL deionized (DI) water, made up to 1 L with ethanol) was added to the wells of 96 well filter plates (Pall AcroPrep™ 96 Filter Plate 0.2 µm GHP membrane, natural housing, 350 µL PN S5045, (Pall Corporation, East Hills, N.Y.)). The tip of the YFEL was removed from each plant and placed in a well of the filter plate using fine forceps. Three filter plates were required to sample the plants in one tray. The plates were allowed to stand for about 30 minutes after sampling to allow the latex to bleed out of the leaves into the extraction solution. The solution was then filtered into a 96 well collection plate, which was sealed with an ABgene® Adhesive PCR foil seals (ABgene, part of ThermoFisher Scientific, Rockford, Ill.) to eliminate evaporation.

UPLC Method

The isocratic UPLC method used for the first screening stage is described in Example 2. Peak areas were exported to a Excel file (Microsoft Corporation, Seattle, Wash.) for data analysis. No correction was applied for differing UV absorption between the alkaloid peaks. The relative absorption of oripavine and thebaine, the main peaks of interest, were in any case very similar at the wavelength used.

Data Analysis

Relative peak areas were calculated for all identified alkaloids. The Excel data files were then sorted to identify plants having high thebaine content and low oripavine content relative to all identified alkaloids extracted. The chromatograms of plants identified as being of interest were reviewed to ensure that the peaks of interest were correctly integrated.

Confirmation

The plants identified in the first screening were then resampled to provide confirmation of the alkaloid profile, and to ensure that the correct plant was located prior to transplanting. The selected plants were marked with a plastic coated wire when retested so that they could be identified reliably for transplanting. A gradient UPLC system with a 2.5 minute run time (described in Example 2) was used in the confirmation testing in order to obtain more accurate peak identification and integration.

Transplanting

Plants confirmed as being of interest were transplanted into 200 mm pots, and labelled with a code, indicating the M1 seed line from which they were derived. For instance, if two selections were made from the M1 seed sample labelled FN1-1234, these selections were labelled FN1-1234-1, and FN1-1234-2. Up to 5 plants were transplanted into each pot.

Table 2, below, shows the number of plants analysed, the number of selections made, and the number of selections confirmed. Over the project, 34,358 M2 plants (from 4,176 M1 lines) were tested, and 1,049 were selected for further testing. 549 of these were confirmed and transplanted into pots. Of the 549 transplanted, 366 were selected on the basis of high thebaine and low oripavine content.

TABLE 2

| Batch | Irradiation Treatment No. | Tray numbers | Number plants analysed | Selections No. | Selections % selns | Confirmations No. | Confirmations % of plants | Confirmations % of selections |
|---|---|---|---|---|---|---|---|---|
| 1 | 2 | 1-4 | 927 | 51 | 5.5 | 23 | 2.5 | 45 |
| 2 | 2 | 5-8 | 856 | 15 | 1.8 | 12 | 1.4 | 80 |
| 3 | 2 | 9-12 | 914 | 29 | 3.2 | 23 | 2.5 | 79 |
| 4 | 2 | 13-16 | 976 | 37 | 3.8 | 27 | 2.8 | 73 |
| 5 | 2 | 17-20 | 924 | 40 | 4.3 | 14 | 1.5 | 35 |
| 6 | 2 | 21-28 | 1900 | 47 | 2.5 | 21 | 1.1 | 45 |
| 7 | 2 | 29-35 | 1670 | 27 | 1.6 | 16 | 1.0 | 59 |
| 8 | 2 | 36-43 | 1746 | 85 | 4.9 | 30 | 1.7 | 35 |
| 9 | 2 | 44-52 | 2134 | 39 | 1.8 | 39 | 1.8 | 100 |
| 10 | 2 | 53-60 | 1890 | 31 | 1.6 | 31 | 1.6 | 100 |
| 11 | 2 | 61-77 | 3524 | 104 | 3.0 | 51 | 1.4 | 49 |
| 12 | 2 | 78-91 | 2737 | 86 | 3.1 | 29 | 1.1 | 34 |
| 13 | 2 | 92-111 | 4591 | 119 | 2.6 | 58 | 1.3 | 49 |
| 14 | 3 | 297-313 | 2808 | 109 | 3.9 | 74 | 2.6 | 68 |
| 15 | 2 | 129-145 | 2108 | 117 | 5.6 | 44 | 2.1 | 38 |
| 16 | 2 | 146-162 | 2467 | 56 | 2.3 | 34 | 1.4 | 61 |
| 17 | 2 | 163-174 | 2186 | 57 | 2.6 | 23 | 1.1 | 40 |
| Totals: | | | 34358 | 1049 | 3.1 | 549 | 1.60 | 52.3 |

Table 3, below, lists the 366 selections made on the basis of high thebaine and low oripavine content in latex from leaf samples. The alkaloid profile is based on peak area, not alkaloid concentration.

TABLE 3

| Seln No. | M1 Seed Line | Tray | Plate/ Position | Alkaloid profile (percentage of area under peaks) | | | | | | | | | Selection name |
|---|---|---|---|---|---|---|---|---|---|---|---|---|---|
| | | | | Morphine | Oripavine | Salutaridine | Codeine | Reticuline | Laudanine | Papaverine | Thebaine | Noscapine | |
| 29 | 105 | 7 | P20 B10 | 2 | 1.7 | 1 | 0 | 0 | 1 | 0 | 94 | 0 | FN1-105-2 |
| 41 | 165 | 9 | P27 B8 | 0 | 4.9 | 1 | 0 | 1 | 2 | 0 | 90 | 1 | FN1-165-1 |
| 42 | 165 | 9 | P27 B9 | 0 | 4.4 | 2 | 0 | 2 | 2 | 0 | 90 | 0 | FN1-165-2 |
| 46 | 183 | 10 | P29 C6 | 0 | 6.5 | 1 | 0 | 1 | 1 | 0 | 91 | 0 | FN1-183-1 |
| 54 | 223 | 12 | P34 B1 | 0 | 5.7 | 2 | 0 | 0 | 2 | 0 | 91 | 0 | FN1-223-1 |
| 64 | 269 | 13 | P39 D9 | 0 | 3.7 | 1 | 0 | 1 | 1 | 0 | 92 | 0 | FN1-269-1 |
| 65 | 270 | 13 | P39 E3 | 0 | 4.5 | 2 | 0 | 1 | 1 | 0 | 90 | 0 | FN1-270-1 |
| 66 | 272 | 13 | P39 G8 | 0 | 2.3 | 1 | 0 | 2 | 1 | 0 | 92 | 0 | FN1-272-1 |
| 68 | 291 | 14 | P42 B12 | 0 | 2.2 | 2 | 0 | 1 | 1 | 0 | 93 | 0 | FN1-291-1 |
| 72 | 300 | 15 | P43 C10 | 0 | 6.3 | 1 | 0 | 1 | 1 | 0 | 90 | 1 | FN1-300-2 |
| 74 | 317 | 15 | P45 D2 | 0 | 2.4 | 1 | 0 | 0 | 0 | 0 | 96 | 0 | FN1-317-1 |
| 77 | 329 | 16 | P46 H2 | 0 | 4.9 | 1 | 0 | 1 | 1 | 0 | 92 | 0 | FN1-329-1 |
| 78 | 333 | 16 | P47 D10 | 0 | 5.4 | 1 | 0 | 1 | 0 | 0 | 93 | 0 | FN1-333-1 |
| 79 | 340 | 16 | P48 C1 | 0 | 5.8 | 0 | 0 | 1 | 1 | 0 | 91 | 1 | FN1-340-1 |
| 80 | 340 | 16 | P48 C2 | 0 | 6.1 | 0 | 0 | 1 | 1 | 0 | 91 | 1 | FN1-340-2 |
| 83 | 340 | 16 | P48 C10 | 1 | 6.4 | 1 | 0 | 1 | 1 | 0 | 90 | 0 | FN1-340-5 |
| 84 | 345 | 16 | P48 H1 | 0 | 2.6 | 1 | 0 | 2 | 1 | 0 | 92 | 1 | FN1-345-1 |
| 85 | 345 | 16 | P48 H5 | 0 | 4.9 | 1 | 0 | 2 | 1 | 0 | 91 | 1 | FN1-345-2 |
| 94 | 399 | 19 | P55 F9 | 0 | 1.5 | 0 | 0 | 1 | 2 | 0 | 92 | 1 | FN1-399-3 |
| 95 | 399 | 19 | P55 F11 | 0 | 2.1 | 0 | 0 | 1 | 0 | 3 | 90 | 0 | FN1-399-4 |
| 96 | 404 | 19 | P56 C5 | 0 | 1.5 | 0 | 0 | 1 | 1 | 0 | 93 | 0 | FN1-404-1 |
| 100 | 461 | 21 | P63 D6 | 0 | 3.6 | 1 | 0 | 1 | 1 | 1 | 92 | 0 | FN1-461-1 |
| 103 | 486 | 22 | P66 D1 | 0 | 3.5 | 1 | 0 | 2 | 2 | 0 | 91 | 1 | FN1-486-1 |
| 106 | 557 | 25 | P75 C1 | 0 | 1.1 | 0 | 0 | 0 | 0 | 0 | 98 | 0 | FN1-557-1 |
| 107 | 593 | 27 | P79 G5 | 0 | 3.9 | 0 | 0 | 1 | 1 | 0 | 94 | 1 | FN1-593-1 |
| 110 | 601 | 27 | P80 G6 | 0 | 0.4 | 0 | 0 | 1 | 0 | 0 | 97 | 1 | FN1-601-1 |
| 111 | 607 | 27 | P81 E12 | 0 | 3.5 | 0 | 0 | 1 | 0 | 0 | 95 | 0 | FN1-607-1 |
| 114 | 622 | 28 | P83 D9 | 0 | 4.3 | 0 | 0 | 1 | 1 | 0 | 93 | 1 | FN1-622-1 |
| 115 | 625 | 28 | P83 G12 | 0 | 3.6 | 0 | 0 | 1 | 1 | 0 | 94 | 0 | FN1-625-1 |
| 117 | 630 | 28 | P84 D11 | 0 | 4.4 | 0 | 0 | 0 | 0 | 0 | 96 | 0 | FN1-630-1 |
| 119 | 633 | 28 | P84 G9 | 0 | 4.3 | 0 | 0 | 2 | 1 | 0 | 92 | 1 | FN1-633-1 |
| 120 | 503 | 23 | P68 E8 | 0 | 3.3 | 1 | 0 | 1 | 0 | 0 | 94 | 0 | FN1-503-1 |
| 122 | 640 | 29 | P85 F8 | 0 | 4.0 | 0 | 0 | 1 | 1 | 0 | 93 | 1 | FN1-640-1 |
| 123 | 658 | 29 | P87 H4 | 0 | 5.8 | 0 | 0 | 2 | 1 | 0 | 90 | 0 | FN1-658-1 |
| 124 | 674 | 30 | P89 H7 | 0 | 2.8 | 0 | 0 | 1 | 1 | 0 | 95 | 1 | FN1-674-1 |
| 125 | 675 | 30 | P90 A10 | 0 | 1.5 | 0 | 0 | 1 | 2 | 0 | 94 | 1 | FN1-675-1 |
| 127 | 736 | 33 | P97 F8 | 0 | 3.9 | 0 | 0 | 1 | 1 | 0 | 93 | 1 | FN1-736-1 |
| 128 | 743 | 33 | P98 E8 | 0 | 4.2 | 0 | 0 | 3 | 1 | 0 | 91 | 1 | FN1-743-1 |
| 129 | 748 | 33 | P99 B7 | 0 | 4.8 | 0 | 0 | 2 | 1 | 0 | 91 | 1 | FN1-748-1 |

TABLE 3-continued

| | M1 | | | Alkaloid profile (percentage of area under peaks) | | | | | | | | | |
|---|---|---|---|---|---|---|---|---|---|---|---|---|---|
| Seln No. | Seed Line | Tray | Plate/ Position | Mor- phine | Oripavine | Salutaridine | Co- deine | Reticuline | Lauda- nine | Papav- erine | The- baine | Noscapine | Selection name |
| 130 | 754 | 33 | P99 H8 | 0 | 5.6 | 0 | 0 | 2 | 1 | 0 | 91 | 1 | FN1-754-1 |
| 131 | 754 | 33 | P99 H12 | 0 | 4.1 | 0 | 0 | 1 | 1 | 0 | 93 | 1 | FN1-754-2 |
| 132 | 775 | 34 | P102 E8 | 0 | 3.9 | 0 | 0 | 2 | 1 | 0 | 93 | 0 | FN1-775-1 |
| 134 | 695 | 31 | P92 E4 | 0 | 9.0 | 0 | 0 | 0 | 0 | 0 | 90 | 1 | FN1-695-2 |
| 139 | 809 | 36 | P106 G1 | 0 | 1.7 | 0 | 0 | 0 | 8 | 0 | 91 | 0 | FN1-809-1 |
| 140 | 809 | 36 | P106 G2 | 0 | 0.0 | 0 | 0 | 0 | 0 | 4 | 96 | 0 | FN1-809-2 |
| 143 | 841 | 37 | P110 G10 | 4 | 2.1 | 0 | 0 | 0 | 0 | 0 | 94 | 0 | FN1-841-1 |
| 144 | 846 | 37 | P111 D1 | 1 | 2.0 | 0 | 0 | 1 | 1 | 0 | 95 | 0 | FN1-846-1 |
| 145 | 846 | 37 | P111 D2 | 0 | 0.0 | 0 | 0 | 0 | 0 | 0 | 100 | 0 | FN1-846-2 |
| 146 | 846 | 37 | P111 D12 | 0 | 1.1 | 0 | 0 | 2 | 0 | 0 | 97 | 0 | FN1-846-3 |
| 147 | 874 | 38 | P114 H5 | 0 | 1.6 | 0 | 0 | 0 | 0 | 0 | 98 | 0 | FN1-874-1 |
| 148 | 874 | 38 | P114 H6 | 0 | 3.2 | 0 | 0 | 0 | 0 | 0 | 97 | 0 | FN1-874-2 |
| 149 | 875 | 39 | P115 A5 | 0 | 0.0 | 0 | 0 | 0 | 0 | 0 | 100 | 0 | FN1-875-1 |
| 150 | 884 | 39 | P116 B9 | 3 | 2.0 | 0 | 0 | 0 | 0 | 0 | 95 | 0 | FN1-884-1 |
| 153 | 900 | 40 | P118 B1 | 0 | 0.0 | 0 | 0 | 0 | 0 | 0 | 98 | 1 | FN1-900-1 |
| 154 | 900 | 40 | P118 B3 | 0 | 0.5 | 0 | 0 | 0 | 1 | 0 | 97 | 1 | FN1-900-2 |
| 155 | 900 | 40 | P118 B6 | 0 | 0.3 | 0 | 0 | 0 | 0 | 0 | 97 | 1 | FN1-900-3 |
| 156 | 900 | 40 | P118 B8 | 0 | 0.0 | 0 | 0 | 0 | 0 | 0 | 98 | 1 | FN1-900-4 |
| 157 | 900 | 40 | P118 B12 | 0 | 0.0 | 0 | 0 | 1 | 1 | 0 | 98 | 0 | FN1-900-5 |
| 158 | 902 | 40 | P118 D3 | 0 | 1.6 | 0 | 0 | 0 | 0 | 0 | 97 | 0 | FN1-902-1 |
| 159 | 912 | 40 | P119 F4 | 0 | 1.8 | 0 | 0 | 1 | 0 | 1 | 92 | 1 | FN1-912-1 |
| 160 | 915 | 40 | P120 A6 | 0 | 1.9 | 0 | 0 | 0 | 1 | 0 | 93 | 2 | FN1-915-1 |
| 161 | 916 | 40 | P120 B12 | 0 | 1.2 | 0 | 0 | 0 | 1 | 0 | 98 | 0 | FN1-916-1 |
| 162 | 945 | 41 | P123 G8 | 0 | 2.5 | 0 | 0 | 0 | 0 | 0 | 94 | 1 | FN1-945-1 |
| 163 | 945 | 41 | P123 G11 | 0 | 1.6 | 0 | 0 | 0 | 0 | 0 | 96 | 0 | FN1-945-2 |
| 167 | 998 | 44 | P130 D6 | 0 | 0.8 | 0 | 0 | 0 | 0 | 0 | 99 | 0 | FN1-998-1 |
| 168 | 998 | 44 | P130 D8 | 0 | 2.1 | 0 | 0 | 0 | 0 | 0 | 97 | 0 | FN1-998-2 |
| 172 | 1027 | 45 | P134 A4 | 0 | 0.9 | 0 | 0 | 0 | 0 | 0 | 98 | 0 | FN1-1027-1 |
| 173 | 1027 | 45 | P134 A10 | 0 | 1.4 | 0 | 0 | 0 | 0 | 0 | 98 | 0 | FN1-1027-2 |
| 174 | 1050 | 46 | P136 H5 | 0 | 1.6 | 0 | 0 | 0 | 0 | 0 | 98 | 0 | FN1-1050-1 |
| 175 | 1050 | 46 | P136 H11 | 0 | 2.5 | 0 | 0 | 0 | 1 | 0 | 96 | 0 | FN1-1050-2 |
| 176 | 1085 | 47 | P141 C5 | 0 | 2.7 | 0 | 0 | 0 | 0 | 0 | 96 | 0 | FN1-1085-1 |
| 178 | 1108 | 48 | P144 B, 3 | 0 | 0.0 | 3 | 0 | 0 | 0 | 0 | 97 | 0 | FN1-1108-1 |
| 179 | 1116 | 49 | P145 B, 9 | 0 | 3.6 | 0 | 0 | 0 | 0 | 0 | 94 | 1 | FN1-1116-1 |
| 180 | 1123 | 49 | P146 A, 11 | 0 | 3.6 | 0 | 0 | 0 | 0 | 0 | 95 | 0 | FN1-1123-1 |
| 181 | 1133 | 49 | P147 C, 9 | 0 | 1.3 | 0 | 0 | 0 | 1 | 0 | 93 | 2 | FN1-1133-1 |
| 183 | 1139 | 50 | P148 A, 5 | 0 | 2.9 | 0 | 0 | 0 | 0 | 1 | 95 | 1 | FN1-1139-1 |
| 184 | 1139 | 50 | P148 A, 8 | 0 | 3.8 | 0 | 1 | 0 | 0 | 2 | 92 | 1 | FN1-1139-2 |
| 185 | 1141 | 50 | P148 C, 6 | 0 | 0.0 | 1 | 1 | 0 | 0 | 0 | 95 | 1 | FN1-1141-1 |
| 187 | 1149 | 50 | P149 C, 3 | 0 | 1.3 | 0 | 0 | 0 | 0 | 0 | 97 | 2 | FN1-1149-1 |
| 188 | 1153 | 50 | P149 G, 4 | 0 | 0.4 | 0 | 0 | 0 | 0 | 1 | 97 | 0 | FN1-1153-1 |
| 192 | 1170 | 51 | P151 H, 2 | 0 | 3.6 | 0 | 0 | 0 | 0 | 0 | 94 | 1 | FN1-1170-1 |
| 194 | 1176 | 51 | P152 F, 12 | 0 | 3.9 | 0 | 0 | 0 | 0 | 0 | 93 | 1 | FN1-1176-1 |
| 195 | 1180 | 51 | P153 B, 7 | 0 | 0.7 | 0 | 2 | 0 | 1 | 0 | 92 | 2 | FN1-1180-1 |
| 196 | 1180 | 51 | P153 B, 10 | 0 | 2.5 | 0 | 0 | 0 | 0 | 0 | 97 | 0 | FN1-1180-2 |
| 197 | 1183 | 51 | P153 E, 9 | 0 | 0.9 | 0 | 0 | 0 | 0 | 2 | 95 | 1 | FN1-1183-1 |
| 198 | 1183 | 51 | P153 E, 11 | 0 | 0.8 | 0 | 0 | 0 | 0 | 0 | 94 | 3 | FN1-1183-2 |
| 199 | 1185 | 51 | P153 G, 8 | 0 | 0.4 | 0 | 1 | 0 | 0 | 0 | 98 | 0 | FN1-1185-1 |
| 200 | 1186 | 51 | P153 H, 9 | 0 | 2.2 | 0 | 0 | 0 | 0 | 0 | 95 | 1 | FN1-1186-1 |
| 203 | 1201 | 52 | P155 G, 3 | 0 | 3.5 | 0 | 0 | 1 | 0 | 0 | 93 | 1 | FN1-1201-1 |
| 204 | 1204 | 52 | P156 B, 1 | 0 | 3.0 | 0 | 0 | 0 | 0 | 0 | 95 | 1 | FN1-1204-1 |
| 205 | 1211 | 52 | P156 G, 2 | 0 | 2.5 | 0 | 0 | 0 | 0 | 0 | 95 | 0 | FN1-1211-1 |
| 208 | 1242 | 54 | P160 E1 | 0 | 0.0 | 0 | 0 | 0 | 0 | 0 | 100 | 0 | FN1-1242-1 |
| 209 | 1242 | 54 | P160 E8 | 0 | 0.0 | 0 | 0 | 0 | 0 | 0 | 100 | 0 | FN1-1242-2 |
| 210 | 1242 | 54 | P160 E9 | 0 | 0.0 | 0 | 0 | 0 | 0 | 0 | 100 | 0 | FN1-1242-3 |
| 213 | 1270 | 55 | P164 A11 | 0 | 0.0 | 0 | 0 | 0 | 0 | 0 | 100 | 0 | FN1-1270-1 |
| 214 | 1272 | 55 | P164 C6 | 0 | 0.0 | 0 | 0 | 0 | 0 | 0 | 100 | 0 | FN1-1272-1 |
| 216 | 1303 | 56 | P168 B, 2 | 0 | 4.3 | 0 | 0 | 1 | 1 | 0 | 92 | 1 | FN1-1303-1 |
| 217 | 1313 | 57 | P169 D, 8 | 0 | 5.2 | 0 | 0 | 0 | 0 | 1 | 94 | 0 | FN1-1313-1 |
| 218 | 1326 | 57 | P171 A, 5 | 0 | 3.9 | 0 | 0 | 0 | 0 | 0 | 93 | 1 | FN1-1326-1 |
| 219 | 1326 | 57 | P171 A, 11 | 0 | 2.5 | 0 | 1 | 0 | 0 | 1 | 94 | 1 | FN1-1326-2 |
| 220 | 1331 | 57 | P171 F, 7 | 0 | 2.3 | 0 | 0 | 0 | 0 | 0 | 96 | 1 | FN1-1331-1 |
| 224 | 1366 | 59 | P176 3: A, 11 | 0 | 1.9 | 0 | 0 | 0 | 0 | 0 | 98 | 1 | FN1-1366-1 |
| 225 | 1370 | 59 | P176 3: E, 6 | 0 | 2.2 | 0 | 0 | 0 | 0 | 0 | 97 | 0 | FN1-1370-1 |
| 226 | 1373 | 59 | P176 3: H, 11 | 0 | 0.5 | 0 | 0 | 0 | 0 | 0 | 99 | 0 | FN1-1373-1 |
| 227 | 1376 | 59 | P177 4: C, 4 | 0 | 0.0 | 0 | 0 | 0 | 0 | 0 | 98 | 0 | FN1-1376-1 |
| 229 | 1381 | 59 | P177 4: H, 11 | 0 | 2.2 | 0 | 0 | 0 | 0 | 0 | 97 | 1 | FN1-1381-1 |
| 230 | 1387 | 60 | P178 5: F, 1 | 0 | 1.2 | 0 | 0 | 0 | 0 | 0 | 97 | 0 | FN1-1387-1 |
| 232 | 1401 | 60 | P180 7: D, 11 | 0 | 0.0 | 0 | 0 | 0 | 0 | 0 | 95 | 1 | FN1-1401-1 |
| 233 | 1402 | 60 | P180 7: E, 12 | 0 | 0.0 | 0 | 0 | 0 | 0 | 0 | 96 | 3 | FN1-1402-1 |
| 234 | 1403 | 60 | P180 7: F, 1 | 0 | 1.2 | 0 | 0 | 0 | 0 | 0 | 95 | 1 | FN1-1403-1 |
| 235 | 1405 | 60 | P180 7: H, 5 | 0 | 0.0 | 0 | 0 | 0 | 0 | 0 | 96 | 2 | FN1-1405-1 |
| 236 | 1405 | 60 | P180 7: H, 6 | 0 | 0.0 | 0 | 0 | 0 | 0 | 1 | 97 | 0 | FN1-1405-2 |
| 237 | 1413 | 61 | P181 H4 | 0 | 0.0 | 0 | 0 | 0 | 0 | 0 | 100 | 0 | FN1-1413-1 |
| 238 | 1419 | 61 | P182 F2 | 0 | 0.0 | 0 | 0 | 0 | 0 | 0 | 100 | 0 | FN1-1419-1 |

TABLE 3-continued

| | M1 | | | Alkaloid profile (percentage of area under peaks) | | | | | | | | | |
|---|---|---|---|---|---|---|---|---|---|---|---|---|---|
| Seln No. | Seed Line | Tray | Plate/ Position | Mor- phine | Oripavine | Salutaridine | Co- deine | Reticuline | Lauda- nine | Papav- erine | The- baine | Noscapine | Selection name |
| 239 | 1432 | 62 | P184 C3 | 0 | 0.0 | 0 | 0 | 0 | 0 | 0 | 100 | 0 | FN1-1432-1 |
| 240 | 1444 | 62 | P185 G1 | 0 | 0.0 | 0 | 0 | 0 | 0 | 0 | 100 | 0 | FN1-1444-1 |
| 241 | 1447 | 62 | P186 B3 | 0 | 0.0 | 0 | 0 | 0 | 0 | 0 | 100 | 0 | FN1-1447-1 |
| 242 | 1474 | 63 | P189 E7 | 0 | 0.0 | 0 | 0 | 0 | 0 | 0 | 100 | 0 | FN1-1474-1 |
| 245 | 1519 | 65 | P195 B6 | 0 | 0.0 | 0 | 0 | 0 | 0 | 0 | 100 | 0 | FN1-1519-1 |
| 246 | 1519 | 65 | P195 B7 | 0 | 0.0 | 0 | 0 | 0 | 0 | 0 | 100 | 0 | FN1-1519-2 |
| 248 | 1533 | 66 | P196 H12 | 0 | 0.0 | 0 | 0 | 0 | 0 | 0 | 100 | 0 | FN1-1533-1 |
| 249 | 1534 | 66 | P197 A5 | 0 | 0.0 | 0 | 0 | 0 | 0 | 0 | 100 | 0 | FN1-1534-1 |
| 250 | 1534 | 66 | P197 A6 | 0 | 0.0 | 0 | 0 | 0 | 0 | 0 | 100 | 0 | FN1-1534-2 |
| 251 | 1535 | 66 | P197 B11 | 0 | 0.0 | 0 | 0 | 0 | 0 | 0 | 100 | 0 | FN1-1535-1 |
| 252 | 1536 | 66 | P197 C7 | 0 | 1.7 | 0 | 0 | 0 | 0 | 0 | 98 | 0 | FN1-1536-1 |
| 254 | 1567 | 67 | P201 B7 | 0 | 0.0 | 0 | 0 | 0 | 0 | 0 | 100 | 0 | FN1-1567-1 |
| 255 | 1571 | 67 | P201 F10 | 0 | 0.0 | 0 | 0 | 0 | 0 | 0 | 100 | 0 | FN1-1571-1 |
| 256 | 1571 | 67 | P201 F11 | 0 | 0.0 | 0 | 0 | 0 | 0 | 0 | 100 | 0 | FN1-1571-2 |
| 257 | 1571 | 67 | P201 F12 | 0 | 0.0 | 0 | 0 | 0 | 2 | 0 | 98 | 0 | FN1-1571-3 |
| 258 | 1571 | 67 | P201 F2 | 0 | 0.0 | 0 | 0 | 0 | 0 | 0 | 100 | 0 | FN1-1571-4 |
| 259 | 1571 | 67 | P201 F3 | 0 | 0.0 | 0 | 0 | 0 | 0 | 0 | 100 | 0 | FN1-1571-5 |
| 260 | 1571 | 67 | P201 F4 | 0 | 0.0 | 0 | 0 | 0 | 0 | 0 | 100 | 0 | FN1-1571-6 |
| 261 | 1571 | 67 | P201 F5 | 0 | 0.0 | 0 | 0 | 0 | 0 | 0 | 100 | 0 | FN1-1571-7 |
| 262 | 1571 | 67 | P201 F7 | 0 | 0.0 | 0 | 0 | 0 | 0 | 0 | 100 | 0 | FN1-1571-8 |
| 263 | 1571 | 67 | P201 F8 | 0 | 0.0 | 0 | 0 | 0 | 0 | 0 | 100 | 0 | FN1-1571-9 |
| 264 | 1571 | 67 | P201 F9 | 0 | 0.0 | 0 | 0 | 0 | 0 | 0 | 100 | 0 | FN1-1571-10 |
| 265 | 1573 | 67 | P201 H12 | 0 | 0.0 | 0 | 0 | 0 | 0 | 0 | 100 | 0 | FN1-1573-1 |
| 268 | 1600 | 69 | P205 C11 | 0 | 0.0 | 0 | 0 | 0 | 0 | 0 | 100 | 0 | FN1-1600-1 |
| 269 | 1621 | 69 | P207 H4 | 0 | 0.0 | 0 | 0 | 0 | 0 | 0 | 100 | 0 | FN1-1621-1 |
| 270 | 1625 | 70 | P208 D2 | 0 | 1.9 | 2 | 0 | 1 | 2 | 0 | 94 | 0 | FN1-1625-1 |
| 271 | 1659 | 71 | P212 F8 | 0 | 1.4 | 0 | 0 | 2 | 0 | 0 | 97 | 0 | FN1-1659-1 |
| 272 | 1660 | 71 | P212 G8 | 0 | 1.9 | 0 | 0 | 1 | 0 | 0 | 97 | 0 | FN1-1660-1 |
| 273 | 1662 | 71 | P213 A11 | 0 | 1.8 | 1 | 0 | 1 | 0 | 0 | 96 | 0 | FN1-1662-1 |
| 274 | 1662 | 71 | P213 A12 | 0 | 1.5 | 0 | 0 | 1 | 0 | 0 | 97 | 0 | FN1-1662-2 |
| 275 | 1701 | 73 | P217 H2 | 0 | 1.0 | 0 | 0 | 0 | 0 | 0 | 99 | 0 | FN1-1701-1 |
| 276 | 1702 | 73 | P218 A11 | 0 | 2.0 | 0 | 0 | 0 | 0 | 0 | 97 | 1 | FN1-1702-1 |
| 277 | 1703 | 73 | P218 B2 | 0 | 1.3 | 0 | 0 | 0 | 0 | 0 | 99 | 0 | FN1-1703-1 |
| 279 | 1719 | 74 | P220 B1 | 0 | 0.0 | 0 | 0 | 0 | 0 | 0 | 100 | 0 | FN1-1719-1 |
| 280 | 1741 | 74 | P222 H8 | 0 | 1.5 | 0 | 0 | 0 | 0 | 0 | 98 | 0 | FN1-1741-1 |
| 281 | 1741 | 74 | P222 H12 | 0 | 0.0 | 0 | 0 | 0 | 0 | 0 | 100 | 0 | FN1-1741-2 |
| 282 | 1744 | 75 | P223 C9 | 0 | 0.0 | 0 | 0 | 0 | 0 | 0 | 100 | 0 | FN1-1744-1 |
| 283 | 1763 | 75 | P225 F8 | 0 | 0.0 | 0 | 0 | 0 | 0 | 0 | 100 | 0 | FN1-1763-1 |
| 284 | 1771 | 76 | P226 F2 | 0 | 0.8 | 1 | 0 | 0 | 0 | 0 | 98 | 0 | FN1-1771-1 |
| 285 | 1771 | 76 | P226 F3 | 0 | 0.0 | 0 | 0 | 0 | 0 | 0 | 100 | 0 | FN1-1771-2 |
| 287 | 1813 | 77 | P231 H11 | 0 | 1.8 | 1 | 0 | 1 | 0 | 0 | 94 | 0 | FN1-1813-1 |
| 290 | 1835 | 78 | P234 C9 | 0 | 1.9 | 0 | 0 | 3 | 3 | 0 | 92 | 0 | FN1-1835-2 |
| 291 | 1835 | 78 | P234 C11 | 0 | 1.8 | 0 | 0 | 4 | 2 | 0 | 92 | 0 | FN1-1835-3 |
| 292 | 1841 | 79 | P235 D8 | 0 | 0.0 | 0 | 0 | 0 | 0 | 0 | 100 | 0 | FN1-1841-1 |
| 295 | 1869 | 80 | P238 H5 | 0 | 0.9 | 0 | 0 | 0 | 0 | 0 | 99 | 0 | FN1-1869-1 |
| 296 | 1869 | 80 | P238 H8 | 0 | 1.4 | 0 | 0 | 0 | 0 | 0 | 98 | 0 | FN1-1869-2 |
| 298 | 1898 | 81 | P242 E5 | 0 | 1.3 | 0 | 0 | 1 | 1 | 0 | 97 | 0 | FN1-1898-1 |
| 299 | 1913 | 82 | P244 D4 | 0 | 0.0 | 0 | 0 | 0 | 0 | 0 | 100 | 0 | FN1-1913-1 |
| 301 | 1944 | 83 | P248 C1 | 0 | 1.6 | 0 | 0 | 1 | 0 | 0 | 97 | 0 | FN1-1944-1 |
| 304 | 2017 | 86 | P257 C12 | 0 | 1.0 | 1 | 0 | 0 | 0 | 0 | 98 | 0 | FN1-2017-1 |
| 307 | 2085 | 89 | P265 G1 | 0 | 2.3 | 0 | 0 | 0 | 0 | 0 | 96 | 0 | FN1-2085-1 |
| 308 | 2085 | 89 | P265 G2 | 0 | 1.4 | 0 | 0 | 0 | 0 | 0 | 99 | 0 | FN1-2085-2 |
| 309 | 2103 | 89 | P267 H2 | 0 | 1.2 | 0 | 0 | 0 | 0 | 0 | 99 | 0 | FN1-2103-1 |
| 310 | 2114 | 90 | P269 C2 | 0 | 0.8 | 1 | 0 | 1 | 0 | 0 | 97 | 0 | FN1-2114-1 |
| 311 | 2115 | 90 | P269 D5 | 0 | 1.0 | 0 | 0 | 0 | 0 | 0 | 99 | 0 | FN1-2115-1 |
| 312 | 2152 | 91 | P273 H3 | 0 | 0.8 | 0 | 0 | 0 | 0 | 0 | 99 | 0 | FN1-2152-1 |
| 313 | 2152 | 91 | P273 H7 | 0 | 0.0 | 0 | 0 | 0 | 0 | 0 | 100 | 0 | FN1-2152-2 |
| 314 | 2152 | 91 | P273 H9 | 0 | 0.8 | 0 | 0 | 0 | 0 | 0 | 99 | 0 | FN1-2152-3 |
| 315 | 2152 | 91 | P273 H11 | 0 | 0.0 | 0 | 0 | 0 | 0 | 0 | 100 | 0 | FN1-2152-4 |
| 317 | 2154 | 92 | P274 B4 | 0 | 4.1 | 0 | 0 | 0 | 0 | 4 | 92 | 0 | FN1-2154-1 |
| 318 | 2172 | 92 | P276 D7 | 0 | 0.0 | 0 | 0 | 0 | 0 | 0 | 100 | 0 | FN1-2172-1 |
| 319 | 2175 | 92 | P276 G8 | 0 | 0.0 | 0 | 0 | 0 | 0 | 0 | 100 | 0 | FN1-2175-1 |
| 321 | 2186 | 93 | P278 B6 | 0 | 2.0 | 0 | 0 | 0 | 0 | 0 | 98 | 0 | FN1-2186-1 |
| 322 | 2186 | 93 | P278 B11 | 0 | 0.0 | 0 | 0 | 0 | 0 | 0 | 98 | 0 | FN1-2186-2 |
| 324 | 2196 | 93 | P279 D5 | 0 | 1.3 | 0 | 1 | 1 | 3 | 0 | 94 | 0 | FN1-2196-1 |
| 325 | 2199 | 93 | P279 G3 | 0 | 0.0 | 0 | 0 | 0 | 0 | 0 | 100 | 0 | FN1-2199-1 |
| 326 | 2199 | 93 | P279 G10 | 0 | 0.0 | 0 | 0 | 0 | 0 | 0 | 100 | 0 | FN1-2199-2 |
| 327 | 2200 | 93 | P279 H1 | 0 | 0.0 | 0 | 0 | 0 | 0 | 0 | 97 | 0 | FN1-2200-1 |
| 330 | 2215 | 94 | P281 G2 | 0 | 0.0 | 0 | 0 | 0 | 0 | 3 | 91 | 0 | FN1-2215-1 |
| 331 | 2215 | 94 | P281 G6 | 0 | 0.0 | 0 | 0 | 0 | 0 | 0 | 97 | 0 | FN1-2215-2 |
| 332 | 2219 | 94 | P282 B2 | 0 | 0.0 | 0 | 0 | 0 | 0 | 0 | 100 | 0 | FN1-2219-1 |
| 333 | 2219 | 94 | P282 B6 | 0 | 0.0 | 0 | 0 | 0 | 0 | 0 | 100 | 0 | FN1-2219-2 |
| 335 | 2221 | 94 | P282 D8 | 0 | 0.0 | 4 | 0 | 0 | 0 | 4 | 93 | 0 | FN1-2221-1 |
| 336 | 2224 | 94 | P282 G4 | 0 | 0.0 | 0 | 0 | 0 | 0 | 0 | 100 | 0 | FN1-2224-1 |
| 337 | 2231 | 95 | P283 F5 | 0 | 0.0 | 0 | 0 | 0 | 0 | 0 | 100 | 0 | FN1-2231-1 |

TABLE 3-continued

| Seln No. | M1 Seed Line | Tray | Plate/ Position | Morphine | Oripavine | Salutaridine | Codeine | Reticuline | Laudanine | Papaverine | Thebaine | Noscapine | Selection name |
|---|---|---|---|---|---|---|---|---|---|---|---|---|---|
| 338 | 2231 | 95 | P283 F12 | 0 | 0.0 | 0 | 0 | 0 | 0 | 0 | 100 | 0 | FN1-2231-2 |
| 339 | 2233 | 95 | P283 H7 | 0 | 3.0 | 0 | 0 | 0 | 0 | 0 | 97 | 0 | FN1-2233-1 |
| 340 | 2241 | 95 | P284 H1 | 0 | 0.0 | 0 | 0 | 0 | 0 | 0 | 100 | 0 | FN1-2241-1 |
| 341 | 2241 | 95 | P284 H4 | 0 | 2.7 | 0 | 0 | 0 | 0 | 0 | 97 | 0 | FN1-2241-2 |
| 342 | 2243 | 95 | P285 B9 | 0 | 0.0 | 0 | 0 | 0 | 0 | 0 | 96 | 0 | FN1-2243-1 |
| 343 | 2245 | 95 | P285 C5 | 0 | 0.0 | 0 | 0 | 0 | 0 | 0 | 98 | 0 | FN1-2245-1 |
| 344 | 2245 | 95 | P285 C10 | 0 | 0.0 | 0 | 0 | 0 | 0 | 0 | 100 | 0 | FN1-2245-2 |
| 345 | 2255 | 96 | P286 E9 | 0 | 0.0 | 0 | 0 | 0 | 0 | 0 | 100 | 0 | FN1-2255-1 |
| 346 | 2267 | 96 | P288 A10 | 1 | 0.0 | 1 | 0 | 0 | 0 | 0 | 99 | 0 | FN1-2267-1 |
| 349 | 2280 | 97 | P289 F11 | 0 | 0.0 | 0 | 0 | 0 | 5 | 0 | 91 | 4 | FN1-2280-1 |
| 354 | 2288 | 97 | P290 F9 | 0 | 0.9 | 0 | 0 | 1 | 1 | 0 | 96 | 1 | FN1-2288-1 |
| 355 | 2325 | 99 | P295 C5 | 0 | 0.0 | 0 | 0 | 0 | 0 | 0 | 100 | 0 | FN1-2325-1 |
| 356 | 2329 | 99 | P295 G4 | 0 | 0.0 | 0 | 0 | 2 | 2 | 0 | 97 | 0 | FN1-2329-1 |
| 357 | 2365 | 100 | P300 C9 | 0 | 0.0 | 0 | 0 | 0 | 2 | 0 | 98 | 0 | FN1-2365-1 |
| 358 | 2372 | 101 | P301 B1 | 0 | 0.0 | 0 | 0 | 0 | 0 | 0 | 100 | 0 | FN1-2372-1 |
| 361 | 2412 | 102 | P306 B2 | 0 | 0.7 | 0 | 0 | 0 | 0 | 0 | 99 | 0 | FN1-2412-1 |
| 362 | 2425 | 103 | P307 G8 | 0 | 0.0 | 0 | 0 | 0 | 0 | 0 | 100 | 0 | FN1-2425-1 |
| 363 | 2427 | 103 | P308 A6 | 0 | 0.0 | 0 | 0 | 0 | 0 | 0 | 100 | 0 | FN1-2427-1 |
| 364 | 2437 | 103 | P309 C12 | 0 | 0.0 | 0 | 0 | 0 | 0 | 0 | 100 | 0 | FN1-2437-1 |
| 365 | 2443 | 104 | P310 A1 | 0 | 0.7 | 0 | 0 | 1 | 0 | 0 | 97 | 0 | FN1-2443-1 |
| 367 | 2492 | 106 | P316 A5 | 0 | 0.0 | 0 | 0 | 0 | 1 | 0 | 99 | 0 | FN1-2492-1 |
| 374 | 2604 | 110 | P330 A6 | 0 | 0.0 | 0 | 0 | 0 | 1 | 0 | 99 | 0 | FN1-2604-1 |
| 376 | 7299 | 298 | P892 C2 | 0 | 0.0 | 0 | 0 | 0 | 3 | 0 | 97 | 0 | FN1-7299-2 |
| 377 | 7299 | 298 | P892 C3 | 0 | 0.0 | 0 | 0 | 0 | 2 | 0 | 98 | 0 | FN1-7299-3 |
| 378 | 7299 | 298 | P892 C4 | 0 | 0.5 | 0 | 0 | 0 | 1 | 0 | 98 | 0 | FN1-7299-4 |
| 379 | 7299 | 298 | P892 C10 | 0 | 0.7 | 0 | 0 | 0 | 2 | 0 | 98 | 0 | FN1-7299-5 |
| 380 | 7299 | 298 | P892 C12 | 0 | 0.0 | 0 | 0 | 0 | 3 | 0 | 97 | 0 | FN1-7299-6 |
| 381 | 7303 | 298 | P892 G10 | 0 | 0.0 | 0 | 0 | 0 | 0 | 0 | 100 | 0 | FN1-7303-1 |
| 382 | 7304 | 298 | P892 H2 | 0 | 0.0 | 0 | 0 | 0 | 0 | 0 | 100 | 0 | FN1-7304-1 |
| 383 | 7304 | 298 | P892 H5 | 0 | 0.0 | 0 | 0 | 1 | 1 | 0 | 98 | 0 | FN1-7304-2 |
| 384 | 7306 | 298 | P893 B6 | 0 | 0.0 | 0 | 0 | 0 | 1 | 0 | 98 | 1 | FN1-7306-1 |
| 385 | 7325 | 299 | P895 E10 | 0 | 0.0 | 1 | 0 | 1 | 2 | 0 | 97 | 0 | FN1-7325-1 |
| 386 | 7329 | 299 | P896 A8 | 0 | 0.0 | 0 | 0 | 0 | 0 | 0 | 100 | 0 | FN1-7329-1 |
| 387 | 7329 | 299 | P896 A10 | 0 | 0.0 | 0 | 0 | 0 | 1 | 0 | 99 | 0 | FN1-7329-2 |
| 388 | 7332 | 299 | P896 D3 | 0 | 0.0 | 0 | 0 | 0 | 1 | 0 | 99 | 0 | FN1-7332-1 |
| 389 | 7341 | 299 | P897 E3 | 0 | 0.0 | 0 | 0 | 0 | 0 | 0 | 100 | 0 | FN1-7341-1 |
| 390 | 7342 | 299 | P897 F1 | 0 | 0.0 | 0 | 1 | 0 | 2 | 0 | 97 | 0 | FN1-7342-1 |
| 391 | 7342 | 299 | P897 F9 | 0 | 0.0 | 0 | 1 | 0 | 2 | 0 | 96 | 1 | FN1-7342-2 |
| 393 | 7348 | 300 | P898 D5 | 0 | 1.1 | 0 | 0 | 0 | 0 | 0 | 99 | 0 | FN1-7348-1 |
| 394 | 7353 | 300 | P898 H1 | 0 | 0.6 | 0 | 0 | 0 | 0 | 0 | 99 | 0 | FN1-7353-1 |
| 395 | 7354 | 300 | P899 A3 | 0 | 0.0 | 0 | 0 | 0 | 1 | 0 | 99 | 0 | FN1-7354-1 |
| 396 | 7354 | 300 | P899 A8 | 0 | 0.0 | 0 | 0 | 0 | 1 | 0 | 99 | 0 | FN1-7354-2 |
| 397 | 7355 | 300 | P899 B2 | 0 | 0.0 | 0 | 0 | 0 | 0 | 0 | 100 | 0 | FN1-7355-1 |
| 398 | 7355 | 300 | P899 B5 | 0 | 0.0 | 0 | 0 | 0 | 1 | 0 | 99 | 0 | FN1-7355-2 |
| 399 | 7373 | 301 | P901 C10 | 0 | 1.0 | 0 | 0 | 0 | 0 | 0 | 99 | 0 | FN1-7373-1 |
| 400 | 7378 | 301 | P901 H1 | 0 | 0.0 | 0 | 0 | 1 | 0 | 0 | 99 | 0 | FN1-7378-1 |
| 401 | 7380 | 301 | P902 B9 | 0 | 0.0 | 0 | 0 | 0 | 0 | 0 | 100 | 0 | FN1-7380-1 |
| 402 | 7386 | 301 | P902 H6 | 0 | 0.0 | 0 | 0 | 1 | 1 | 0 | 98 | 0 | FN1-7386-1 |
| 403 | 7386 | 301 | P902 H9 | 0 | 0.0 | 0 | 0 | 0 | 0 | 0 | 100 | 0 | FN1-7386-2 |
| 404 | 7397 | 302 | P904 B1 | 0 | 0.0 | 0 | 0 | 0 | 0 | 0 | 100 | 0 | FN1-7397-1 |
| 405 | 7399 | 302 | P904 D3 | 0 | 0.0 | 0 | 0 | 0 | 3 | 0 | 97 | 0 | FN1-7399-1 |
| 406 | 7400 | 302 | P904 E12 | 0 | 0.0 | 0 | 0 | 0 | 0 | 0 | 100 | 0 | FN1-7400-1 |
| 407 | 7445 | 303 | P909 H12 | 0 | 0.9 | 0 | 0 | 0 | 1 | 0 | 98 | 0 | FN1-7445-1 |
| 408 | 7447 | 304 | P910 B9 | 0 | 0.7 | 0 | 0 | 0 | 0 | 0 | 98 | 0 | FN1-7447-1 |
| 409 | 7448 | 304 | P910 C6 | 0 | 0.0 | 0 | 0 | 0 | 0 | 0 | 98 | 2 | FN1-7448-1 |
| 410 | 7452 | 304 | P910 G1 | 0 | 0.0 | 0 | 0 | 1 | 1 | 0 | 98 | 0 | FN1-7452-1 |
| 411 | 7462 | 304 | P911 H6 | 0 | 0.9 | 0 | 0 | 0 | 0 | 1 | 99 | 0 | FN1-7462-1 |
| 412 | 7467 | 304 | P912 C1 | 0 | 0.6 | 0 | 0 | 0 | 1 | 0 | 97 | 0 | FN1-7467-1 |
| 413 | 7467 | 304 | P912 C2 | 0 | 0.4 | 1 | 0 | 0 | 2 | 0 | 97 | 0 | FN1-7467-2 |
| 414 | 7471 | 304 | P912 G7 | 0 | 1.0 | 0 | 0 | 0 | 0 | 0 | 98 | 1 | FN1-7471-1 |
| 415 | 7472 | 304 | P912 H2 | 0 | 0.0 | 0 | 0 | 0 | 0 | 0 | 95 | 5 | FN1-7472-1 |
| 416 | 7491 | 305 | P914 G8 | 0 | 0.8 | 0 | 0 | 0 | 0 | 0 | 99 | 0 | FN1-7491-1 |
| 417 | 7499 | 305 | P915 F2 | 0 | 1.2 | 0 | 0 | 0 | 0 | 0 | 99 | 0 | FN1-7499-1 |
| 418 | 7506 | 306 | P916 B6 | 0 | 1.1 | 0 | 0 | 1 | 0 | 1 | 97 | 0 | FN1-7506-1 |
| 419 | 7509 | 306 | P916 D1 | 0 | 0.0 | 0 | 0 | 0 | 0 | 0 | 100 | 0 | FN1-7509-1 |
| 420 | 7513 | 306 | P916 H5 | 0 | 1.0 | 0 | 0 | 1 | 1 | 0 | 96 | 1 | FN1-7513-1 |
| 421 | 7525 | 306 | P918 C10 | 0 | 1.3 | 0 | 0 | 1 | 1 | 0 | 95 | 1 | FN1-7525-1 |
| 422 | 7529 | 306 | P918 G11 | 0 | 0.0 | 0 | 0 | 0 | 0 | 0 | 100 | 0 | FN1-7529-1 |
| 423 | 7535 | 307 | P919 E8 | 0 | 0.0 | 0 | 0 | 0 | 0 | 0 | 97 | 3 | FN1-7535-1 |
| 424 | 7536 | 307 | P919 F1 | 0 | 1.2 | 0 | 0 | 2 | 1 | 0 | 96 | 0 | FN1-7536-1 |
| 426 | 7551 | 307 | P921 C5 | 0 | 0.0 | 0 | 0 | 0 | 0 | 0 | 100 | 0 | FN1-7551-1 |
| 427 | 7557 | 308 | P922 A12 | 0 | 0.0 | 0 | 0 | 0 | 0 | 0 | 100 | 0 | FN1-7557-1 |
| 428 | 7558 | 308 | P922 B7 | 0 | 0.0 | 0 | 0 | 0 | 0 | 0 | 100 | 0 | FN1-7558-1 |
| 429 | 7560 | 308 | P922 D8 | 0 | 1.2 | 0 | 0 | 0 | 1 | 0 | 98 | 0 | FN1-7560-1 |
| 430 | 7566 | 308 | P923 B9 | 0 | 0.0 | 0 | 0 | 0 | 0 | 2 | 98 | 0 | FN1-7566-1 |

TABLE 3-continued

| | M1 | | | Alkaloid profile (percentage of area under peaks) | | | | | | | | |
|---|---|---|---|---|---|---|---|---|---|---|---|---|
| Seln No. | Seed Line | Tray | Plate/ Position | Mor- phine | Oripavine | Salutaridine | Co- deine | Reticuline | Lauda- nine | Papav- erine | The- baine | Noscapine | Selection name |
| 431 | 7579 | 308 | P924 F3 | 0 | 0.8 | 0 | 0 | 3 | 0 | 2 | 92 | 2 | FN1-7579-1 |
| 432 | 7584 | 309 | P925 B3 | 0 | 0.0 | 0 | 0 | 1 | 1 | 0 | 98 | 0 | FN1-7584-1 |
| 433 | 7587 | 309 | P925 E7 | 0 | 0.0 | 0 | 0 | 0 | 0 | 0 | 100 | 0 | FN1-7587-1 |
| 434 | 7592 | 309 | P926 B2 | 0 | 0.0 | 0 | 0 | 0 | 0 | 0 | 100 | 0 | FN1-7592-1 |
| 435 | 7592 | 309 | P926 B4 | 0 | 0.7 | 0 | 0 | 1 | 1 | 0 | 97 | 0 | FN1-7592-2 |
| 436 | 7598 | 309 | P926 H3 | 0 | 0.7 | 0 | 0 | 1 | 2 | 0 | 95 | 1 | FN1-7598-1 |
| 437 | 7598 | 309 | P926 H10 | 0 | 0.7 | 1 | 0 | 1 | 1 | 0 | 96 | 1 | FN1-7598-2 |
| 438 | 7600 | 309 | P927 B1 | 0 | 0.0 | 0 | 0 | 0 | 0 | 0 | 100 | 0 | FN1-7600-1 |
| 439 | 7600 | 309 | P927 B5 | 0 | 0.0 | 0 | 0 | 0 | 0 | 0 | 100 | 0 | FN1-7600-2 |
| 440 | 7629 | 310 | P930 C8 | 0 | 1.1 | 0 | 1 | 0 | 0 | 0 | 95 | 1 | FN1-7629-1 |
| 441 | 7640 | 311 | P931 B4 | 0 | 0.0 | 0 | 1 | 0 | 0 | 0 | 96 | 1 | FN1-7640-1 |
| 442 | 7647 | 311 | P931 F1 | 0 | 0.0 | 0 | 3 | 0 | 0 | 0 | 96 | 0 | FN1-7647-1 |
| 443 | 7656 | 311 | P932 F3 | 0 | 1.7 | 0 | 1 | 0 | 0 | 0 | 94 | 1 | FN1-7656-1 |
| 444 | 7666 | 311 | P933 G8 | 0 | 1.0 | 0 | 1 | 0 | 0 | 0 | 95 | 1 | FN1-7666-1 |
| 445 | 7674 | 312 | P934 F3 | 0 | 1.4 | 0 | 1 | 0 | 0 | 0 | 96 | 1 | FN1-7674-1 |
| 446 | 7686 | 312 | P936 A6 | 0 | 0.0 | 0 | 0 | 0 | 0 | 0 | 100 | 0 | FN1-7686-1 |
| 447 | 7702 | 313 | P937 H8 | 0 | 0.9 | 0 | 0 | 0 | 0 | 0 | 98 | 1 | FN1-7702-1 |
| 448 | 7718 | 313 | P939 G6 | 0 | 0.0 | 0 | 0 | 0 | 1 | 0 | 99 | 0 | FN1-7718-1 |
| 450 | 3122 | 132 | P394 E2 | 0 | 0.0 | 0 | 0 | 0 | 5 | 0 | 95 | 0 | FN1-3122-1 |
| 451 | 3123 | 132 | P394 F12 | 0 | 0.0 | 0 | 0 | 0 | 5 | 0 | 95 | 0 | FN1-3123-1 |
| 452 | 3132 | 132 | P395 G11 | 0 | 0.0 | 0 | 0 | 0 | 6 | 0 | 94 | 0 | FN1-3132-1 |
| 453 | 3141 | 132 | P396 G1 | 0 | 0.8 | 0 | 0 | 1 | 1 | 0 | 96 | 1 | FN1-3141-1 |
| 454 | 3141 | 132 | P396 G10 | 0 | 0.0 | 0 | 0 | 0 | 0 | 4 | 96 | 0 | FN1-3141-2 |
| 455 | 3158 | 133 | P398 G6 | 0 | 0.0 | 0 | 0 | 0 | 3 | 0 | 97 | 0 | FN1-3158-1 |
| 456 | 3176 | 134 | P400 G1 | 0 | 0.9 | 0 | 0 | 3 | 1 | 0 | 95 | 0 | FN1-3176-1 |
| 457 | 3206 | 135 | P404 E3 | 0 | 0.0 | 0 | 0 | 0 | 0 | 4 | 96 | 0 | FN1-3206-1 |
| 458 | 3209 | 135 | P404 H11 | 0 | 0.0 | 0 | 0 | 1 | 0 | 2 | 96 | 1 | FN1-3209-1 |
| 459 | 3215 | 135 | P405 F5 | 0 | 1.0 | 0 | 0 | 1 | 0 | 2 | 95 | 1 | FN1-3215-1 |
| 460 | 3228 | 136 | P407 C8 | 0 | 0.0 | 0 | 0 | 1 | 2 | 0 | 97 | 0 | FN1-3228-1 |
| 461 | 3258 | 137 | P410 G4 | 0 | 0.0 | 0 | 0 | 1 | 0 | 4 | 94 | 1 | FN1-3258-1 |
| 462 | 3270 | 138 | P412 B3 | 0 | 0.0 | 0 | 0 | 0 | 5 | 0 | 95 | 0 | FN1-3270-1 |
| 463 | 3288 | 138 | P414 C7 | 0 | 0.0 | 0 | 0 | 0 | 0 | 3 | 97 | 0 | FN1-3288-1 |
| 464 | 3295 | 139 | P415 A2 | 0 | 0.0 | 0 | 0 | 2 | 4 | 0 | 94 | 0 | FN1-3295-1 |
| 465 | 3296 | 139 | P415 B10 | 0 | 0.0 | 0 | 0 | 0 | 3 | 0 | 97 | 0 | FN1-3296-1 |
| 466 | 3296 | 139 | P415 B12 | 0 | 1.0 | 0 | 0 | 0 | 2 | 0 | 97 | 0 | FN1-3296-2 |
| 467 | 3297 | 139 | P415 C12 | 0 | 0.0 | 0 | 0 | 1 | 0 | 3 | 95 | 0 | FN1-3297-1 |
| 468 | 3299 | 139 | P415 E1 | 0 | 0.0 | 0 | 0 | 0 | 0 | 3 | 96 | 1 | FN1-3299-1 |
| 469 | 3300 | 139 | P415 F2 | 0 | 0.0 | 0 | 0 | 1 | 0 | 3 | 95 | 0 | FN1-3300-1 |
| 472 | 3310 | 139 | P416 H4 | 0 | 0.0 | 0 | 0 | 0 | 2 | 0 | 96 | 1 | FN1-3310-1 |
| 473 | 3320 | 140 | P418 B10 | 0 | 0.6 | 0 | 0 | 1 | 2 | 0 | 96 | 1 | FN1-3320-1 |
| 474 | 3326 | 140 | P418 H2 | 0 | 0.0 | 0 | 0 | 0 | 2 | 0 | 98 | 0 | FN1-3326-1 |
| 475 | 3328 | 140 | P419 B2 | 0 | 0.0 | 0 | 0 | 1 | 1 | 0 | 98 | 1 | FN1-3328-1 |
| 476 | 3328 | 140 | P419 B7 | 0 | 0.0 | 0 | 0 | 0 | 0 | 7 | 91 | 0 | FN1-3328-2 |
| 477 | 3306 | 139 | P416 D7 | 0 | 3.9 | 0 | 0 | 0 | 0 | 1 | 94 | 1 | FN1-3306-1 |
| 478 | 3365 | 141 | P423 F3 | 0 | 0.0 | 0 | 0 | 0 | 7 | 0 | 93 | 0 | FN1-3365-1 |
| 479 | 3368 | 141 | P423 H10 | 0 | 0.0 | 0 | 0 | 0 | 0 | 0 | 100 | 0 | FN1-3368-1 |
| 480 | 3376 | 142 | P424 H9 | 0 | 0.0 | 0 | 0 | 0 | 2 | 0 | 98 | 0 | FN1-3376-1 |
| 481 | 3376 | 142 | P424 H11 | 0 | 0.0 | 0 | 0 | 0 | 2 | 0 | 98 | 0 | FN1-3376-2 |
| 482 | 3383 | 142 | P425 G9 | 0 | 0.0 | 0 | 0 | 0 | 0 | 0 | 100 | 0 | FN1-3383-1 |
| 483 | 3386 | 142 | P426 B9 | 0 | 0.0 | 0 | 0 | 0 | 2 | 0 | 98 | 0 | FN1-3386-1 |
| 484 | 3387 | 142 | P426 C5 | 0 | 0.0 | 0 | 0 | 1 | 1 | 0 | 98 | 0 | FN1-3387-1 |
| 485 | 3387 | 142 | P426 C7 | 0 | 0.0 | 0 | 0 | 0 | 0 | 0 | 98 | 2 | FN1-3387-2 |
| 486 | 3388 | 142 | P426 D7 | 0 | 0.0 | 0 | 0 | 0 | 1 | 0 | 97 | 1 | FN1-3388-1 |
| 487 | 3406 | 143 | P428 F12 | 0 | 0.0 | 0 | 0 | 0 | 0 | 0 | 100 | 0 | FN1-3406-1 |
| 488 | 3408 | 143 | P428 H11 | 0 | 1.0 | 0 | 0 | 1 | 1 | 0 | 97 | 0 | FN1-3408-1 |
| 489 | 3413 | 143 | P429 E2 | 0 | 0.0 | 0 | 0 | 2 | 0 | 0 | 98 | 0 | FN1-3413-1 |
| 491 | 3444 | 145 | P433 C12 | 0 | 0.0 | 0 | 0 | 0 | 0 | 0 | 100 | 0 | FN1-3444-1 |
| 493 | 3488 | 146 | P438 F4 | 0 | 0.0 | 0 | 0 | 2 | 0 | 0 | 98 | 0 | FN1-3488-1 |
| 494 | 3492 | 147 | P439 B4 | 0 | 0.0 | 0 | 0 | 4 | 2 | 0 | 93 | 0 | FN1-3492-1 |
| 495 | 3497 | 147 | P439 G3 | 0 | 0.0 | 0 | 0 | 0 | 0 | 0 | 100 | 0 | FN1-3497-1 |
| 496 | 3497 | 147 | P439 G4 | 0 | 0.0 | 0 | 0 | 0 | 0 | 0 | 100 | 0 | FN1-3497-2 |
| 497 | 3497 | 147 | P439 G11 | 0 | 0.0 | 0 | 0 | 0 | 0 | 0 | 100 | 0 | FN1-3497-3 |
| 498 | 3531 | 148 | P443 H1 | 0 | 0.0 | 0 | 0 | 0 | 0 | 0 | 100 | 0 | FN1-3531-1 |
| 500 | 3608 | 151 | P453 C8 | 0 | 1.1 | 0 | 0 | 1 | 0 | 1 | 97 | 0 | FN1-3608-1 |
| 501 | 3612 | 151 | P453 G6 | 0 | 0.0 | 0 | 0 | 0 | 0 | 0 | 100 | 0 | FN1-3612-1 |
| 503 | 3635 | 152 | P456 F1 | 0 | 1.1 | 0 | 0 | 1 | 1 | 0 | 96 | 1 | FN1-3635-1 |
| 504 | 3635 | 152 | P456 F2 | 0 | 0.0 | 0 | 0 | 0 | 0 | 0 | 98 | 0 | FN1-3635-2 |
| 505 | 3635 | 152 | P456 F4 | 0 | 0.7 | 0 | 0 | 0 | 0 | 0 | 95 | 0 | FN1-3635-3 |
| 506 | 3635 | 152 | P456 F9 | 0 | 0.5 | 0 | 0 | 0 | 0 | 0 | 99 | 0 | FN1-3635-4 |

TABLE 3-continued

| | M1 | | | Alkaloid profile (percentage of area under peaks) | | | | | | | | | |
|---|---|---|---|---|---|---|---|---|---|---|---|---|---|
| Seln No. | Seed Line | Tray | Plate/ Position | Morphine | Oripavine | Salutaridine | Codeine | Reticuline | Laudanine | Papaverine | Thebaine | Noscapine | Selection name |
| 507 | 3635 | 152 | P456 F10 | 0 | 0.0 | 0 | 0 | 0 | 0 | 0 | 100 | 0 | FN1-3635-5 |
| 508 | 3635 | 152 | P456 F11 | 0 | 0.2 | 0 | 0 | 0 | 0 | 0 | 99 | 0 | FN1-3635-6 |
| 509 | 3679 | 154 | P461 G5 | 0 | 0.6 | 0 | 0 | 0 | 1 | 0 | 98 | 0 | FN1-3679-1 |
| 510 | 3708 | 155 | P465 D2 | 0 | 0.0 | 0 | 0 | 0 | 0 | 0 | 100 | 0 | FN1-3708-1 |
| 511 | 3710 | 155 | P465 F5 | 0 | 0.0 | 0 | 0 | 0 | 0 | 0 | 100 | 0 | FN1-3710-1 |
| 512 | 3718 | 156 | P466 F5 | 0 | 0.0 | 0 | 0 | 0 | 0 | 0 | 100 | 0 | FN1-3718-1 |
| 513 | 3718 | 156 | P466 F7 | 0 | 1.0 | 0 | 0 | 0 | 0 | 0 | 98 | 1 | FN1-3718-2 |
| 514 | 3770 | 158 | P473 B8 | 0 | 1.6 | 0 | 0 | 1 | 0 | 0 | 97 | 0 | FN1-3770-1 |
| 516 | 3794 | 159 | P476 A7 | 0 | 0.4 | 0 | 0 | 0 | 0 | 0 | 100 | 0 | FN1-3794-1 |
| 517 | 3799 | 159 | P476 F4 | 0 | 0.9 | 0 | 0 | 1 | 0 | 0 | 97 | 1 | FN1-3799-1 |
| 518 | 3803 | 159 | P477 B9 | 0 | 0.9 | 0 | 0 | 1 | 0 | 0 | 98 | 1 | FN1-3803-1 |
| 519 | 3804 | 159 | P477 C6 | 0 | 1.0 | 0 | 0 | 1 | 0 | 0 | 96 | 1 | FN1-3804-1 |
| 520 | 3805 | 159 | P477 D12 | 0 | 1.0 | 0 | 0 | 1 | 0 | 0 | 98 | 1 | FN1-3805-1 |
| 521 | 3817 | 160 | P478 H11 | 0 | 0.0 | 0 | 0 | 0 | 0 | 0 | 100 | 0 | FN1-3817-1 |
| 522 | 3821 | 160 | P479 D1 | 0 | 1.1 | 0 | 0 | 1 | 0 | 0 | 98 | 0 | FN1-3821-1 |
| 523 | 3821 | 160 | P479 D3 | 0 | 1.4 | 0 | 0 | 0 | 0 | 0 | 98 | 1 | FN1-3821-2 |
| 524 | 3821 | 160 | P479 D10 | 0 | 0.0 | 0 | 0 | 0 | 0 | 0 | 100 | 0 | FN1-3821-3 |
| 525 | 3827 | 160 | P480 B6 | 0 | 0.7 | 0 | 0 | 0 | 0 | 0 | 99 | 0 | FN1-3827-1 |
| 526 | 3841 | 161 | P481 H3 | 0 | 0.0 | 0 | 0 | 3 | 0 | 0 | 96 | 1 | FN1-3841-1 |
| 528 | 3978 | 166 | P498 H2 | 0 | 0.0 | 0 | 0 | 0 | 0 | 0 | 100 | 0 | FN1-3978-1 |
| 529 | 3995 | 167 | P501 A5 | 0 | 0.0 | 0 | 0 | 0 | 0 | 0 | 100 | 0 | FN1-3995-1 |
| 531 | 4027 | 169 | P505 A6 | 0 | 0.0 | 0 | 0 | 0 | 0 | 0 | 100 | 0 | FN1-4027-1 |
| 532 | 4027 | 169 | P505 A8 | 0 | 0.6 | 0 | 0 | 0 | 0 | 0 | 99 | 0 | FN1-4027-2 |
| 534 | 4050 | 169 | P507 H3 | 0 | 0.4 | 0 | 0 | 1 | 0 | 0 | 99 | 0 | FN1-4050-1 |
| 535 | 4053 | 170 | P508 C9 | 0 | 0.7 | 0 | 0 | 0 | 0 | 0 | 99 | 0 | FN1-4053-1 |
| 537 | 4093 | 171 | P513 C5 | 0 | 1.0 | 0 | 0 | 2 | 1 | 0 | 94 | 1 | FN1-4093-1 |
| 541 | 4121 | 172 | P516 G9 | 0 | 1.2 | 0 | 0 | 0 | 0 | 0 | 97 | 1 | FN1-4121-1 |
| 542 | 4124 | 173 | P517 B2 | 0 | 0.7 | 0 | 0 | 1 | 1 | 0 | 97 | 1 | FN1-4124-1 |
| 543 | 4128 | 173 | P517 F6 | 1 | 1.3 | 0 | 0 | 1 | 0 | 0 | 94 | 0 | FN1-4128-1 |
| 546 | 4144 | 173 | P519 F12 | 0 | 0.9 | 0 | 0 | 0 | 0 | 0 | 97 | 0 | FN1-4144-1 |
| 547 | 4145 | 173 | P519 G7 | 0 | 0.7 | 0 | 0 | 0 | 0 | 0 | 99 | 0 | FN1-4145-1 |
| 548 | 4145 | 173 | P519 G11 | 0 | 0.5 | 0 | 0 | 0 | 0 | 0 | 97 | 0 | FN1-4145-2 |
| 549 | 4148 | 174 | P520 B7 | 0 | 0.7 | 0 | 0 | 1 | 1 | 0 | 98 | 0 | FN1-4148-1 |

Testing of Poppy Straw Alkaloid Content in M2 Generation

Capsules were harvested from the greenhouse as they matured. Seed was removed and weighed into seed envelopes. The poppy straw was placed into 50 mL BD Falcon™ tubes (BD Biosciences, San Jose, Calif.) without grinding and dried either on the lab bench for several days at room temperature or in the laboratory oven at 50° C. for 3 hours. Where capsules were large, only a portion of the capsule was used for analysis, the rest being discarded.

For analysis, the poppy straw was weighed, and either 5 mL or 10 mL acid extractant (5% ethanol ("EtOH"), 0.17% phosphoric acid) added, depending on whether the straw samples weighed less or more than 0.2 g respectively. The samples were agitated with a Ratek orbital shaker (Ratek Instruments, Boronia, Victoria, Australia) for 3 hours. The liquid phase was then filtered using Pall AcroPrep™ 96 filter plates (PN S5045), and the filtrate was analysed for alkaloids using a Waters Acquity UPLC® system (Waters Corporation, Milford, Mass.). The UPLC method used was the same 2.5 minute method as used for leaf samples. Additional extractant was transferred to 1.2 mL wells in 96 well plates, sealed and frozen in case further analysis was required.

The alkaloid contents and profiles were calculated from the UPLC results and weight data. Where the weight was <0.1 g, the weight was deemed as 0.1 g.

The seeds were allowed to dry on the laboratory bench, catalogued and stored.

Of the 549 M2 plants originally selected, 434 survived to produce at least one capsule for harvest (79%). A further 6 mislabeled capsules were harvested, so their M1 parents were not known. 395 plants produced some seed, although 58 had <0.06 g seed, and only 171 plants produced more than 1 g seed.

Due to the potential lack of accuracy with the alkaloid content data (due to low capsule weights and large particle sizes), this data was analysed further only after conversion to alkaloid profiles: i.e. the alkaloid contents in comparison with the total alkaloid content.

Where multiple capsules were harvested from one plant, the mean was determined using Minitab 14 statistical software (Minitab Inc., State College, Pa.).

Table 4, below, shows the results for 133 M2 selections from 92 independent M1 plants that were high in thebaine (>90% of alkaloids) and low in oripavine (<10%). Thirty six M2 selections from 27 independent M1 plants had more than 95% of the alkaloid in the straw as thebaine. Twenty one selections from 16 independent M1 plants had more than 96% of the alkaloid in the straw as thebaine. Eight selections from 6 independent M1 plants had more than 97% of the alkaloid in the straw as thebaine. One selection, FN1-900-5, was identified that had more than 98% of its alkaloid present as thebaine. It can be seen that the oripavine content in the straw of these plants was very low, with several selections having less than 1% of the alkaloid combination, and some with less than 0.5% of the alkaloid combination. All "thebaine-only" plants however contained a small proportion of oripavine in their poppy straw.

TABLE 4

Alkaloid profiles (based on alkaloid concentrations in poppy straw) of M2 plants selected for high thebaine and low oripavine. Means are shown where the number of capsules (caps) was more than one.

| Seln no. | Seln name | Caps | Morphine | Oripavine | Codeine | Salutaridine | Reticuline | Laudanine | Papaverine | Thebaine | Noscapine |
|---|---|---|---|---|---|---|---|---|---|---|---|
| 68 | FN1-291-1 | 15 | 0.4 | 4.7 | 0 | 0.2 | 0.9 | 0.1 | 0.2 | 93.3 | 0.2 |
| 106 | FN1-557-1 | 1 | 0 | 2.8 | 0 | 0.3 | 6.2 | 0 | 0 | 90.7 | 0 |
| 110 | FN1-601-1 | 1 | 0.1 | 0.4 | 0 | 0 | 1.5 | 0.2 | 0 | 97.6 | 0.1 |
| 139 | FN1-809-1 | 5 | 0 | 1.6 | 0.1 | 0.6 | 4.9 | 0 | 0 | 92.7 | 0 |
| 140 | FN1-809-2 | 2 | 0 | 1.7 | 0.1 | 0.3 | 2.1 | 0 | 0 | 95.6 | 0.2 |
| 144 | FN1-846-1 | 1 | 0 | 0.1 | 0 | 0 | 2.5 | 0.1 | 0 | 97.2 | 0 |
| 145 | FN1-846-2 | 3 | 2.6 | 0.4 | 0 | 0 | 3.1 | 0.2 | 0 | 93.5 | 0.1 |
| 149 | FN1-875-1 | 3 | 1.8 | 3.6 | 0 | 0.1 | 1.9 | 0.1 | 0 | 92.4 | 0.1 |
| 153 | FN1-900-1 | 3 | 0 | 0.6 | 0 | 0.1 | 1.5 | 0.2 | 0 | 97.5 | 0.1 |
| 154 | FN1-900-2 | 3 | 0 | 0.6 | 0 | 0.2 | 1.8 | 0.2 | 0 | 97.1 | 0.1 |
| 155 | FN1-900-3 | 3 | 0.8 | 0.5 | 0 | 0 | 2.3 | 0.2 | 0 | 96.1 | 0.1 |
| 156 | FN1-900-4 | 7 | 2.3 | 0.6 | 0 | 0.2 | 1.5 | 0.2 | 0 | 94.9 | 0.3 |
| 157 | FN1-900-5 | 1 | 0 | 0.6 | 0 | 0.2 | 1 | 0.1 | 0 | 98 | 0.1 |
| 161 | FN1-916-1 | 4 | 0.6 | 5.5 | 0 | 0.1 | 1.3 | 0.1 | 0 | 92.3 | 0.1 |
| 167 | FN1-998-1 | 1 | 1.5 | 1.1 | 0.6 | 0 | 2.4 | 0 | 0 | 91.4 | 3.1 |
| 168 | FN1-998-2 | 2 | 0 | 1 | 0.1 | 0.3 | 2.4 | 0 | 0 | 96.3 | 0 |
| 172 | FN1-1027-1 | 1 | 0 | 2.2 | 0 | 0 | 3.1 | 0 | 0 | 94.7 | 0 |
| 173 | FN1-1027-2 | 4 | 0.3 | 2.6 | 0 | 0.3 | 2 | 0.1 | 0 | 94.6 | 0.2 |
| 174 | FN1-1050-1 | 8 | 3.5 | 1 | 0 | 0.4 | 1.3 | 0 | 0 | 93.7 | 0 |
| 175 | FN1-1050-2 | 2 | 0.2 | 3 | 0 | 0.1 | 1.7 | 0 | 0 | 94.8 | 0.2 |
| 180 | FN1-1123-1 | 2 | 0 | 1 | 0 | 0.4 | 3.6 | 0 | 0 | 95.2 | 0 |
| 184 | FN1-1139-2 | 1 | 0 | 5.7 | 0 | 0.1 | 1.3 | 0.2 | 0 | 92.5 | 0.1 |
| 188 | FN1-1153-1 | 10 | 0.1 | 7.9 | 0 | 0 | 1.3 | 0.1 | 0 | 90.6 | 0 |
| 199 | FN1-1185-1 | 3 | 0 | 2.9 | 0 | 0.1 | 2.7 | 0.2 | 0 | 93.9 | 0.2 |
| 208 | FN1-1242-1 | 3 | 1.2 | 0.6 | 0 | 0.1 | 2.8 | 0.2 | 0 | 95 | 0.1 |
| 209 | FN1-1242-2 | 2 | 0 | 0.3 | 0 | 0 | 2.8 | 0.2 | 0 | 96.7 | 0.1 |
| 210 | FN1-1242-3 | 3 | 0 | 0.4 | 0 | 0.1 | 1.7 | 0.1 | 0 | 97.5 | 0.1 |
| 219 | FN1-1326-2 | 4 | 0.5 | 6.9 | 0 | 0.1 | 1.8 | 0.1 | 0 | 90.6 | 0.1 |
| 240 | FN1-1444-1 | 4 | 0 | 5.2 | 0 | 0 | 1.4 | 0.2 | 0 | 93.2 | 0.2 |
| 249 | FN1-1534-1 | 6 | 0.1 | 0.7 | 0 | 0.5 | 2.6 | 0 | 0 | 96.1 | 0 |
| 250 | FN1-1534-2 | 2 | 0.5 | 1.5 | 0 | 0.5 | 4.9 | 0 | 0 | 92.5 | 0.2 |
| 255 | FN1-1571-1 | 2 | 0.4 | 1.5 | 0 | 0.5 | 5.7 | 0 | 0 | 92 | 0 |
| 256 | FN1-1571-2 | 2 | 0.5 | 1.8 | 0 | 0.7 | 4.2 | 0 | 0 | 93 | 0 |
| 257 | FN1-1571-3 | 3 | 0.6 | 1.5 | 0 | 0.5 | 2.5 | 0 | 0 | 94.7 | 0 |
| 258 | FN1-1571-4 | 2 | 0.7 | 1.9 | 0 | 0.4 | 6.9 | 0.1 | 0 | 90.2 | 0 |
| 259 | FN1-1571-5 | 1 | 0 | 1.5 | 0 | 0.7 | 3.4 | 0 | 0 | 94.3 | 0 |
| 260 | FN1-1571-6 | 4 | 0.1 | 1.2 | 0.1 | 0.5 | 4.9 | 0 | 0 | 93.2 | 0 |
| 261 | FN1-1571-7 | 3 | 0 | 1.3 | 0 | 0.3 | 5 | 0 | 0 | 93.3 | 0 |
| 262 | FN1-1571-8 | 1 | 1 | 1.7 | 0 | 0.8 | 2.3 | 0 | 0 | 94 | 0.2 |
| 263 | FN1-1571-9 | 3 | 0.6 | 1.8 | 0 | 0.8 | 4.6 | 0 | 0.1 | 92.1 | 0 |
| 264 | FN1-1571-10 | 4 | 0.2 | 1.4 | 0.1 | 0.4 | 5 | 0 | 0 | 92.9 | 0 |
| 270 | FN1-1625-1 | 1 | 0 | 2.3 | 0 | 0.3 | 1.2 | 0.3 | 0 | 95.7 | 0.1 |
| 273 | FN1-1662-1 | 1 | 0 | 4.6 | 0 | 0.1 | 1.4 | 0 | 0.6 | 93.1 | 0.3 |
| 275 | FN1-1701-1 | 2 | 0 | 2.9 | 0.1 | 0.1 | 2.2 | 0.2 | 0 | 94.6 | 0.1 |
| 279 | FN1-1719-1 | 4 | 0.2 | 0.3 | 0 | 0 | 2.6 | 0.1 | 0 | 96.6 | 0.1 |
| 280 | FN1-1741-1 | 1 | 0 | 3.1 | 0 | 0 | 3.4 | 0.2 | 0 | 93 | 0.3 |
| 284 | FN1-1771-1 | 3 | 0 | 2 | 0 | 0.3 | 1.1 | 0.1 | 0 | 96.6 | 0.1 |
| 285 | FN1-1771-2 | 2 | 0 | 4.8 | 0 | 0.2 | 1.6 | 0 | 0 | 93.4 | 0.1 |
| 292 | FN1-1841-1 | 1 | 0 | 4.7 | 0 | 0 | 1.3 | 0.3 | 0 | 93.7 | 0 |
| 296 | FN1-1869-2 | 1 | 0 | 2.2 | 0 | 0.4 | 1.7 | 0.1 | 0 | 95.5 | 0.1 |
| 299 | FN1-1913-1 | 3 | 0 | 3 | 0 | 0 | 1.8 | 0 | 0 | 95.1 | 0 |
| 307 | FN1-2085-1 | 1 | 0 | 4 | 0 | 0 | 2.8 | 0.1 | 0 | 93 | 0.1 |
| 309 | FN1-2103-1 | 5 | 0.1 | 6.8 | 0 | 0.1 | 2.1 | 0.2 | 0 | 90.7 | 0 |
| 312 | FN1-2152-1 | 3 | 0 | 2.1 | 0 | 0.1 | 5.6 | 0 | 0 | 92.3 | 0 |
| 313 | FN1-2152-2 | 2 | 0 | 0.9 | 0.2 | 0.6 | 3.6 | 0.1 | 0 | 94.8 | 0 |
| 314 | FN1-2152-3 | 3 | 0 | 1.1 | 0 | 0.7 | 3.4 | 0 | 0.1 | 94.7 | 0 |
| 315 | FN1-2152-4 | 2 | 0 | 1.2 | 0 | 0.5 | 3.3 | 0 | 0 | 95 | 0 |
| 318 | FN1-2172-1 | 1 | 0 | 4 | 0 | 0 | 4.9 | 0.2 | 0 | 90.8 | 0.1 |
| 319 | FN1-2175-1 | 1 | 0 | 8 | 0 | 0 | 1.2 | 0.1 | 0 | 90.4 | 0.3 |
| 321 | FN1-2186-1 | 2 | 0 | 3.5 | 0.1 | 0.4 | 1.6 | 0 | 0.3 | 94.1 | 0.1 |
| 325 | FN1-2199-1 | 3 | 0 | 0.4 | 0 | 0.1 | 4.3 | 0.2 | 0 | 95 | 0 |
| 326 | FN1-2199-2 | 2 | 0 | 0.3 | 0 | 0.1 | 3.6 | 0.1 | 0 | 95.9 | 0.2 |
| 339 | FN1-2233-1 | 1 | 0 | 2.8 | 0 | 0.1 | 1.4 | 0 | 0 | 95.7 | 0 |
| 343 | FN1-2245-1 | 2 | 0 | 6.1 | 0 | 0.1 | 1.5 | 0.1 | 0 | 92.1 | 0.2 |
| 364 | FN1-2437-1 | 3 | 0 | 0.5 | 0 | 0.1 | 3.1 | 0.2 | 0 | 96.2 | 0 |
| 367 | FN1-2492-1 | 1 | 0 | 5.5 | 0 | 0.1 | 2.2 | 0.1 | 0 | 92.1 | 0.1 |
| 374 | FN1-2604-1 | 3 | 0 | 0.3 | 0.1 | 0.1 | 5.4 | 0.2 | 0 | 93.7 | 0.2 |
| 377 | FN1-7299-3 | 2 | 0 | 2.4 | 0.1 | 0.2 | 1.3 | 0.1 | 0 | 95.8 | 0.2 |
| 378 | FN1-7299-4 | 2 | 0 | 3.3 | 0.1 | 0.2 | 1.7 | 0.2 | 0 | 94.6 | 0.2 |
| 379 | FN1-7299-5 | 1 | 0 | 2.7 | 0.1 | 0.4 | 1.6 | 0.2 | 0 | 94.7 | 0.3 |
| 380 | FN1-7299-6 | 2 | 0 | 2 | 0 | 0.1 | 1 | 0.1 | 0 | 96.8 | 0.1 |
| 384 | FN1-7306-1 | 1 | 0 | 6.8 | 0 | 0 | 0 | 0 | 0 | 93.1 | 0.1 |
| 396 | FN1-7354-2 | 1 | 0 | 0.6 | 0 | 1.2 | 4.3 | 0 | 0 | 93.9 | 0 |
| 400 | FN1-7378-1 | 1 | 0 | 4.4 | 0 | 0.1 | 1.7 | 0 | 0 | 93.5 | 0.3 |

TABLE 4-continued

Alkaloid profiles (based on alkaloid concentrations in poppy straw) of M2 plants selected for high thebaine and low oripavine. Means are shown where the number of capsules (caps) was more than one.

| Seln no. | Seln name | Caps | Morphine | Oripavine | Codeine | Salutaridine | Reticuline | Laudanine | Papaverine | Thebaine | Noscapine |
|---|---|---|---|---|---|---|---|---|---|---|---|
| 404 | FN1-7397-1 | 1 | 0 | 8 | 0 | 0 | 1 | 0 | 0 | 91 | 0 |
| 407 | FN1-7445-1 | 1 | 0 | 5.6 | 0 | 0 | 2.3 | 0.2 | 0 | 91.9 | 0 |
| 408 | FN1-7447-1 | 1 | 0 | 3.3 | 0 | 0.1 | 3.5 | 0.1 | 0 | 92.8 | 0.2 |
| 409 | FN1-7448-1 | 1 | 0 | 5.2 | 0 | 0.1 | 2.7 | 0.1 | 0 | 91.8 | 0.2 |
| 414 | FN1-7471-1 | 1 | 0 | 3.7 | 0.1 | 0 | 3.2 | 0.2 | 0 | 92.3 | 0.4 |
| 416 | FN1-7491-1 | 1 | 0 | 6.9 | 0 | 0.1 | 1.1 | 0.2 | 0 | 91.8 | 0 |
| 417 | FN1-7499-1 | 1 | 0 | 5.4 | 0 | 0 | 1.6 | 0.2 | 0 | 92.6 | 0.3 |
| 421 | FN1-7525-1 | 2 | 0 | 5.5 | 0 | 0.1 | 1.6 | 0 | 0.4 | 92.5 | 0.1 |
| 422 | FN1-7529-1 | 1 | 0 | 6.7 | 0 | 0.1 | 2.2 | 0 | 0.9 | 90 | 0.2 |
| 426 | FN1-7551-1 | 1 | 0 | 4.6 | 0 | 0.1 | 2.3 | 0.1 | 0 | 92.8 | 0.1 |
| 433 | FN1-7587-1 | 1 | 0 | 8.4 | 0 | 0 | 0.6 | 0.1 | 0 | 90.8 | 0 |
| 434 | FN1-7592-1 | 1 | 0.5 | 2 | 0 | 0.6 | 0.5 | 0 | 0 | 96.3 | 0 |
| 436 | FN1-7598-1 | 1 | 0 | 5.7 | 0 | 0.1 | 2.2 | 0.1 | 0 | 91.7 | 0.2 |
| 437 | FN1-7598-2 | 1 | 0 | 4.5 | 0 | 0 | 1.8 | 0 | 0 | 93.5 | 0.3 |
| 443 | FN1-7656-1 | 1 | 0 | 7.7 | 0 | 0.1 | 1.4 | 0 | 0.5 | 90.2 | 0.2 |
| 445 | FN1-7674-1 | 5 | 0 | 2.4 | 0 | 0 | 2.6 | 0.1 | 0.2 | 94.5 | 0.2 |
| 446 | FN1-7686-1 | 2 | 0 | 1.5 | 0 | 0.4 | 4.9 | 0.1 | 0 | 93.3 | 0 |
| 447 | FN1-7702-1 | 1 | 0 | 3.2 | 0 | 0.1 | 2 | 0 | 0 | 94.6 | 0 |
| 453 | FN1-3141-1 | 1 | 0 | 4.6 | 0 | 0.1 | 2.3 | 0.2 | 0 | 92.7 | 0.1 |
| 454 | FN1-3141-2 | 1 | 0 | 8.1 | 0 | 0 | 1.6 | 0.2 | 0 | 90.1 | 0 |
| 455 | FN1-3158-1 | 2 | 0 | 8 | 0 | 0.1 | 1.6 | 0.2 | 0 | 90.2 | 0.1 |
| 458 | FN1-3209-1 | 1 | 0 | 5 | 0 | 0 | 2 | 0.2 | 0 | 92.5 | 0.2 |
| 461 | FN1-3258-1 | 1 | 0.3 | 6.1 | 0 | 0 | 1.8 | 0.2 | 0 | 91.6 | 0 |
| 463 | FN1-3288-1 | 1 | 0 | 5.8 | 0 | 0.1 | 1.8 | 0.2 | 0 | 92.1 | 0.1 |
| 465 | FN1-3296-1 | 1 | 0 | 8.7 | 0 | 0.1 | 1.1 | 0.1 | 0 | 90.1 | 0 |
| 466 | FN1-3296-2 | 1 | 0 | 2.2 | 0.4 | 0.2 | 1.8 | 0.2 | 0 | 95.2 | 0.1 |
| 474 | FN1-3326-1 | 1 | 0 | 7.2 | 0 | 0.1 | 1.6 | 0.2 | 0 | 90.9 | 0.1 |
| 475 | FN1-3328-1 | 2 | 0 | 0.4 | 0 | 0.2 | 6.5 | 0.3 | 0 | 92.7 | 0 |
| 476 | FN1-3328-2 | 1 | 0 | 0.4 | 0 | 0.1 | 2.9 | 0.2 | 0 | 96.3 | 0.1 |
| 477 | FN1-3306-1 | 2 | 0 | 2.8 | 0.1 | 0.1 | 2.5 | 0.1 | 0 | 94.3 | 0.3 |
| 480 | FN1-3376-1 | 1 | 0 | 5 | 0 | 0 | 1.4 | 0.3 | 0 | 93.3 | 0 |
| 483 | FN1-3386-1 | 1 | 0 | 4.6 | 0.1 | 0.1 | 2.6 | 0 | 1.1 | 91.2 | 0.4 |
| 486 | FN1-3388-1 | 1 | 0 | 5.5 | 0 | 0.1 | 3.1 | 0.2 | 0 | 90.8 | 0.3 |
| 489 | FN1-3413-1 | 1 | 0 | 6.3 | 0 | 0.1 | 2.8 | 0.1 | 0 | 90.6 | 0.2 |
| 495 | FN1-3497-1 | 1 | 0 | 1.4 | 0 | 0 | 4 | 0 | 0 | 94.6 | 0 |
| 496 | FN1-3497-2 | 2 | 0 | 1.2 | 0 | 0.2 | 2.8 | 0 | 0 | 96 | 0 |
| 497 | FN1-3497-3 | 2 | 0 | 1.2 | 0 | 0.2 | 4.7 | 0 | 0 | 94 | 0 |
| 503 | FN1-3635-1 | 2 | 0 | 1.2 | 0 | 0.3 | 4 | 0.1 | 0 | 94.3 | 0.2 |
| 504 | FN1-3635-2 | 1 | 0 | 1.3 | 0 | 0 | 2.8 | 0 | 0 | 95.9 | 0 |
| 506 | FN1-3635-4 | 1 | 0 | 1.2 | 0 | 0.4 | 3.6 | 0 | 0 | 94.8 | 0 |
| 507 | FN1-3635-5 | 1 | 0 | 1 | 0 | 0 | 1.9 | 0 | 0 | 97.1 | 0 |
| 508 | FN1-3635-6 | 1 | 0 | 1.3 | 0 | 0 | 2.2 | 0 | 0 | 96.5 | 0 |
| 509 | FN1-3679-1 | 1 | 0 | 3.2 | 0.2 | 0.1 | 4.6 | 0 | 0 | 91.7 | 0.3 |
| 511 | FN1-3710-1 | 1 | 0 | 8.1 | 0 | 0 | 1.3 | 0.2 | 0 | 90.5 | 0 |
| 512 | FN1-3718-1 | 1 | 0 | 4 | 0 | 0.1 | 1.5 | 0.2 | 0 | 94.2 | 0.1 |
| 516 | FN1-3794-1 | 2 | 0 | 0.1 | 0 | 0.1 | 4 | 0.2 | 0 | 95.7 | 0.1 |
| 521 | FN1-3817-1 | 1 | 0 | 7 | 0 | 0 | 1.5 | 0.1 | 0 | 91.4 | 0 |
| 522 | FN1-3821-1 | 1 | 0.9 | 5.9 | 0 | 0 | 2.5 | 0.2 | 0 | 90.3 | 0.3 |
| 523 | FN1-3821-2 | 1 | 0 | 3.3 | 0 | 0.1 | 3.9 | 0.2 | 0 | 92 | 0.4 |
| 524 | FN1-3821-3 | 1 | 0 | 6.7 | 0 | 0 | 2.3 | 0.1 | 0 | 90.9 | 0 |
| 525 | FN1-3827-1 | 1 | 0 | 4.7 | 0 | 0 | 1 | 0.2 | 0 | 94.1 | 0 |
| 528 | FN1-3978-1 | 1 | 0 | 3 | 0 | 0 | 2.7 | 0.3 | 0 | 94 | 0 |
| 529 | FN1-3995-1 | 2 | 0 | 0.8 | 0 | 0.1 | 3.4 | 0.2 | 0 | 95.5 | 0.2 |
| 534 | FN1-4050-1 | 2 | 0 | 0.1 | 0 | 0.1 | 2.7 | 0.1 | 0 | 97 | 0.1 |
| 535 | FN1-4053-1 | 3 | 0 | 5.1 | 0 | 0 | 1.7 | 0.2 | 0 | 93.1 | 0 |
| 541 | FN1-4121-1 | 1 | 0 | 2.2 | 0 | 0 | 1.6 | 0.3 | 0 | 96 | 0 |
| 542 | FN1-4124-1 | 2 | 0 | 6.9 | 0 | 0 | 1.4 | 0.1 | 0 | 91.8 | 0 |
| 546 | FN1-4144-1 | 1 | 0 | 4 | 0 | 0 | 2.9 | 0.3 | 0 | 92.7 | 0 |
| 548 | FN1-4145-2 | 1 | 0 | 1.9 | 0 | 0.5 | 4.1 | 0 | 0 | 93.5 | 0 |

Growing and Evaluation of M3 Generation

Two of the highest thebaine lines were selected for increase in a greenhouse over winter 2007 to provide data to confirm their alkaloid composition and genetic stability. Thus, the plants grown in this experiment were the M3 generation.

The pots were sown in the greenhouse on 11 Apr. 2007 in double rows, with 120 pots in each double row. Each pot was thinned to 6 plants. Greenhouse conditions were as used previously except that high intensity lights were used to maintain light intensities of approximately 9900 lux for 12 hours per day.

At green capsule stage, latex samples were taken from 24 randomly chosen plants from each line. The samples were obtained from the stigmatic discs using the ray-pluck technique. A stigmatic ray was removed from each plant and dropped into acid extraction solution (5% EtOH, 0.17% $H_3PO_4$) in a filter plate (Pall AcroPrep™ 96 Filter Plate 0.2 μm GHP, NTRL, 350 μL). The rest of the procedure was the same as for leaf latex tests. A separate trial established that there was no significant difference in thebaine or oripavine results attributable to using acid extraction solution instead of latex extraction solution as used previously.

When the capsules were dry the plants were harvested by hand. The harvested capsules were weighed, and then threshed and sieved to separate seed and straw. The straw was sub-sampled and ground to 2 mm.

$$\text{Alkaloid content}(\%) = \frac{0.1 \times \frac{SPLA \times STDC}{STDA} \times \frac{(EV + LOD\% \times SW)}{100} \times \frac{STDI}{SPLI}}{SW \times \frac{(100 - LOD\%)}{100}}$$

where SPLA is the area under the sample peak of interest

STDC is the concentration of the standard alkaloid in mg/mL

STDA is the area under the standard peak

EV is extractant volume in mL

LOD % is the loss on drying of the straw, expressed as a percentage

SW is straw weight extracted in grams.

STDI is the volume of standard injected in microlitres

SPLI is the volume of sample injected in microlitres

FN1-900-1 had noticeably low vigour. The vigour of FN1-1242-3 appeared to be normal. The vigour differences became apparent well after establishment, indicating that it was not a seed quality effect.

Table 5 shows the results of the latex testing at the green capsule stage for the M3 generation. All plants tested had the same alkaloid profile of high thebaine and substantially no oripavine or morphine.

TABLE 5

Results of the green capsule stage testing. The table shows the percentage of area under chromatogram peaks.

| Selection | N | Thebaine Mean | Thebaine SE | Oripavine Mean | Oripavine SE | Morphine Mean | Morphine SE | Codeine Mean | Codeine SE | Papaverine Mean | Papaverine SE | Noscapine Mean | Noscapine SE | Thebaine ratio Mean | Thebaine ratio SE | Norman ratio Mean | Norman ratio SE |
|---|---|---|---|---|---|---|---|---|---|---|---|---|---|---|---|---|---|
| FN1-900-1 | 23 | 98.0 | 0.1 | 0.5 | 0.1 | 0.2 | 0.0 | 0.7 | 0.0 | 0.6 | 0.0 | 0.0 | 0.0 | 99.5 | 0.1 | 99.1 | 0.0 |
| FN1-1242-3 | 24 | 98.6 | 0.0 | 0.2 | 0.0 | 0.1 | 0.0 | 0.6 | 0.0 | 0.5 | 0.0 | 0.0 | 0.0 | 99.8 | 0.0 | 99.3 | 0.0 |

The straw was extracted in duplicate using acid extraction solution (5% EtOH, 0.17% $H_3PO_4$), and analysed using Waters Acquity ULPC® for alkaloid content against standard alkaloid solutions on a dry weight basis. The loss on drying (LOD) of the straw was determined by heating a sample at 88° C. for 9 minutes using an infrared (IR) balance (A&D Company Ltd Model AD4717, Japan).

Peak area data was used to calculate alkaloid concentration in the straw according to the following calculation:

Table 6 shows the loss on drying of straw and the mean alkaloid content of the duplicate straw samples as determined by UPLC.

TABLE 6

Amount of capsule, straw and seed harvested, loss on drying (LOD) of straw, and alkaloid content determined by UPLC.

| Selection | Yield (kg/line) air dry basis Capsule | Yield (kg/line) air dry basis Seed | Yield (kg/line) air dry basis Straw | Straw/Capsule ratio | Straw LOD (%) | Alkaloid content (dry weight basis) Thebaine % (DWB) | Alkaloid content (dry weight basis) Oripavine % (DWB) | Alkaloid content (dry weight basis) Total % | Thebaine ratio |
|---|---|---|---|---|---|---|---|---|---|
| FN1-900-1 | 2.91 | 1.27 | 1.64 | 0.56 | 7.3 | 3.07 | 0.01 | 3.08 | 1.00 |
| FN1-1242-3 | 3.33 | 1.22 | 2.11 | 0.63 | 7.8 | 3.23 | 0.02 | 3.25 | 0.99 |

Thebaine ratio is the thebaine content divided by the sum of thebaine content and oripavine content.

The results show that the poppy straw in the two lines FN1-900-1 and FN1-1242-3 are very high in thebaine content, and very low (0.01% and 0.02%, respectively, in oripavine content). There were no other alkaloids (i.e., morphine, codeine, salutaridine, reticuline, laudanine, papaverine and noscapine) detected using the method described.

Example 2

Latex Extraction

Reagent

Latex Extraction Buffer: 23 g of ammonium dihydrogen phosphate was dissolved in approximately 750 mL deionised water and 200 mL of ethanol added, and made up to 1 L with deionised water.

Method

Isocratic Method:

A Pall AcroPrep™ 96 well, 0.2 µm GHP filter plate was placed on a 96 well, 350 µL collection plate. Both filter and collection plate were labeled and 280 µL of buffer pipetted into each well of the filter plate using a multipipette. Using forceps, a leaf tip approx 5 mm×5 mm was torn off from the plant to be tested and added to the extractant. The latex will bleed into the solution over time.

The sample was allowed to incubate at room temperature for at least 30 minutes. The sample was filtered using a vacuum manifold (Pall Corporation product No. 5017). The collection plate was covered with ABgene® adhesive PCR sealing foil (Cat #: AB-0626) to prevent evaporation. The collection plate can be stored in the refrigerator or freezer pending analysis.

Analysis Method

Instrument:
Waters Acquity UPLC®, with Sample Organiser and Tunable Ultra Violet (TUV) detector
Waters Acquity UPLC Column, Bridged Ethyl Hybrid (BEH) particles,
C18, 1.7 µm, 2.1×50 mm
TUV detector, wavelength 284 nm
Column temperature 50° C.
Reagents:
Mobile Phase A—9% methanol, 0.1% formic acid, adjusted with ammonia to pH=9.6
Mobile phase B—91% methanol, 0.1% formic acid, adjusted with ammonia to pH=9.6
Weak Wash—10% methanol
Strong Wash—100% methanol
The Sample Manager option "Load Ahead" was used to save time between samples. With this option, each sample was aspirated ready for injection while the previous one was running.

TABLE 7

Mobile phase settings

| Time (min) | Flow Rate (mL/min) | % A | % B |
|---|---|---|---|
| 0-0.8 | 0.7 | 35.0 | 65.0 |

The samples were automatically injected (injection volume 2.0 or 3.5 µL) and chromatographed by the Acquity UPLC® along with standard reference alkaloids. After the sample set has been run by the Acquity UPLC®, the peaks were identified by comparison with the standards that were run in the sample set. Typical retention times were as follows:

| Alkaloid | Retention time (minutes) |
|---|---|
| Morphine | 0.24 |
| Oripavine | 0.27 |
| Codeine | 0.31 |
| Papaverine | 0.38 |
| Thebaine | 0.42 |
| Noscapine | 0.68 |

The separations obtained using this method are shown in FIG. 1. Although the peak shapes and separations are not perfect, they are quite adequate for a very rapid screening method.

Empower software (Waters Corporation, Milford, Mass.) was used to identify peaks and calculate peak areas. The data was then exported to an Excel spreadsheet where peak area data was used to determine which poppies had unusual alkaloid profiles.

Figure 2:
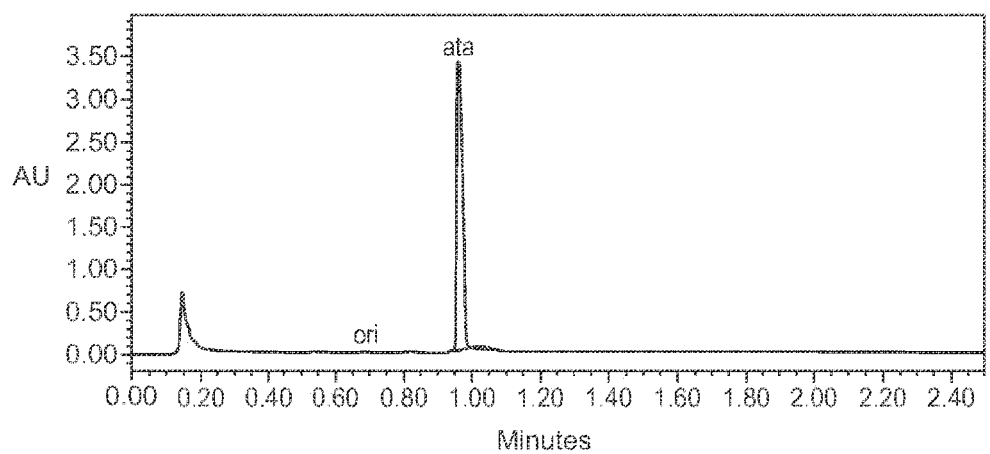
FIG. 2 provides a chromatogram of the poppy straw of the M3 generation of FN1-1242-3. ATA indicates thebaine, ori indicates oripavine peak, AMA represents morphine, and ACA represents codeine.

Gradient Method:

For more accurate repeat analysis of samples, a 2.5 minute gradient UPLC method was used. It is the same as described above, except that the following gradient conditions were used. FIG. 2 provides a chromatogram of the poppy straw of the M3 generation of FN1-1242-3. The injection volume of the sample in FIG. 2 was 2.0 µL. ATA indicates thebaine, ori indicates oripavine peak, AMA represents morphine, and ACA represents codeine.

TABLE 8

Instrument method details for 2.5 min gradient method

| Time (min) | Flow Rate (mL/min) | % A | % B | Curve |
|---|---|---|---|---|
| 0 | 0.8 | 75.0 | 25.0 | |
| 1.4 | 0.8 | 1.0 | 99.0 | 6 |
| 2.5 | 0.8 | 75.0 | 25.0 | 1 |

Example 3

Codeine Plant

Part 1—Undertaking Crosses

Selections of *Papaver somniferum* poppy as described in Example 1, above, that accumulate thebaine as the predominant alkaloid and substantially no oripavine, codeine or morphine were used as the starting material. The selections used included the following:

FN1-900-3, FN1-900-5, FN1-900-7*, FN1-900-11*, FN1-900-12*, FN1-1242-2, FN1-1242-3, and FN1-1242-6*.

The selections marked * were extra M2 plants selected from a further planting of M2 seed, after these lines had been identified as giving rise to thebaine only plants. The complete list of high thebaine selections used is shown in Table 9 below.

The poppy lines listed above were used as male parents in crosses with three poppy lines that produce morphine as their predominant alkaloid. These lines were FW04-0183, PH01-0019 and WF03-1935. Seeds of poppy plants which produce morphine as their predominant alkaloid are widely available.

These plants were grown in pots in a greenhouse, and managed as described for the M3 generation in Example 1. The buds of the female parents were emasculated at early hook stage, ensuring that no pollen was present on the anthers. Kraft paper bags were fastened over the flower buds to prevent contamination with foreign pollen. Pollen was collected from the male parents and applied to the stigmatic discs of the female parents when receptive. The crosses were labeled and the bags were left on for around ten days to exclude other pollen. At maturity the capsules were harvested and then opened and the seed was transferred into paper envelopes. Each individual cross was assigned an X07 number (Table 9).

TABLE 9

This table lists the crosses produced and the parent lines involved.

| Cross | Female Parent | Male Parent |
|---|---|---|
| X07-0001 | WF03-1935 | FN1-1270-1 |
| X07-0002 | WF03-1935 | FN1-2199-1 |
| X07-0003 | WF03-1935 | FN1-1571-6 |
| X07-0004 | WF03-1935 | FN1-1242-3 |
| X07-0005 | WF03-1935 | FN1-1242-2 |
| X07-0006 | WF03-1935 | FN1-1534-2 |
| X07-0007 | WF03-1935 | FN1-900-5 |
| X07-0008 | WF03-1935 | FN1-900-4 |
| X07-0009 | WF03-1935 | FN1-1242-1 |
| X07-0010 | WF03-1935 | FN1-1573-1 |
| X07-0011 | WF03-1935 | FN1-1571-9 |
| X07-0012 | WF03-1935 | FN1-846-2 |
| X07-0013 | WF03-1935 | FN1-1571-2 |
| X07-0014 | WF03-1935 | FN1-1571-4 |
| X07-0015 | WF03-1935 | FN1-1432-1 |
| X07-0016 | WF03-1935 | FN1-1447-1 |
| X07-0017 | WF03-1935 | FN1-1567-1 |
| X07-0018 | WF03-1935 | FN1-1600-1 |
| X07-0019 | WF03-1935 | FN1-1419-1 |
| X07-0020 | WF03-1935 | FN1-1402-1 |
| X07-0021 | WF03-1935 | FN1-1719-1 |
| X07-0022 | WF03-1935 | FN1-1571-1 |
| X07-0023 | WF03-1935 | FN1-2152-2 |
| X07-0024 | WF03-1935 | FN1-2199-2 |
| X07-0025 | WF03-1935 | FN1-1533-1 |
| X07-0026 | WF03-1935 | FN1-2152-3 |
| X07-0027 | WF03-1935 | FN1-1519-1 |
| X07-0028 | WF03-1935 | FN1-7355-1 |
| X07-0029 | WF03-1935 | FN1-1771-2 |
| X07-0030 | WF03-1935 | FN1-7584-1 |
| X07-0031 | WF03-1935 | FN1-2152-4 |
| X07-0032 | WF03-1935 | FN1-2175-1 |
| X07-0033 | WF03-1935 | FN1-7386-1 |
| X07-0034 | WF03-1935 | FN1-7400-1 |
| X07-0105 | FW04-0183 | FN1-900-11* |
| X07-0106 | FW04-0183 | FN1-1571-9 |
| X07-0107 | FW04-0183 | FN1-1571-5 |
| X07-0108 | FW04-0183 | FN1-1270-2* |
| X07-0109 | FW04-0183 | FN1-900-5 |
| X07-0110 | FW04-0183 | FN1-900-3 |
| X07-0111 | FW04-0183 | FN1-900-12* |
| X07-0112 | FW04-0183 | FN1-1571-7 |
| X07-0113 | FW04-0183 | FN1-900-7* |
| X07-0114 | FW04-0183 | FN1-1242-2 |
| X07-0115 | FW04-0183 | FN1-1571-9 |
| X07-0116 | FW04-0183 | FN1-1571-2 |
| X07-0117 | FW04-0183 | FN1-1242-3 |
| X07-0118 | FW04-0183 | FN1-1242-9* |
| X07-0119 | FW04-0183 | FN1-1571-1 |
| X07-0120 | FW04-0183 | FN1-1600-6* |
| X07-0121 | FW04-0183 | FN1-900-7* |
| X07-0122 | PH01-0019 | FN1-1571-2 |
| X07-0123 | PH01-0019 | FN1-1571-10 |
| X07-0124 | PH01-0019 | FN1-1571-10 |
| X07-0125 | PH01-0019 | FN1-1571-7 |
| X07-0126 | PH01-0019 | FN1-900-1 |
| X07-0127 | PH01-0019 | FN1-1242-1 |
| X07-0128 | PH01-0019 | FN1-900-8* |
| X07-0129 | PH01-0019 | FN1-1571-13* |
| X07-0130 | PH01-0019 | FN1-1571-3 |
| X07-0131 | PH01-0019 | FN1-1270-11* |
| X07-0132 | PH01-0019 | FN1-809-5* |
| X07-0133 | FW04-0183 | FN1-1242-6* |
| X07-0134 | FW04-0183 | FN1-1600-10* |

The selections marked * were extra M2 plants selected from a further planting of M2 seed, after these lines had been identified as giving rise to thebaine only plants Part 2. Growing of F1 Generation Two pots (200 mm diameter) of poppies were sown using each of the F1 seed lines listed in Table 9 above. Up to six plants were established in each pot by thinning shortly after emergence. The flowers were self pollinated and the plants were grown to maturity. One plant from each pot was sampled at the green capsule stage by removing a piece of a stigmatic ray and extracting it with acid extractant before filtering and analysing it using the UPLC method as described in Example 5. This showed that all the F1 plants contained morphine, oripavine, codeine and thebaine. (This was expected because the mutations involved are believed to be recessive). Seed was collected from the plants at maturity, the seed from each plant being designated as a separate line.

Part 3. Growing of F2 Generation

Seed collected from the F1 plants (F2 seed), was sown in the greenhouse in fifteen 288-cell Speedling® trays. (Speedling Incorporated, P.O. Box 7238 Sun City Fla. 33586-7238) One row of up to 12 plants was established for each line, and up to 6 lines were grown for every cross. When the plants were at the 6-leaf stage, analysis of the alkaloids present in the leaf latex was conducted to determine the chemotypes of the individual F2 plants.

Latex testing was done according to the method described in Example 6. On the basis of the latex testing, four chemotypes were identified in the populations:

Morphine: morphine present typically with thebaine and codeine

Norman: thebaine and oripavine both present, morphine absent

Thebaine-only: thebaine present, oripavine and morphine absent

Codeine: morphine absent, and codeine present

The occasional plant was identified that had oripavine, codeine and thebaine but little or no morphine. These generally were very small plants whose alkaloid profile changed to fit into one of the four categories as they further developed.

The alkaloid concentrations were calculated from the peak areas by reference to standard alkaloid solutions, and each alkaloid was converted to a percentage of total morphinan alkaloid (morphine, codeine, thebaine and oripavine) in order to determine the chemotype of the plant. A set of rules incorporated in nested "IF" statements was established to determine chemotype. The rules, applied sequentially, were as follows:

If total concentration of morphine, codeine, thebaine and oripavine was less than 5 ug/mL in injected solution, no result.

If Thebaine percentage>95, chemotype=Thebaine-only

If Thebaine+Oripavine percentage>95, chemotype=Norman

If Thebaine+Codeine>95, chemotype=Codeine

If Morphine percentage>2, chemotype=Morphine

Otherwise, chemotype=OCT (oripavine, codeine, thebaine).

Table 10 shows the numbers of plants of each chemotype in the progeny of each cross. Approximately 14% of the plants tested were classified as codeine chemotype. All but three of the 57 crosses tested produced at least one plant classified as codeine chemotype.

TABLE 10

Segregation of the four chemotypes.

| | | Lines | | Chemotype observed | | | |
|---|---|---|---|---|---|---|---|
| Parent | Pedigree | grown | Trays | Codeine | Morphine | Thebaine Only | Norman |
| X07-0105 | FW04-0183 × FN1-900-11 | 6 | 1 | 12 | 39 | 5 | 3 |
| X07-0109 | FW04-0183 × FN1-900-5 | 6 | 1 | 14 | 18 | 15 | 3 |
| X07-0110 | FW04-0183 × FN1-900-3 | 6 | 1 | 11 | 25 | 5 | 3 |
| X07-0111 | FW04-0183 × FN1-900-12 | 6 | 1 | 5 | 22 | 6 | 1 |
| X07-0113 | FW04-0183 × FN1-900-7 | 4 | 2 | 11 | 22 | 9 | 4 |
| X07-0114 | FW04-0183 × FN1-1242-2 | 6 | 2 | 16 | 26 | 12 | 5 |
| X07-0120 | FW04-0183 × FN1-1600-6 | 6 | 2 | 2 | 37 | 5 | 0 |
| X07-0121 | FW04-0183 × FN1-900-7 | 6 | 2 | 12 | 21 | 9 | 2 |
| X07-0129 | PH01-0019 × FN1-1571-13 | 6 | 2-3 | 3 | 37 | 15 | 4 |
| X07-0130 | PH01-0019 × FN1-1571-3 | 6 | 3 | 8 | 30 | 12 | 4 |
| X07-0133 | FW04-0183 × FN1-1242-6 | 6 | 3 | 15 | 36 | 8 | 2 |
| X07-0134 | FW04-0183 × FN1-1600-6 | 6 | 3 | 11 | 36 | 7 | 2 |
| X07-0001 | WF03-1935 × FN1-1270-1 | 6 | 3-4 | 4 | 39 | 7 | 4 |
| X07-0002 | WF03-1935 × FN1-2199-1 | 6 | 4 | 9 | 28 | 11 | 1 |
| X07-0003 | WF03-1935 × FN1-1571-6 | 6 | 4 | 16 | 28 | 7 | 0 |
| X07-0004 | WF03-1935 × FN1-1242-3 | 6 | 4 | 22 | 20 | 9 | 3 |
| X07-0005 | WF03-1935 × FN1-1242-2 | 6 | 4-5 | 18 | 29 | 8 | 8 |
| X07-0006 | WF03-1935 × FN1-1534-2 | 5 | 5 | 3 | 13 | 7 | 3 |
| X07-0009 | WF03-1935 × FN1-1242-1 | 6 | 5 | 10 | 34 | 5 | 5 |
| X07-0010 | WF03-1935 × FN1-1573-1 | 6 | 5 | 0 | 52 | 4 | 4 |
| X07-0011 | WF03-1935 × FN1-1571-9 | 6 | 5-6 | 5 | 34 | 13 | 5 |
| X07-0013 | WF03-1935 × FN1-1571-2 | 6 | 6 | 3 | 39 | 11 | 8 |
| X07-0014 | WF03-1935 × FN1-1571-4 | 6 | 6 | 2 | 36 | 12 | 8 |
| X07-0015 | WF03-1935 × FN1-1432-1 | 6 | 6 | 3 | 38 | 6 | 11 |
| X07-0016 | WF03-1935 × FN1-1447-1 | 6 | 6-7 | 3 | 42 | 5 | 4 |
| X07-0017 | WF03-1935 × FN1-1567-1 | 6 | 7 | 0 | 53 | 0 | 6 |
| X07-0018 | WF03-1935 × FN1-1600-1 | 6 | 7 | 4 | 52 | 6 | 5 |
| X07-0019 | WF03-1935 × FN1-1419-1 | 6 | 7 | 8 | 38 | 4 | 8 |
| X07-0020 | WF03-1935 × FN1-1402-1 | 6 | 7-8 | 2 | 40 | 12 | 5 |
| X07-0021 | WF03-1935 × FN1-1719-1 | 6 | 8 | 16 | 38 | 1 | 0 |
| X07-0022 | WF03-1935 × FN1-1571-1 | 6 | 8 | 4 | 28 | 6 | 5 |
| X07-0024 | WF03-1935 × FN1-2199-2 | 6 | 8 | 20 | 27 | 9 | 3 |
| X07-0025 | WF03-1935 × FN1-1533-1 | 6 | 8-9 | 0 | 38 | 3 | 6 |
| X07-0028 | WF03-1935 × FN1-7355-1 | 6 | 9 | 4 | 52 | 1 | 2 |
| X07-0030 | WF03-1935 × FN1-7584-1 | 6 | 9 | 4 | 55 | 1 | 3 |
| X07-0032 | WF03-1935 × FN1-2175-1 | 6 | 9 | 3 | 57 | 1 | 0 |
| X07-0034 | WF03-1935 × FN1-7400-1 | 6 | 9-10 | 0 | 57 | 1 | 8 |
| X07-0107 | FW04-0183 × FN1-1571-5 | 6 | 10 | 1 | 41 | 19 | 5 |
| X07-0112 | FW04-0183 × FN1-1571-7 | 6 | 10 | 7 | 42 | 10 | 8 |
| X07-0116 | FW04-0183 × FN1-1571-2 | 6 | 10 | 10 | 32 | 19 | 2 |
| X07-0117 | FW04-0183 × FN1-1242-3 | 6 | 10-11 | 11 | 44 | 1 | 8 |
| X07-0119 | FW04-0183 × FN1-1571-1 | 6 | 11 | 3 | 43 | 21 | 5 |
| X07-0123 | PH01-0019 × FN1-1571-10 | 6 | 11 | 9 | 22 | 30 | 3 |
| X07-0124 | PH01-0019 × FN1-1571-10 | 6 | 11 | 9 | 31 | 24 | 4 |
| X07-0125 | PH01-0019 × FN1-1571-7 | 6 | 11-12 | 3 | 40 | 20 | 3 |
| X07-0127 | PH01-0019 × FN1-1242-1 | 6 | 12 | 17 | 33 | 7 | 6 |
| X07-0131 | PH01-0019 × FN1-1270-11 | 6 | 12 | 8 | 38 | 8 | 6 |
| X07-0132 | PH01-0019 × FN1-809-5 | 6 | 12 | 13 | 31 | 8 | 1 |
| X07-0012 | WF03-1935 × FN1-846-2 | 6 | 12-13 | 15 | 38 | 14 | 1 |
| X07-0023 | WF03-1935 × FN1-2152-2 | 6 | 13 | 2 | 39 | 14 | 7 |
| X07-0026 | WF03-1935 × FN1-2152-3 | 6 | 13 | 5 | 29 | 17 | 4 |
| X07-0106 | FW04-0183 × FN1-1571-9 | 6 | 13 | 5 | 38 | 12 | 4 |
| X07-0108 | FW04-0183 × FN1-1270-2 | 6 | 13-14 | 4 | 53 | 4 | 5 |
| X07-0115 | FW04-0183 × FN1-1571-9 | 6 | 14 | 3 | 42 | 14 | 2 |
| X07-0118 | FW04-0183 × FN1-1242-9 | 6 | 14 | 16 | 31 | 7 | 5 |
| X07-0128 | PH01-0019 × FN1-900-8 | 6 | 14 | 15 | 36 | 4 | 5 |
| X07-0027 | WF03-1935 × FN1-1519-1 | 6 | 14-15 | 2 | 49 | 2 | 2 |

After sorting the data for the plants with the highest latex alkaloid contents and highest codeine contents, 69 plants were selected from the 1047 plants analysed in the first 4 trays. Some of these selected plants contained morphine, but were included because their relative codeine content was high. Sixty one of the 69 plants were initially selected on the basis of codeine phenotype. The 69 plants were retested on 30 Oct. 2007 at transplanting into 200 mm pots and grown in Greenhouse 3. They were further leaf sampled on 12 November and 27 November. Another sampling on 12 December used capsule latex instead of leaf tips. Leaf testing and capsule testing used the methods described in Examples 6 and 5, respectively.

Approximately 65 plants having codeine phenotype selected from Trays 5-15 (bottom part of Table 10) were transplanted into soil and grown on to maturity (See Example 4).

Selected Plants

The origins of the 69 plants selected are shown in Table 11A. Table 11B shows the chemotype of each plant as selected by the rules listed above. After the five samplings, there were 51 plants that had consistently tested as codeine phenotype. These came from 11 different crosses involving 10 different thebaine-only parents from 3 different M1 lines (FN1-900, FN1-1242 and FN1-2199).

Several of the 51 selected codeine plants had a higher proportion of codeine than the others (Table 11B). Codeine ratio was defined as:

$$\text{Codeine ratio} = \frac{\text{codeine content}}{\text{codeine content} + \text{thebaine content}}$$

This expresses the content of codeine compared with the total of the predominant alkaloids, thebaine being the only other major alkaloid. It produces the same result irrespective of whether proportions of alkaloid or absolute amounts are used. Plants 10, 39, 50, and 62 had a codeine ratio above 0.98 at the final sampling date, indicating that the thebaine content was very low compared with codeine. Many of the high codeine ratio plants had a high ratio consistently throughout the life of the plant (e.g. plants 10, 26, 29, 37, 50, 59 and 60).

Table 11A—List of plants selected, showing the cross that they have come from (see Table 9).
Table 11B—The classification of chemotype for the 5 latex samplings is shown, as well as the codeine ratio at each sampling date.
Chemotypes: C, codeine; M, morphine; N, Norman, T, thebaine-only, NR, no result.

TABLE 11A

| Plant No. | Tray | Line | Parent |
|---|---|---|---|
| 1 | 1 | PW07-0617 | X07-0105 |
| 2 | 1 | PW07-0617 | X07-0105 |
| 3 | 1 | PW07-0619 | X07-0105 |
| 4 | 1 | PW07-0619 | X07-0105 |
| 5 | 1 | PW07-0620 | X07-0105 |
| 6 | 1 | PW07-0639 | X07-0109 |
| 7 | 1 | PW07-0640 | X07-0109 |
| 8 | 1 | PW07-0641 | X07-0109 |
| 9 | 1 | PW07-0642 | X07-0109 |
| 10 | 1 | PW07-0643 | X07-0109 |
| 11 | 1 | PW07-0643 | X07-0109 |
| 12 | 1 | PW07-0645 | X07-0110 |
| 13 | 1 | PW07-0646 | X07-0110 |
| 14 | 1 | PW07-0646 | X07-0110 |
| 15 | 1 | PW07-0647 | X07-0110 |
| 16 | 1 | PW07-0650 | X07-0110 |
| 17 | 1 | PW07-0650 | X07-0110 |
| 18 | 1 | PW07-0652 | X07-0111 |
| 19 | 1 | PW07-0652 | X07-0111 |
| 20 | 1 | PW07-0653 | X07-0111 |
| 21 | 1 | PW07-0654 | X07-0111 |
| 22 | 2 | PW07-0664 | X07-0113 |
| 23 | 2 | PW07-0664 | X07-0113 |
| 24 | 2 | PW07-0665 | X07-0113 |
| 25 | 2 | PW07-0665 | X07-0113 |
| 26 | 2 | PW07-0665 | X07-0113 |
| 27 | 2 | PW07-0666 | X07-0113 |
| 28 | 2 | PW07-0667 | X07-0114 |
| 29 | 2 | PW07-0667 | X07-0114 |
| 30 | 2 | PW07-0667 | X07-0114 |
| 31 | 2 | PW07-0668 | X07-0114 |
| 32 | 2 | PW07-0670 | X07-0114 |
| 33 | 2 | PW07-0671 | X07-0114 |
| 34 | 2 | PW07-0709 | X07-0121 |
| 35 | 2 | PW07-0710 | X07-0121 |
| 36 | 2 | PW07-0710 | X07-0121 |
| 37 | 2 | PW07-0711 | X07-0121 |
| 38 | 2 | PW07-0713 | X07-0121 |
| 39 | 2 | PW07-0714 | X07-0121 |
| 40 | 2 | PW07-0746 | X07-0129 |
| 41 | 3 | PW07-0755 | X07-0130 |
| 42 | 3 | PW07-0769 | X07-0133 |
| 43 | 3 | PW07-0756 | X07-0133 |
| 44 | 3 | PW07-0770 | X07-0133 |
| 45 | 3 | PW07-0770 | X07-0133 |
| 46 | 3 | PW07-0772 | X07-0133 |
| 47 | 3 | PW07-0773 | X07-0133 |
| 48 | 4 | PW07-0880 | X07-0002 |
| 49 | 4 | PW07-0880 | X07-0002 |
| 50 | 4 | PW07-0883 | X07-0002 |
| 51 | 4 | PW07-0884 | X07-0002 |
| 52 | 4 | PW07-0884 | X07-0002 |
| 53 | 4 | PW07-0886 | X07-0003 |
| 54 | 4 | PW07-0888 | X07-0003 |
| 55 | 4 | PW07-0892 | X07-0004 |
| 56 | 4 | PW07-0892 | X07-0004 |
| 57 | 4 | PW07-0892 | X07-0004 |
| 58 | 4 | PW07-0893 | X07-0004 |
| 59 | 4 | PW07-0893 | X07-0004 |
| 60 | 4 | PW07-0893 | X07-0004 |
| 61 | 4 | PW07-0893 | X07-0004 |
| 62 | 4 | PW07-0894 | X07-0004 |
| 63 | 4 | PW07-0894 | X07-0004 |
| 64 | 4 | PW07-0895 | X07-0004 |
| 65 | 4 | PW07-0896 | X07-0004 |
| 66 | 4 | PW07-0897 | X07-0004 |
| 67 | 4 | PW07-0898 | X07-0005 |
| 68 | 4 | PW07-0898 | X07-0005 |
| 69 | 4 | PW07-0899 | X07-0005 |

TABLE 11B

| Plant No. | Chemotype | | | | | Codeine Ratio (c/ct) | | | | |
|---|---|---|---|---|---|---|---|---|---|---|
| | 22-Oct | 30-Oct | 12-Nov | 27-Nov | 12-Dec | 22-Oct | 30-Oct | 12-Nov | 27-Nov | 12-Dec |
| 1 | C | C | C | M | C | 0.48 | 0.49 | 0.52 | 0.93 | 0.4 |
| 2 | C | C | C | C | C | 0.87 | 0.66 | 0.91 | 0.68 | 0.64 |
| 3 | C | C | C | died | | | | | | |
| 4 | C | C | C | C | C | 0.91 | 0.75 | 0.76 | 0.45 | 0.4 |
| 5 | C | T | N | N | N | | | | | |
| 6 | C | C | C | C | C | 0.69 | 0.76 | 0.74 | 0.54 | 0.62 |
| 7 | C | NR | C | M | M | | | | | |
| 8 | C | C | C | C | C | 0.21 | 0.35 | 0.4 | 0.8 | 0.67 |
| 9 | C | C | C | C | C | 0.67 | 0.57 | 0.7 | 0.84 | 0.71 |
| 10 | C | C | C | C | C | 0.86 | 0.74 | 0.94 | 0.89 | 0.99 |
| 11 | C | C | C | C | C | 0.47 | 0.57 | 0.67 | 0.72 | 0.49 |
| 12 | C | C | C | C | C | 0.96 | 0.6 | 0.97 | 0.87 | 0.88 |
| 13 | C | C | C | C | C | 0.61 | 0.47 | 0.92 | 0.89 | 0.42 |
| 14 | C | C | C | C | M | 0.84 | 0.78 | 0.96 | 0.97 | 0.82 |

TABLE 11B-continued

| Plant | Chemotype | | | | | Codeine Ratio (c/ct) | | | | |
|---|---|---|---|---|---|---|---|---|---|---|
| No. | 22-Oct | 30-Oct | 12-Nov | 27-Nov | 12-Dec | 22-Oct | 30-Oct | 12-Nov | 27-Nov | 12-Dec |
| 15 | C | C | C | C | C | 0.58 | 0.38 | 0.78 | 0.88 | 0.74 |
| 16 | C | C | C | C | C | 0.59 | 0.37 | 0.82 | 0.64 | 0.6 |
| 17 | C | C | C | C | C | 0.62 | 0.45 | 0.79 | 0.92 | 0.49 |
| 18 | M | M | M | M | M | | | | | |
| 19 | C | C | C | C | C | 0.36 | 0.64 | 0.62 | 0.78 | 0.31 |
| 20 | C | C | C | C | C | 0.39 | 0.48 | 0.53 | 0.69 | 0.47 |
| 21 | M | M | M | M | M | | | | | |
| 22 | C | C | C | C | C | 0.46 | 0.58 | 0.52 | 0.91 | 0.6 |
| 23 | C | C | C | C | M | 0.84 | 0.61 | 0.85 | 0.92 | 0.68 |
| 24 | C | C | C | C | C | 0.82 | 0.43 | 0.74 | 0.86 | 0.63 |
| 25 | C | C | C | C | C | 0.54 | 0.4 | 0.55 | 0.75 | 0.77 |
| 26 | C | C | C | C | C | 0.76 | 0.78 | 0.92 | 0.93 | 0.95 |
| 27 | C | C | C | C | C | 0.6 | 0.44 | 0.83 | 0.93 | 0.8 |
| 28 | C | M | M | M | M | | | | | |
| 29 | C | C | C | C | C | 0.97 | 0.9 | 0.96 | 0.96 | 0.94 |
| 30 | C | C | C | C | C | 0.53 | 0.58 | 0.58 | 0.94 | 0.55 |
| 31 | C | C | C | C | C | 0.61 | 0.52 | 0.63 | 0.82 | 0.5 |
| 32 | C | C | C | C | C | 0.54 | 0.62 | 0.53 | 0.92 | 0.49 |
| 33 | C | C | C | C | C | 0.52 | 0.5 | 0.58 | 0.62 | 0.58 |
| 34 | C | C | C | C | C | 0.5 | 0.44 | 0.78 | 0.64 | 0.71 |
| 35 | C | C | C | C | C | 0.38 | 0.27 | 0.65 | 0.83 | 0.71 |
| 36 | C | C | C | C | C | 0.7 | 0.38 | 0.76 | 0.85 | 0.89 |
| 37 | C | C | C | C | C | 0.77 | 0.77 | 0.91 | 0.88 | 0.96 |
| 38 | C | C | C | C | C | 0.41 | 0.39 | 0.56 | 0.8 | 0.63 |
| 39 | C | C | C | C | C | 0.84 | 0.57 | 0.85 | 0.94 | 0.99 |
| 40 | M | M | M | M | M | | | | | |
| 41 | M | M | M | M | M | | | | | |
| 42 | C | C | C | C | C | 0.83 | 0.46 | 0.9 | 0.88 | 0.59 |
| 43 | M | M | M | M | M | | | | | |
| 44 | C | C | C | C | C | 0.73 | 0.31 | 0.68 | 0.76 | 0.83 |
| 45 | C | C | C | C | C | 0.58 | 0.67 | 0.63 | 0.91 | 0.44 |
| 46 | C | C | C | C | C | 0.54 | 0.39 | 0.65 | 0.67 | 0.68 |
| 47 | C | C | C | C | C | 0.66 | 0.37 | 0.78 | 0.89 | 0.48 |
| 48 | C | C | C | C | C | 0.63 | 0.61 | 0.63 | 0.81 | 0.46 |
| 49 | M | C | M | M | M | | | | | |
| 50 | C | C | C | C | C | 0.9 | 0.88 | 0.95 | 0.95 | 0.98 |
| 51 | C | C | C | C | C | 0.43 | 0.72 | 0.71 | 0.55 | 0.58 |
| 52 | C | C | C | C | C | 0.54 | 0.62 | 0.51 | 0.89 | 0.51 |
| 53 | C | C | C | Died | | | | | | |
| 54 | M | M | M | M | M | | | | | |
| 55 | C | C | C | C | M | 0.63 | 0.43 | 0.54 | 0.94 | 0.95 |
| 56 | C | C | C | C | C | 0.62 | 0.65 | 0.81 | 0.96 | 0.95 |
| 57 | C | C | C | C | C | 0.92 | 0.62 | 0.9 | 0.93 | 0.97 |
| 58 | C | C | C | C | C | 0.85 | 0.9 | 0.92 | 0.71 | 0.4 |
| 59 | C | C | C | C | C | 0.81 | 0.7 | 0.88 | 0.9 | 0.96 |
| 60 | C | C | C | C | C | 0.75 | 0.92 | 0.96 | 0.91 | 0.93 |
| 61 | C | Died | | | | | | | | |
| 62 | C | C | C | C | C | 0.74 | 0.6 | 0.67 | 0.53 | 0.99 |
| 63 | C | C | C | C | C | 0.43 | 0.4 | 0.65 | 0.7 | 0.7 |
| 64 | M | M | M | M | M | | | | | |
| 65 | C | C | C | C | C | 0.32 | 0.5 | 0.66 | 0.63 | 0.68 |
| 66 | C | C | C | C | C | 0.43 | 0.43 | 0.54 | 0.65 | 0.85 |
| 67 | C | C | C | C | C | 0.49 | 0.47 | 0.65 | 0.78 | 0.6 |
| 68 | C | C | C | C | C | 0.85 | 0.7 | 0.44 | 0.93 | 0.79 |
| 69 | C | C | C | C | C | 0.38 | 0.47 | 0.67 | 0.75 | 0.83 |

At maturity, all capsules were harvested individually and the seed and poppy straw separated in the laboratory. The straw was dried for 24 hours at 60° C., and then ground in a small electric coffee grinder (Breville Model CG-2, China).

The alkaloids were extracted from the ground straw and analysed according to the procedure described in Example 7. Where there was more than one capsule on a plant, means were calculated (Table 12). When referring to alkaloid ratios throughout this application, "c/total" refers to the ratio of codeine to total alkaloid (morphine+oripavine+codeine+reticuline+thebaine+laudanosine+noscapine+papaverine), "ct/total" refers to the ratio of codeine+thebaine to total alkaloid (morphine+oripavine+codeine+reticuline+thebaine+laudanosine+noscapine+papaverine), "ct/cmot" refers to the ratio of codeine+thebaine to codeine+morphine+oripavine+thebaine, "c/cmot" refers to the ratio of codeine to codeine+morphine+oripavine+thebaine, and "c/ct" refers to the ratio of codeine to codeine+thebaine.

TABLE 12

Alkaloid content of poppy straw (% dry weight basis). Papaverine was not detected in any sample.

| | Alkaloid content in poppy straw (% dry weight basis) | | | | | | | | | Alkaloid ratios. | | | | | |
|---|---|---|---|---|---|---|---|---|---|---|---|---|---|---|---|
| Plant no. | Morphine | Oripavine | Codeine | Reticuline | Laudanine | Thebaine | Laudanosine | Noscapine | Total | c/total | ct/cmot | ct/total | c/ct | c/cmot | Chemotype |
| 1 | 0.02 | 0.00 | 1.85 | 0.03 | 0.02 | 0.80 | 0.01 | 0.00 | 2.73 | 0.68 | 0.99 | 0.97 | 0.70 | 0.69 | c |
| 2 | 0.01 | 0.00 | 3.18 | 0.03 | 0.03 | 0.40 | 0.01 | 0.00 | 3.66 | 0.87 | 1.00 | 0.98 | 0.89 | 0.89 | c |
| 3 | died | | | | | | | | | | | | | | |
| 4 | died | | | | | | | | | | | | | | |
| 5 | 0.00 | 0.54 | 0.02 | 0.03 | 0.03 | 2.52 | 0.02 | 0.00 | 3.16 | 0.01 | 0.83 | 0.81 | 0.01 | 0.01 | n |
| 6 | 0.01 | 0.01 | 2.59 | 0.02 | 0.02 | 0.44 | 0.02 | 0.00 | 3.10 | 0.83 | 1.00 | 0.98 | 0.86 | 0.85 | c |
| 7 | | | | | insufficient straw for analysis | | | | | | | | | | |
| 8 | 0.02 | 0.00 | 1.69 | 0.02 | 0.02 | 0.38 | 0.00 | 0.00 | 2.13 | 0.79 | 0.99 | 0.97 | 0.82 | 0.81 | c |
| 9 | 0.00 | 0.00 | 2.27 | 0.04 | 0.03 | 0.56 | 0.08 | 0.00 | 2.98 | 0.76 | 1.00 | 0.95 | 0.80 | 0.80 | c |
| 10 | 0.01 | 0.00 | 2.87 | 0.03 | 0.03 | 0.02 | 0.01 | 0.00 | 2.97 | 0.97 | 0.99 | 0.97 | 0.99 | 0.99 | c |
| 11 | 0.00 | 0.00 | 1.72 | 0.03 | 0.02 | 0.78 | 0.02 | 0.00 | 2.58 | 0.67 | 1.00 | 0.97 | 0.69 | 0.69 | c |
| 12 | 0.01 | 0.00 | 2.73 | 0.03 | 0.03 | 0.03 | 0.02 | 0.00 | 2.84 | 0.96 | 1.00 | 0.97 | 0.99 | 0.99 | c |
| 13 | 0.00 | 0.00 | 2.03 | 0.05 | 0.04 | 1.30 | 0.05 | 0.00 | 3.48 | 0.58 | 1.00 | 0.96 | 0.61 | 0.61 | c |
| 14 | 0.00 | 0.00 | 1.72 | 0.01 | 0.01 | 0.00 | 0.02 | 0.00 | 1.77 | 0.97 | 1.00 | 0.97 | 1.00 | 1.00 | c |
| 15 | 0.01 | 0.00 | 2.23 | 0.02 | 0.02 | 0.29 | 0.03 | 0.00 | 2.61 | 0.86 | 1.00 | 0.97 | 0.89 | 0.88 | c |
| 16 | 0.01 | 0.00 | 2.04 | 0.03 | 0.03 | 0.76 | 0.02 | 0.00 | 2.89 | 0.71 | 1.00 | 0.97 | 0.73 | 0.73 | c |
| 17 | 0.00 | 0.00 | 2.20 | 0.03 | 0.02 | 1.08 | 0.01 | 0.00 | 3.35 | 0.66 | 1.00 | 0.98 | 0.67 | 0.67 | c |
| 18 | 1.50 | 0.00 | 0.48 | 0.01 | 0.02 | 0.09 | 0.05 | 0.00 | 2.14 | 0.22 | 0.28 | 0.27 | 0.84 | 0.23 | m |
| 19 | 0.02 | 0.01 | 1.38 | 0.02 | 0.02 | 1.77 | 0.05 | 0.00 | 3.26 | 0.42 | 0.99 | 0.97 | 0.44 | 0.43 | c |
| 20 | 0.02 | 0.00 | 1.68 | 0.02 | 0.02 | 1.62 | 0.01 | 0.00 | 3.38 | 0.50 | 1.00 | 0.98 | 0.51 | 0.51 | c |
| 21 | 1.96 | 0.01 | 0.95 | 0.02 | 0.02 | 0.22 | 0.02 | 0.00 | 3.20 | 0.30 | 0.37 | 0.37 | 0.81 | 0.30 | m |
| 22 | 0.02 | 0.00 | 1.84 | 0.01 | 0.02 | 0.94 | 0.01 | 0.00 | 2.83 | 0.65 | 0.99 | 0.98 | 0.66 | 0.66 | c |
| 23 | 0.01 | 0.00 | 3.04 | 0.02 | 0.02 | 0.08 | 0.01 | 0.00 | 3.17 | 0.96 | 1.00 | 0.98 | 0.98 | 0.97 | c |
| 24 | 0.01 | 0.00 | 2.19 | 0.03 | 0.03 | 0.85 | 0.02 | 0.00 | 3.14 | 0.70 | 1.00 | 0.97 | 0.72 | 0.72 | c |
| 25 | 0.00 | 0.00 | 2.11 | 0.05 | 0.04 | 1.76 | 0.02 | 0.00 | 3.98 | 0.53 | 1.00 | 0.97 | 0.54 | 0.54 | c |
| 26 | 0.00 | 0.00 | 3.20 | 0.04 | 0.03 | 0.27 | 0.03 | 0.00 | 3.58 | 0.89 | 1.00 | 0.97 | 0.92 | 0.92 | c |
| 27 | 0.04 | 0.01 | 1.81 | 0.04 | 0.03 | 0.86 | 0.04 | 0.00 | 2.83 | 0.64 | 0.98 | 0.94 | 0.68 | 0.67 | c |
| 28 | 1.33 | 0.07 | 0.51 | 0.02 | 0.02 | 0.84 | 0.01 | 0.00 | 2.80 | 0.18 | 0.49 | 0.48 | 0.38 | 0.18 | m |
| 29 | 0.02 | 0.00 | 2.78 | 0.03 | 0.03 | 0.28 | 0.01 | 0.00 | 3.15 | 0.88 | 0.99 | 0.97 | 0.91 | 0.90 | c |
| 30 | 0.01 | 0.00 | 2.14 | 0.03 | 0.02 | 0.78 | 0.01 | 0.00 | 3.00 | 0.71 | 0.99 | 0.97 | 0.73 | 0.73 | c |
| 31 | 0.00 | 0.01 | 1.87 | 0.06 | 0.05 | 2.21 | 0.03 | 0.00 | 4.23 | 0.44 | 1.00 | 0.97 | 0.45 | 0.45 | c |
| 32 | 0.00 | 0.00 | 1.95 | 0.02 | 0.02 | 0.99 | 0.01 | 0.00 | 3.01 | 0.65 | 1.00 | 0.98 | 0.66 | 0.66 | c |
| 33 | 0.00 | 0.00 | 1.56 | 0.04 | 0.03 | 1.32 | 0.02 | 0.00 | 2.98 | 0.53 | 1.00 | 0.97 | 0.54 | 0.54 | c |
| 34 | 0.01 | 0.00 | 2.30 | 0.02 | 0.03 | 0.75 | 0.04 | 0.00 | 3.15 | 0.73 | 1.00 | 0.97 | 0.76 | 0.75 | c |
| 35 | 0.01 | 0.00 | 1.70 | 0.02 | 0.02 | 0.69 | 0.01 | 0.00 | 2.44 | 0.70 | 1.00 | 0.98 | 0.71 | 0.71 | c |
| 36 | 0.00 | 0.00 | 1.99 | 0.03 | 0.03 | 0.71 | 0.05 | 0.00 | 2.82 | 0.71 | 1.00 | 0.96 | 0.74 | 0.74 | c |
| 37 | 0.01 | 0.00 | 3.00 | 0.02 | 0.04 | 0.08 | 0.08 | 0.00 | 3.23 | 0.93 | 1.00 | 0.95 | 0.98 | 0.97 | c |
| 38 | 0.01 | 0.00 | 1.83 | 0.02 | 0.02 | 0.51 | 0.03 | 0.00 | 2.41 | 0.76 | 1.00 | 0.97 | 0.79 | 0.79 | c |
| 39 | 0.01 | 0.00 | 3.29 | 0.03 | 0.03 | 0.16 | 0.01 | 0.00 | 3.54 | 0.93 | 1.00 | 0.98 | 0.96 | 0.95 | c |
| 40 | 2.54 | 0.07 | 0.26 | 0.02 | 0.03 | 0.56 | 0.17 | 0.00 | 3.65 | 0.07 | 0.24 | 0.23 | 0.32 | 0.08 | m |
| 41 | 2.04 | 0.01 | 0.32 | 0.02 | 0.02 | 0.09 | 0.01 | 0.01 | 2.51 | 0.13 | 0.17 | 0.17 | 0.78 | 0.13 | m |
| 42 | 0.04 | 0.01 | 1.66 | 0.04 | 0.04 | 0.93 | 0.03 | 0.00 | 2.74 | 0.61 | 0.98 | 0.95 | 0.64 | 0.63 | c |
| 43 | 1.70 | 0.01 | 0.40 | 0.01 | 0.02 | 0.09 | 0.00 | 0.00 | 2.23 | 0.18 | 0.22 | 0.22 | 0.82 | 0.18 | m |
| 44 | 0.01 | 0.01 | 2.52 | 0.04 | 0.05 | 1.89 | 0.03 | 0.00 | 4.54 | 0.57 | 1.00 | 0.97 | 0.59 | 0.58 | c |
| 45 | 0.00 | 0.01 | 1.99 | 0.05 | 0.04 | 2.04 | 0.11 | 0.01 | 4.26 | 0.49 | 1.00 | 0.95 | 0.51 | 0.51 | c |
| 46 | 0.00 | 0.01 | 1.82 | 0.02 | 0.02 | 0.88 | 0.00 | 0.00 | 2.74 | 0.67 | 1.00 | 0.99 | 0.67 | 0.67 | c |
| 47 | 0.00 | 0.00 | 1.77 | 0.03 | 0.03 | 1.11 | 0.01 | 0.00 | 2.94 | 0.60 | 1.00 | 0.98 | 0.62 | 0.62 | c |
| 48 | 0.00 | 0.00 | 1.67 | 0.03 | 0.02 | 1.54 | 0.01 | 0.00 | 3.27 | 0.51 | 1.00 | 0.98 | 0.52 | 0.52 | c |
| 49 | 1.75 | 0.00 | 0.56 | 0.01 | 0.02 | 0.02 | 0.01 | 0.00 | 2.36 | 0.24 | 0.25 | 0.24 | 0.97 | 0.24 | m |
| 50 | 0.00 | 0.00 | 3.01 | 0.06 | 0.05 | 1.06 | 0.03 | 0.01 | 4.22 | 0.71 | 1.00 | 0.97 | 0.74 | 0.74 | c |
| 51 | 0.00 | 0.00 | 2.00 | 0.06 | 0.05 | 1.93 | 0.02 | 0.00 | 4.08 | 0.49 | 1.00 | 0.97 | 0.51 | 0.51 | c |
| 52 | 0.01 | 0.01 | 2.31 | 0.05 | 0.04 | 2.02 | 0.04 | 0.01 | 4.49 | 0.52 | 1.00 | 0.97 | 0.53 | 0.53 | c |
| 53 | died | | | | | | | | | | | | | | |
| 54 | 1.77 | 0.14 | 0.43 | 0.03 | 0.03 | 1.04 | 0.03 | 0.00 | 3.48 | 0.13 | 0.44 | 0.42 | 0.30 | 0.13 | m |
| 55 | 0.01 | 0.00 | 1.58 | 0.01 | 0.01 | 0.40 | 0.01 | 0.00 | 2.03 | 0.78 | 0.99 | 0.98 | 0.80 | 0.79 | c |
| 56 | 0.00 | 0.00 | 3.47 | 0.05 | 0.04 | 1.04 | 0.04 | 0.01 | 4.65 | 0.77 | 1.00 | 0.97 | 0.79 | 0.79 | c |
| 57 | 0.00 | 0.00 | 3.20 | 0.03 | 0.03 | 0.49 | 0.01 | 0.00 | 3.76 | 0.85 | 1.00 | 0.98 | 0.87 | 0.87 | c |
| 58 | | | | | insufficient straw for analysis | | | | | | | | | | |
| 59 | 0.00 | 0.00 | 3.86 | 0.03 | 0.05 | 0.67 | 0.03 | 0.00 | 4.65 | 0.83 | 1.00 | 0.97 | 0.85 | 0.85 | c |
| 60 | 0.00 | 0.00 | 2.46 | 0.03 | 0.04 | 0.45 | 0.02 | 0.00 | 3.00 | 0.82 | 1.00 | 0.97 | 0.84 | 0.84 | c |
| 61 | died | | | | | | | | | | | | | | |
| 62 | 0.01 | 0.00 | 2.54 | 0.01 | 0.01 | 0.03 | 0.01 | 0.00 | 2.61 | 0.97 | 1.00 | 0.99 | 0.99 | 0.98 | c |
| 63 | 0.01 | 0.00 | 2.10 | 0.02 | 0.02 | 0.53 | 0.01 | 0.00 | 2.69 | 0.79 | 1.00 | 0.98 | 0.80 | 0.80 | c |
| 64 | 1.64 | 0.01 | 0.72 | 0.02 | 0.03 | 0.17 | 0.02 | 0.00 | 2.61 | 0.28 | 0.35 | 0.34 | 0.81 | 0.28 | m |
| 65 | 0.05 | 0.00 | 2.17 | 0.04 | 0.04 | 1.91 | 0.02 | 0.00 | 4.23 | 0.52 | 0.99 | 0.97 | 0.54 | 0.53 | c |
| 66 | 0.01 | 0.00 | 3.08 | 0.02 | 0.03 | 1.07 | 0.01 | 0.00 | 4.22 | 0.74 | 1.00 | 0.98 | 0.75 | 0.75 | c |
| 67 | 0.01 | 0.01 | 1.80 | 0.05 | 0.04 | 2.24 | 0.03 | 0.00 | 4.17 | 0.44 | 1.00 | 0.97 | 0.45 | 0.45 | c |
| 68 | | | | | insufficient straw for analysis | | | | | | | | | | |
| 69 | 0.00 | 0.00 | 2.52 | 0.03 | 0.03 | 0.90 | 0.01 | 0.00 | 3.50 | 0.72 | 1.00 | 0.98 | 0.74 | 0.74 | c |

Figure 3:
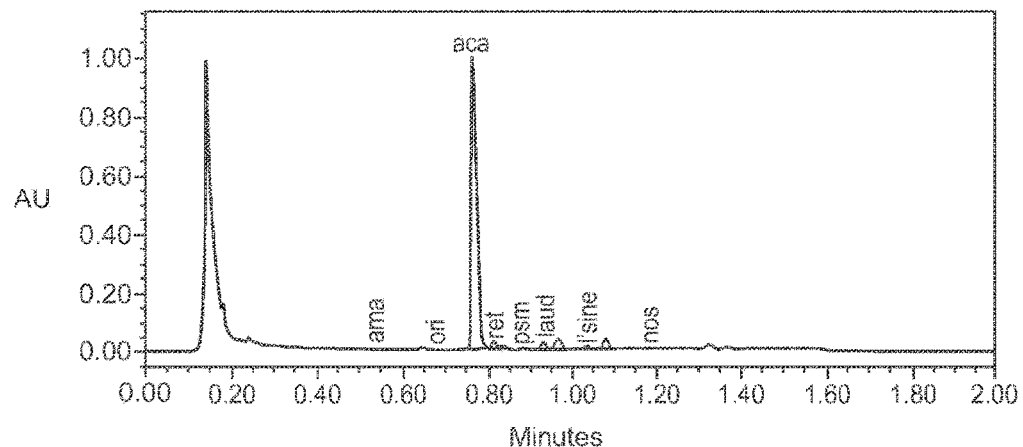
FIG. 3 provides a chromatogram of the poppy straw of plant 10 (PH08-0010 line) of Table 12 displaying a codeine peak at 0.78 minutes.

An example of a chromatogram produced from the plant 10 is shown in FIG. 3. This result is significant as it contains a high concentration of codeine (peaking at 0.78 minutes) and very small amounts of all other alkaloids. If we exclude the plants that died, or produced too little straw to enable testing, of the 54 plants originally selected as codeine phenotype by early stage leaf latex testing, 52 of these (96%) were confirmed by straw analysis. Plant 5 was determined by subsequent testing as being Norman chemotype and Plant 28 was determined as being morphine chemotype.

Our results support the hypothesis that the mutation that determined the thebaine-only phenotype also controlled the step between codeine and morphine. Thus, when the Norman or TOP1 mutation was removed by crossing with plants with a morphine phenotype, plants with the new phenotype segregated. The synthetic pathway used by codeine poppies according to our hypothesis is therefore very simple: Thebaine-Neopinone-Codeinone-Codeine (see Scheme 1).

The range of male and female parents that were used to produce codeine poppies shows that the method is highly reproducible. At least three independent mutation events were involved in producing the thebaine-only male parents, and all three morphine parents successfully gave rise to codeine plants.

Example 4

Field Grown Codeine Plants

Seeds of PW07-0772, PW07-0668, PW07-0650, PW07-0617 and WF03-2024 were sown in a field at Westbury, Tasmania. Table 13, below, shows the origins of these lines.

TABLE 13

Lines sown in field plots at Westbury

| Line | Parent | Pedigree |
| --- | --- | --- |
| PW07-0772 | X07-0133 | FW04-0183 × FN1-1242-6 |
| PW07-0668 | X07-0114 | FW04-0183 × FN1-1242-2 |
| PW07-0650 | X07-0110 | FW04-0183 × FN1-900-3 |
| PW07-0617 | X07-0105 | FW04-0183 × FN1-900-11 |
| WF03-2024 | High morphine control line | |

In this field trial, and in the field experiments described in other examples below, the same general methods of poppy cultivation were used. High analysis fertilizer containing nitrogen, phosphorus and potassium was banded below the seeds. Seeds were sown 5-10 mm below the soil surface. All field trials utilized herbicide sprays to control weeds, fungicide sprays for disease control, and were irrigated as required.

The plants were of the F2 generation, and thus were segregating into the four categories described in Example 3. When the plants reached the 6-8 leaf stage, they were tested according to the method shown in Example 6 to determine alkaloid profile. Plants not having a codeine phenotype were removed, and the remainder of the plants were grown to maturity. Establishment of these plants was poor because of the late stage of the season, and no plants from lines PW07-0668 or PW07-0650 reached maturity.

Also transplanted to the field were approximately 65 plants identified in Example 3 as having a codeine chemotype. These were plants selected from Trays 5-15 (see Table 10). About half of these plants grew to maturity.

Table 14, below, shows the alkaloid content of the poppy straw of the plants grown in the field. The method used to determine alkaloid content is shown in Example 7. Where more than one straw sample from a plant was analysed, the result shown in Table 14 is the mean of the samples analysed.

TABLE 14

Alkaloid content of poppy straw (on a dry weight basis) of selected plants grown in the field.

| | | Alkaloid content in straw % Dry Weight (DW) | | | | | | | | Ratios | | |
| --- | --- | --- | --- | --- | --- | --- | --- | --- | --- | --- | --- | --- |
| Plant ID | Line | Morphine | Oripavine | Codeine | Laudanine | Thebaine | Laudanosine | Reticuline | Salutaridine | Total | c/total | ct/cmot | ct/total |
| FW08-0036 | PW07-0617 | 0.02 | 0.01 | 2.73 | 0.05 | 0.91 | 0.05 | 0.07 | 0.00 | 3.84 | 0.71 | 0.99 | 0.95 |
| FW08-0037 | PW07-0617 | 0.01 | 0.00 | 2.03 | 0.02 | 0.45 | 0.02 | 0.04 | 0.00 | 2.58 | 0.78 | 0.99 | 0.96 |
| FW08-0038 | PW07-0617 | 0.03 | 0.01 | 2.19 | 0.03 | 1.09 | 0.03 | 0.06 | 0.00 | 3.43 | 0.64 | 0.99 | 0.96 |
| FW08-0039* | PW07-0617 | 0.00 | 0.01 | 3.62 | 0.08 | 0.18 | 0.13 | 0.09 | 0.00 | 4.11 | 0.88 | 1.00 | 0.93 |
| FW08-0040 | PW07-0617 | 0.01 | 0.01 | 2.42 | 0.04 | 1.46 | 0.02 | 0.11 | 0.00 | 4.08 | 0.59 | 0.99 | 0.95 |
| FW08-0026 | PW07-0772 | 0.03 | 0.01 | 0.81 | 0.01 | 1.42 | 0.01 | 0.06 | 0.00 | 2.36 | 0.34 | 0.98 | 0.94 |
| FW08-0028 | PW07-0772 | 0.00 | 0.01 | 2.14 | 0.02 | 0.86 | 0.01 | 0.05 | 0.00 | 3.10 | 0.69 | 1.00 | 0.97 |
| FW08-0029 | PW07-0772 | 0.05 | 0.01 | 3.04 | 0.06 | 0.21 | 0.04 | 0.11 | 0.00 | 3.51 | 0.86 | 0.98 | 0.92 |
| FW08-0030 | PW07-0772 | 0.18 | 0.01 | 2.44 | 0.03 | 0.19 | 0.03 | 0.06 | 0.00 | 2.94 | 0.86 | 0.95 | 0.92 |
| FW08-0031 | PW07-0772 | 0.01 | 0.00 | 2.74 | 0.04 | 0.03 | 0.02 | 0.11 | 0.00 | 2.94 | 0.93 | 1.00 | 0.94 |
| FW08-0033 | PW07-0772 | 0.01 | 0.00 | 2.84 | 0.05 | 0.24 | 0.04 | 0.09 | 0.00 | 3.26 | 0.88 | 0.99 | 0.94 |
| FW08-0034 | PW07-0772 | 0.00 | 0.00 | 3.81 | 0.08 | 0.48 | 0.08 | 0.13 | 0.00 | 4.59 | 0.83 | 1.00 | 0.93 |
| FW08-0035 | PW07-0772 | 0.00 | 0.01 | 2.75 | 0.06 | 0.90 | 0.08 | 0.11 | 0.00 | 3.91 | 0.70 | 1.00 | 0.93 |
| FW08-0021 | Transplant | 0.03 | 0.01 | 1.63 | 0.03 | 0.50 | 0.01 | 0.08 | 0.00 | 2.28 | 0.71 | 0.98 | 0.93 |
| FW08-0047 | Transplant | 0.04 | 0.00 | 3.10 | 0.04 | 0.04 | 0.03 | 0.07 | 0.00 | 3.32 | 0.93 | 0.99 | 0.95 |
| FW08-0051 | Transplant | 0.03 | 0.01 | 2.44 | 0.05 | 1.20 | 0.07 | 0.09 | 0.00 | 3.88 | 0.63 | 0.99 | 0.94 |
| FW08-0054 | Transplant | 0.04 | 0.01 | 1.68 | 0.04 | 1.31 | 0.02 | 0.10 | 0.00 | 3.20 | 0.53 | 0.98 | 0.94 |
| FW08-0055 | Transplant | 0.03 | 0.01 | 2.46 | 0.05 | 0.60 | 0.03 | 0.08 | 0.00 | 3.26 | 0.76 | 0.99 | 0.94 |
| FW08-0057 | Transplant | 0.01 | 0.01 | 2.08 | 0.04 | 0.78 | 0.01 | 0.10 | 0.00 | 3.04 | 0.68 | 0.99 | 0.94 |
| FW08-0059 | Transplant | 0.01 | 0.01 | 1.92 | 0.04 | 1.29 | 0.02 | 0.11 | 0.00 | 3.39 | 0.57 | 0.99 | 0.95 |
| FW08-0060 | Transplant | 0.14 | 0.03 | 1.22 | 0.01 | 0.62 | 0.01 | 0.04 | 0.00 | 2.07 | 0.59 | 0.91 | 0.89 |
| FW08-0061 | Transplant | 0.01 | 0.01 | 2.21 | 0.03 | 0.48 | 0.01 | 0.12 | 0.00 | 2.87 | 0.77 | 0.99 | 0.94 |
| FW08-0062 | Transplant | 0.01 | 0.01 | 1.25 | 0.01 | 0.37 | 0.01 | 0.03 | 0.00 | 1.67 | 0.74 | 0.99 | 0.96 |
| FW08-0063 | Transplant | 0.01 | 0.01 | 2.16 | 0.04 | 0.95 | 0.01 | 0.10 | 0.00 | 3.28 | 0.66 | 0.99 | 0.95 |
| FW08-0064 | Transplant | 0.01 | 0.01 | 1.94 | 0.03 | 1.56 | 0.02 | 0.07 | 0.00 | 3.63 | 0.53 | 0.99 | 0.96 |
| FW08-0065 | Transplant | 0.01 | 0.00 | 3.45 | 0.04 | 0.50 | 0.02 | 0.09 | 0.00 | 4.12 | 0.84 | 1.00 | 0.96 |

TABLE 14-continued

Alkaloid content of poppy straw (on a dry weight basis) of selected plants grown in the field.

| Plant ID | Line | Alkaloid content in straw % Dry Weight (DW) | | | | | | | | | Ratios | | |
| --- | --- | --- | --- | --- | --- | --- | --- | --- | --- | --- | --- | --- | --- |
| | | Morphine | Oripavine | Codeine | Laudanine | Thebaine | Laudanosine | Reticuline | Salutaridine | Total | c/total | ct/cmot | ct/total |
| FW08-0067 | Transplant | 0.01 | 0.01 | 2.25 | 0.03 | 0.90 | 0.01 | 0.06 | 0.00 | 3.27 | 0.69 | 1.00 | 0.96 |
| FW08-0068 | Transplant | 0.01 | 0.01 | 1.66 | 0.03 | 0.41 | 0.01 | 0.06 | 0.00 | 2.17 | 0.76 | 0.99 | 0.95 |
| FW08-0072 | Transplant | 0.01 | 0.00 | 3.14 | 0.04 | 0.11 | 0.01 | 0.07 | 0.00 | 3.38 | 0.93 | 0.99 | 0.96 |
| FW08-0073 | Transplant | 0.01 | 0.01 | 1.95 | 0.04 | 0.86 | 0.02 | 0.09 | 0.00 | 2.98 | 0.65 | 0.99 | 0.94 |
| FW08-0075 | Transplant | 0.01 | 0.00 | 3.31 | 0.04 | 0.15 | 0.01 | 0.08 | 0.00 | 3.61 | 0.92 | 1.00 | 0.96 |
| FW08-0076 | Transplant | 0.01 | 0.01 | 1.60 | 0.03 | 1.55 | 0.02 | 0.07 | 0.00 | 3.29 | 0.49 | 0.99 | 0.96 |
| FW08-0077 | Transplant | 0.02 | 0.01 | 1.81 | 0.05 | 0.83 | 0.05 | 0.10 | 0.00 | 2.86 | 0.63 | 0.99 | 0.92 |
| FW08-0078 | Transplant | 0.01 | 0.01 | 1.07 | 0.01 | 1.02 | 0.01 | 0.03 | 0.00 | 2.16 | 0.49 | 0.99 | 0.97 |
| FW08-0079 | Transplant | 0.01 | 0.01 | 1.50 | 0.03 | 0.68 | 0.01 | 0.06 | 0.00 | 2.30 | 0.65 | 0.99 | 0.95 |
| FW08-0080 | Transplant | 0.01 | 0.01 | 2.00 | 0.04 | 1.34 | 0.02 | 0.10 | 0.00 | 3.52 | 0.57 | 0.99 | 0.95 |
| FW08-0081 | Transplant | 0.00 | 0.00 | 2.85 | 0.05 | 0.12 | 0.02 | 0.07 | 0.00 | 3.11 | 0.92 | 1.00 | 0.95 |
| FW08-0082 | Transplant | 0.01 | 0.01 | 0.83 | 0.01 | 0.24 | 0.00 | 0.02 | 0.00 | 1.11 | 0.75 | 0.99 | 0.96 |
| FW08-0083 | Transplant | 0.01 | 0.00 | 1.97 | 0.03 | 0.80 | 0.01 | 0.10 | 0.00 | 2.94 | 0.67 | 1.00 | 0.94 |
| FW08-0084 | Transplant | 0.01 | 0.00 | 0.91 | 0.01 | 0.15 | 0.01 | 0.03 | 0.00 | 1.12 | 0.82 | 0.99 | 0.95 |
| FW08-0085 | Transplant | 0.01 | 0.01 | 2.10 | 0.05 | 0.55 | 0.03 | 0.07 | 0.00 | 2.81 | 0.75 | 0.99 | 0.94 |
| WF03-2024 | control line | 2.56 | 0.03 | 0.17 | 0.05 | 0.13 | 0.05 | 0.04 | 0.01 | 3.03 | 0.06 | 0.11 | 0.10 |

Noscapine and papaverine were not detected in any samples.
Note:
transplants originated from trays 5-15 (see Table 10)
*Straw from plant FW08-0039 was extracted with acid extractant (see Example 7).
Dichloromethane (DCM) was used to extract codeine from the extractant solution at pH 9.3. After washing with deionised water the DCM was allowed to evaporate, and the residue was further dried at 40° C. under vacuum. The residue (sample no. CLN42-106, 32 mg) was submitted for NMR and MS analysis. The results of both analyses were fully consistent with the sample being codeine.

Example 5

Capsule Latex Analysis

Reagent

Acid Extractant: A 1 L measuring cylinder was half filled with deionised water. 1 mL of conc. phosphoric acid and 50 mL ethanol were added and the volume made up to 1 L with deionised water.

Method

Isocratic Method:
A Pall AcroPrep™ 96 well, 0.2 μm GHP filter plate was placed on a 96 well, 350 μL collection plate. Both filter and collection plate were labeled and 280 μL of acid extractant pipetted into each well of the filter plate using a multipipette. A tip of a stigmatic ray was torn off the green capsule of each plant to be tested and added to the extractant. The latex bleeds into the solution over time.

The samples were allowed to incubate at room temperature for at least 30 minutes. The samples were filtered using a vacuum manifold (Pall Corporation product No. 5017). The collection plate was covered with ABgene® adhesive PCR sealing foil (Cat #: AB-0626) to prevent evaporation. The collection plate can be stored in the refrigerator or freezer pending analysis.

Analysis Method

The samples were analyzed using the same instrument, reagents, mobile phase settings and reference standards as described in Example 2 for the isocratic method.

Empower software (Waters Corporation, Milford, Mass.) was used to identify peaks and calculate peak areas. The data was then exported to an Excel spreadsheet where peak area data was used to determine alkaloid profiles.

Example 6

Leaf Latex Analysis

Reagent

Acid Extractant: A 1 L measuring cylinder was half filled with deionised water. 1 mL of conc. phosphoric acid and 50 mL ethanol were added and the volume made up to 1 L with deionised water.

Method

A Pall AcroPrep™ 96 well, 0.2 μm GHP filter plate was placed on a 96 well, 350 μL collection plate. Both filter and collection plate were labeled and 280 μL of acid extractant pipetted into each well of the filter plate using a multipipette. A tip of the youngest fully expanded leaf was torn off each plant to be tested and added to the extractant. The latex bleeds into the solution over time.

The samples were allowed to incubate at room temperature for at least 30 minutes. The samples were filtered using a vacuum manifold (Pall Corporation product No. 5017). The collection plate was covered with ABgene® adhesive PCR sealing foil (Cat #: AB-0626) to prevent evaporation. The collection plate can be stored in the refrigerator or freezer pending analysis.

Analysis Method

The samples were analyzed using the same instrument, reagents and instrument method details (see Table 8) as described for the gradient method in Example 2.

The samples were automatically injected and chromatographed by the Acquity UPLC® along with standard reference alkaloids. After the sample set has been run by the Acquity UPLC®, the peaks were identified by comparison with the standards that were run in the sample set. Empower software (Waters Corporation, Milford, Mass.) was used to identify peaks and calculate peak areas. The data was then exported to an Excel spreadsheet where peak area data was used to determine alkaloid profiles.

Example 7

Poppy Straw Alkaloid Analysis

Reagent

Acid Extractant: A 1 L measuring cylinder was half filled with deionised water. 1 mL of conc. phosphoric acid and 50 mL ethanol were added and the volume made up to 1 L with deionised water.

Method

One gram of ground poppy straw material was weighed into a 50 mL Falcon™ tube (BD Biosciences, San Jose, Calif.), and 20 mL of acid extractant was added. Where straw samples were smaller than 1 g, proportionally less extractant was added. The samples were agitated with a Ratek orbital shaker (Ratek Instruments, Boronia, Victoria, Australia) for 2 hours. The liquid phase was then filtered using Pall AcroPrep™ 96 filter plates (PN S5045), and the filtrate was analysed for alkaloids using a Waters Acquity UPLC® system (Waters Corporation, Milford, Mass.).

The loss on drying (LOD) of the straw was determined after drying straw samples in an oven at 130° C. for 3 hours.

The UPLC method used was the same as used in Example 2, except that the run time was shortened to 2 minutes as shown in Table 15.

TABLE 15

Instrument method details for 2.0 min gradient method

| Time (min) | Flow Rate (mL/min) | % A | % B | Curve |
|---|---|---|---|---|
| 0 | 0.8 | 75.0 | 25.0 | |
| 1.4 | 0.8 | 6.0 | 94.0 | 6 |
| 2.0 | 0.8 | 75.0 | 25.0 | 1 |

Peak area data was used to calculate alkaloid concentration in the straw according to the following calculation:

$$\text{Alkaloid content}(\%) = \frac{0.1 \times \frac{SPLA \times STDC}{STDA} \times \frac{(EV + LOD\% \times SW)}{100} \times \frac{STDI}{SPLI}}{SW \times \frac{(100 - LOD\%)}{100}}$$

where SPLA is the area under the sample peak of interest

STDC is the concentration of the standard alkaloid in mg/mL

STDA is the area under the standard peak

EV is extractant volume in mL

LOD % is the loss on drying of the straw, expressed as a percentage

SW is straw weight extracted in grams.

STDI is the volume of standard injected in microlitres

SPLI is the volume of sample injected in microlitres

Example 8

Poppy Straw Alkaloid Analysis

This method provides more accurate determination of alkaloid content than Example 7. It is recommended for use with samples where there may be other alkaloids eluting close to the peaks of interest and where better separation is required to determine peak identity as accurately as possible.

Reagent

Acetic Acid Extractant (2% acetic acid and 10% ethanol in deionised water); Mix 20 mL of glacial acetic acid and 100 mL of ethanol in a measuring cylinder and make up to 1 L with deionised water.

Method

Ground poppy straw (2+/−0.05 g) was weighed into a 50 mL Falcon tubes. 40 mL of Acetic Acid Extractant was added to each tube, and the tubes were agitated with a Ratek orbital shaker (Ratek Instruments, Boronia, Victoria, Australia) for 1 hour. After shaking, the tubes were allowed to stand for approximately 15 minutes to allow particulates to settle out. The liquid phase was then filtered using Pall AcroPrep™ 96 filter plates (PN S5045), and the collection plate was covered with ABgene® adhesive PCR sealing foil (Cat #: AB-0626) to prevent evaporation.

The loss on drying (LOD) of the straw was determined after drying straw samples in an oven at 130° C. for 3 hours.

Analysis Method

Instrument:
Waters Acquity UPLC®
Waters Acquity UPLC Column, Bridged Ethyl Hybrid (BEH) particles,
C18, 1.7 μm, 1.0×100 mm
TUV detector, wavelength 240 nm
Reagents:
Mobile Phase A—1.32 g/L ammonium formate, adjusted with ammonia to pH=9.6
Mobile phase B—acetonitrile
Weak Wash—10% acetonitrile/water
Strong Wash—0.1% v/v formic acid

TABLE 16

Instrument method details for 20 minute gradient method

| Time (min) | Flow Rate (mL/min) | % A | % B | Curve |
|---|---|---|---|---|
| 0.0 | 0.15 | 90 | 10 | — |
| 12.0 | 0.15 | 68 | 32 | 6 |
| 18.5 | 0.15 | 40 | 60 | 6 |
| 20.0 | 0.15 | 90 | 10 | 1 |

Oven Temperature 60° C.
Injection volume 0.4 μL

The samples were automatically injected and chromatographed by the Acquity UPLC® along with standard reference alkaloids. After the sample set has been run by the Acquity UPLC®, the peaks were identified by comparison with the standards that were run in the sample set. Typical retention times were as follows:

| Alkaloid | Retention time (minutes) |
|---|---|
| Morphine | 3.31 |
| Oripavine | 5.52 |
| Codeine | 6.41 |
| Thebaine | 10.24 |

Empower software (Waters Corporation, Milford, Mass.) was used to identify peaks and calculate peak areas.

Peak area data was used to calculate alkaloid concentration in the straw according to the following calculation:

$$\text{Alkaloid content}(\%) = \frac{0.1 \times \frac{SPLA \times STDC}{STDA} \times \frac{(EV + LOD\% \times SW)}{100}}{SW \times \frac{(100 - LOD\%)}{100}}$$

where SPLA is the area under the sample peak of interest

STDC is the concentration of the standard alkaloid in mg/mL

STDA is the area under the standard peak

EV is extractant volume in mL

LOD % is the loss on drying of the straw, expressed as a percentage

SW is straw weight extracted in grams.

Example 9

Stability of High Codeine Characteristic

Seeds of various lines selected from Example 3 were sown in a greenhouse. When the plants were approximately 6 weeks old, their leaf latex was sampled according to the procedure given in Example 6. Chemotypes were assigned using the rules given in Example 3, part 3 above. Table 17 shows the numbers of chemotypes of each type in the populations tested.

As shown in Table 11, this early stage testing is not completely reliable in predicting the chemotype of the mature plant, so confirmation at straw stage will be required. On the data presented, inheritance of the codeine traits from plants 12, 25, 29, 39 and 56 was completely stable going from the F2 to the F3 generation. In addition, plants 16 and 62 appear to be segregating for the TOP1 mutation which indicates the F2 plant was heterozygous for this mutation, which is to be expected in a proportion of the selections. We tested progeny of plant 16 because this plant had a relatively low codeine ratio, which made us suspect it might be heterozygous for the Norman mutation. Progeny of Plants 5, 10, 26 and 37 were not behaving as expected. We know from prior experience that plants classified as OCT will end up as one of the other chemotypes, so it is quite likely that progeny of plant 37 will all be codeine phenotype. The progeny of the other 3 plants each contained one plant of morphine phenotype. Further work will be required to determine why this has occurred.

Example 10—F3 Generation

Eighteen lines (F3 generation) were grown in a Greenhouse over winter 2008. The selections grown are shown in Table 18 below.

TABLE 18

Selections grown in greenhouse (F3 generation). Lines prefixed with PH08 originated in the greenhouse in summer July 2008 (Example 3), while lines prefixed FW08 originated the field at Westbury, Tasmania (Example 4).

| Selection | Plant No. of Parent in Example 3 | Pedigree | No Pots |
|---|---|---|---|
| FW08-0029 (op)1 | n.a. | FW04-0183 × FN1-1242-6 | 5 |
| FW08-0034 (op) | n.a. | FW04-0183 × FN1-1242-6 | 68 |
| FW08-0039 (op) | n.a. | FW04-0183 × FN1-900-11 | 68 |
| FW08-0040 (op) | n.a. | FW04-0183 × FN1-900-11 | 68 |
| FW08-0047 (op) | n.a. | Unknown | 68 |
| FW08-0065 (op) | n.a. | Unknown | 68 |
| FW08-0069 (op) | n.a. | Unknown | 6 |
| FW08-0072 (op) | n.a. | Unknown | 68 |
| FW08-0075 (op) | n.a. | Unknown | 68 |
| PH08-0002 | 2 | FW04-0183 × FN1-900-11 | 14 |

TABLE 17

Chemotypes observed in young plants of F3 populations.

| Line | Parent Plant (see Table 12) | Chemotype Observed | | | | | Total | Percentage of plants with codeine chemotype | Percentage of plants with either codeine phenotype or thebaine-only phenotype |
|---|---|---|---|---|---|---|---|---|---|
| | | Codeine | Morphine | OCT | T-Only | Norman | | | |
| PH08-0003 | 5 | 2 | 1 | 0 | 0 | 1 | 4 | 50 | 50 |
| PH08-0010 | 10 | 32 | 1 | 0 | 0 | 0 | 33 | 97 | 97 |
| PH08-0012 | 12 | 10 | 0 | 0 | 0 | 0 | 10 | 100 | 100 |
| PH08-0013 | 12 | 9 | 0 | 0 | 0 | 0 | 9 | 100 | 100 |
| PH08-0019 | 16 | 24 | 0 | 0 | 2 | 0 | 26 | 92 | 100 |
| PH08-0030 | 25 | 2 | 0 | 0 | 0 | 0 | 2 | 100 | 100 |
| PH08-0031 | 26 | 24 | 1 | 0 | 0 | 0 | 25 | 96 | 96 |
| PH08-0034 | 29 | 27 | 0 | 0 | 0 | 0 | 27 | 100 | 100 |
| PH08-0043 | 37 | 21 | 0 | 1 | 0 | 0 | 22 | 95 | 95 |
| PH08-0045 | 39 | 14 | 0 | 0 | 0 | 0 | 14 | 100 | 100 |
| PH08-0046 | 39 | 27 | 0 | 0 | 0 | 0 | 27 | 100 | 100 |
| PH08-0065 | 56 | 6 | 0 | 0 | 0 | 0 | 6 | 100 | 100 |
| PH08-0073 | 62 | 31 | 0 | 0 | 1 | 0 | 32 | 97 | 100 |

TABLE 18-continued

Selections grown in greenhouse (F3 generation). Lines prefixed with PH08 originated in the greenhouse in summer July 2008 (Example 3), while lines prefixed FW08 originated the field at Westbury, Tasmania (Example 4).

| Selection | Plant No. of Parent in Example 3 | Pedigree | No Pots |
|---|---|---|---|
| PH08-0010 | 10 | FW04-0183 × FN1-900-5 | 5 |
| PH08-0026 | 23 | FW04-0183 × FN1-900-7 | 68 |
| PH08-0031 | 26 | FW04-0183 × FN1-900-7 | 68 |
| PH08-0043 | 37 | FW04-0183 × FN1-900-7 | 34 |
| PH08-0046 | 39 | FW04-0183 × FN1-900-7 | 68 |
| PH08-0065 | 56 | WF03-1935 × FN1-1242-3 | 68 |
| PH08-0066 | 56 | WF03-1935 × FN1-1242-3 | 4 |
| PH08-0067 | 57 | WF03-1935 × FN1-1242-3 | 68 |

1"op" indicates lines that were open pollinated in previous generation ground to <2 mm using a Retsch SM 2000 cutting mill (Retsch GmbH, Haan, Germany).

Loss on drying (LOD) of the bulked straw from each line was determined after drying straw samples in an oven at 130° C. for 3 hours.

The alkaloids were then extracted from the ground straw and analyzed as described in Example 7.

The alkaloid content of each line is shown in Table 19. The line PH08-0046 contained the highest codeine content with 4.13%. FW08-0039 contained 87.9% codeine as a percentage of the total and contained the lowest content of thebaine of all the lines (0.35%).

These results were compared with the results produced from capsules grown in Greenhouse 3 (Table 12) and in the field during summer 07/08 (Table 14). Paired t-tests were conducted to determine if there was significant differences between the summer and the winter results. It was found that there was not a statistically significant difference (at $P=<0.05$) between the summer and the winter for codeine content of the straw. However, there was a significant difference between the summer and winter for thebaine content, and for the percentage codeine of total alkaloid ($P<0.05$).

TABLE 19

Alkaloid content of poppy straw of selections (F3 generation) grown in greenhouse.

Alkaloid content in poppy straw (% dry weight basis)

| Line | Morphine | Oripavine | Salutaridine | Codeine | Reticuline | Laudanine | Papaverine | Thebaine | Laudanosine | Noscapine | Total | c/total |
|---|---|---|---|---|---|---|---|---|---|---|---|---|
| FW08-0029 | 0.00 | 0.01 | 0.00 | 2.82 | 0.02 | 0.00 | 0.03 | 1.89 | 0.03 | 0.00 | 4.80 | 0.59 |
| FW08-0034 | 0.00 | 0.01 | 0.00 | 3.47 | 0.03 | 0.00 | 0.04 | 1.11 | 0.05 | 0.01 | 4.72 | 0.73 |
| FW08-0039 | 0.00 | 0.01 | 0.00 | 3.56 | 0.03 | 0.00 | 0.04 | 0.35 | 0.06 | 0.00 | 4.05 | 0.88 |
| FW08-0040 | 0.00 | 0.01 | 0.00 | 2.83 | 0.03 | 0.00 | 0.03 | 1.64 | 0.02 | 0.00 | 4.56 | 0.62 |
| FW08-0047 | 0.04 | 0.01 | 0.00 | 3.53 | 0.03 | 0.00 | 0.04 | 0.64 | 0.08 | 0.00 | 4.37 | 0.81 |
| FW08-0065 | 0.30 | 0.01 | 0.00 | 3.35 | 0.02 | 0.00 | 0.03 | 0.69 | 0.02 | 0.00 | 4.41 | 0.76 |
| FW08-0069 | 0.02 | 0.02 | 0.00 | 0.09 | 0.03 | 0.00 | 0.02 | 3.52 | 0.01 | 0.00 | 3.72 | 0.03 |
| FW08-0072 | 0.00 | 0.01 | 0.00 | 3.40 | 0.03 | 0.00 | 0.03 | 1.83 | 0.02 | 0.00 | 5.31 | 0.64 |
| FW08-0075 | 0.02 | 0.01 | 0.00 | 2.20 | 0.02 | 0.00 | 0.02 | 1.52 | 0.03 | 0.00 | 3.82 | 0.57 |
| PH08-0002 | 0.00 | 0.01 | 0.00 | 3.27 | 0.02 | 0.00 | 0.02 | 1.23 | 0.01 | 0.00 | 4.56 | 0.72 |
| PH08-0010 | 0.00 | 0.01 | 0.00 | 3.65 | 0.04 | 0.00 | 0.04 | 2.11 | 0.03 | 0.00 | 5.87 | 0.62 |
| PH08-0026 | 0.00 | 0.01 | 0.00 | 3.65 | 0.03 | 0.00 | 0.04 | 2.09 | 0.02 | 0.00 | 5.83 | 0.63 |
| PH08-0031 | 0.03 | 0.01 | 0.00 | 3.77 | 0.02 | 0.00 | 0.03 | 0.85 | 0.02 | 0.00 | 4.74 | 0.80 |
| PH08-0043 | 0.06 | 0.01 | 0.00 | 3.50 | 0.03 | 0.00 | 0.04 | 0.44 | 0.09 | 0.00 | 4.16 | 0.84 |
| PH08-0046 | 0.03 | 0.01 | 0.00 | 4.13 | 0.03 | 0.00 | 0.03 | 1.24 | 0.01 | 0.00 | 5.48 | 0.75 |
| PH08-0065 | 0.00 | 0.01 | 0.00 | 3.51 | 0.02 | 0.00 | 0.03 | 1.45 | 0.02 | 0.00 | 5.04 | 0.70 |
| PH08-0066 | 0.03 | 0.01 | 0.00 | 3.43 | 0.03 | 0.00 | 0.04 | 1.39 | 0.02 | 0.00 | 4.96 | 0.69 |
| PH08-0067 | 0.00 | 0.01 | 0.00 | 3.87 | 0.03 | 0.00 | 0.04 | 1.25 | 0.02 | 0.00 | 5.21 | 0.74 |

The plants were sown in pots and maintained as described for the M3 generation in Example 1. All plants were tested for alkaloid profile in the latex when they reached the rosette stage (5-8 weeks after sowing). Any pots which contained a plant with a chemotype other than codeine were re-tested and these plants were removed. This was done to remove any plants originating from out-crossed seed. It was found that the PH08 lines were very pure, but the FW08 lines (which were open pollinated in the previous generation) had a number of morphine plants indicating that they had been out-crossed in the field.

When the plants reached flowering stage, they were self pollinated by transferring pollen from the anthers onto the stigmatic disc. At maturity, the capsules were harvested by hand and the seed separated from the straw. The straw was Example 11—Trial Results (F4 Generation)

Five lines were selected from the selections grown in the greenhouse. These were PH08-0026, PH08-0043, PH08-0046, PH08-0065, and PH08-0067. Seed produced in the greenhouse was sown in a replicated field trial at Wesley Vale in Northern Tasmania on 10 Sep. 2008, along with seeds of two control lines. All lines were sown in three blocked replications in plots 5 m long by 1.6 m wide. Standard commercial practices were used to grow the trial as described in Example 4. No growth regulator sprays were used. The trial was harvested on 6 Feb. 2009 by hand picking all the capsules within 2 $m^2$ quadrats within each plot. The samples were threshed and the poppy straw weighed. After grinding to <2 mm, the poppy straw was extracted and analysed using the method described in Example 8. Minitab 14 statistical software (Minitab Inc., State College, Pa.) was used to determine means, standard error (SE) of the mean and analysis of variance.

The yields and alkaloid contents are shown in Tables 20-22.

Table 20 shows that the capsule and straw yields achieved by the high codeine poppy lines were similar to those achieved by a commercial morphine line (WF03-2024) and the Norman parent line WF03-0802. Table 21 shows the alkaloid contents. Two of the lines had over 4% codeine on a dry weight basis in their poppy straw. This is considerably higher than the morphine content of the morphine control line. Table 22 shows that extremely high yields per hectare of codeine can be achieved, of about 60 kg/ha.

TABLE 20

Capsule and straw yields, alkaloid contents and alkaloid yield for field trial grown at Wesley Vale.

|  | Capsule Yield (Tonnes/hectare) | | Straw yield (Tonnes/hectare) | |
| --- | --- | --- | --- | --- |
|  | Mean | SE Mean | Mean | SE Mean |
| PH08-0026 | 4.19 | 0.24 | 1.78 | 0.13 |
| PH08-0043 | 3.18 | 0.40 | 1.41 | 0.15 |
| PH08-0046 | 3.93 | 0.29 | 1.75 | 0.11 |
| PH08-0065 | 3.43 | 0.20 | 1.80 | 0.11 |
| PH08-0067 | 3.76 | 0.14 | 1.84 | 0.06 |
| WF03-0802 | 3.58 | 0.09 | 1.41 | 0.03 |
| WF03-2024 | 4.23 | 0.09 | 1.57 | 0.01 |

TABLE 21

Alkaloid contents in poppy straw for field trial grown at Wesley Vale.

Alkaloid contents in Poppy Straw (% Dry Weight Basis (DWB))

| Name | Morphine | | Codeine | | Thebaine | | Oripavine | | c/cmot | |
| --- | --- | --- | --- | --- | --- | --- | --- | --- | --- | --- |
|  | Mean | SE Mean | Mean | SE Mean | Mean | SE Mean | Mean | SE Mean | Mean | SE Mean |
| PH08-0026 | 0.08 | 0.01 | 4.06 | 0.14 | 0.42 | 0.05 | 0.00 | 0.00 | 0.89 | 0.01 |
| PH08-0043 | 0.13 | 0.06 | 3.43 | 0.05 | 0.08 | 0.02 | 0.01 | 0.01 | 0.94 | 0.02 |
| PH08-0046 | 0.08 | 0.05 | 4.16 | 0.10 | 0.32 | 0.03 | 0.00 | 0.00 | 0.91 | 0.01 |
| PH08-0065 | 0.03 | 0.01 | 3.53 | 0.03 | 1.16 | 0.09 | 0.01 | 0.01 | 0.75 | 0.02 |
| PH08-0067 | 0.26 | 0.12 | 3.61 | 0.20 | 0.75 | 0.08 | 0.00 | 0.00 | 0.78 | 0.02 |
| WF03-0802 | 0.20 | 0.18 | 0.01 | 0.00 | 2.80 | 0.07 | 1.34 | 0.06 | 0.00 | 0.00 |
| WF03-2024 | 3.14 | 0.07 | 0.03 | 0.00 | 0.09 | 0.03 | 0.04 | 0.01 | 0.01 | 0.00 |

TABLE 22

Alkaloid yield in kilograms alkaloid per hectare for field trial grown at Wesley Vale.

Alkaloid yields (Kg/ha)

|  | Morphine | | Codeine | | Thebaine | | Oripavine | |
| --- | --- | --- | --- | --- | --- | --- | --- | --- |
|  | Mean | SE Mean | Mean | SE Mean | Mean | SE Mean | Mean | SE Mean |
| PH08-0026 | 1.34 | 0.24 | 65.3 | 6.84 | 6.63 | 0.48 | 0.04 | 0.02 |
| PH08-0043 | 1.72 | 0.72 | 44.5 | 5.71 | 1.04 | 0.24 | 0.12 | 0.06 |
| PH08-0046 | 1.33 | 0.77 | 66.4 | 3.73 | 5.17 | 0.41 | 0.06 | 0.02 |
| PH08-0065 | 0.55 | 0.22 | 58.0 | 3.84 | 19.2 | 2.33 | 0.25 | 0.24 |
| PH08-0067 | 4.21 | 1.74 | 60.7 | 5.17 | 12.7 | 1.67 | 0.07 | 0.04 |
| WF03-0802 | 2.63 | 2.31 | 0.09 | 0.003 | 36.5 | 1.22 | 17.5 | 1.06 |
| WF03-2024 | 46.2 | 1.01 | 0.42 | 0.05 | 1.36 | 0.42 | 0.59 | 0.20 |

Example 12. Trial Crop Results (F4 Generation)

Five trial crops were sown using the seed harvested from the greenhouse (see Example 10). These were sown on three properties in North-west Tasmania, as indicated in Table 23. Standard commercial agricultural practices as described above were used at the three sites.

TABLE 23

Details of trial crop sites.

| Grower and location | Line sown | Sowing date | Area sown (ha) |
| --- | --- | --- | --- |
| Sassafras Farms, Sassafras, Tasmania | PH08-0026 | 10 Sep. 2008 | 0.40 |
| N. R. and M House, Forest, Tasmania | PH08-0043 | 10 Sep. 2008 | 0.24 |
|  | PH08-0065 | 10 Sep. 2008 | 0.21 |
|  | PH08-0067 | 10 Sep. 2008 | 0.40 |
| Glen Carr Pty. Ltd., Stowport, Tasmania | PH08-0046 | 1 Oct. 2008 | 0.40 |

When the crops were ready for harvest, an area from near the centre of each plot was hand picked. The capsules were threshed to separate poppy straw from seed. A subsample of the straw was then ground to <2 mm using a Retsch SM 2000 cutting mill, and analysed in duplicate using the method described in Example 8.

The results are shown in Table 24.

TABLE 24

Straw and seed weights hand-harvested and alkaloid content in the poppy straw grown in trial crops.

| Line sown | Poppy straw wt (Kg) | Seed weight (Kg) | Mean Alkaloid content (% DWB) | | | | c/cmot |
|---|---|---|---|---|---|---|---|
| | | | Morphine | Codeine | Oripavine | Thebaine | |
| PH08-0026 | 9.7 | 14.6 | 0.00 | 3.97 | 0.00 | 0.39 | 0.910 |
| PH08-0043 | 8.6 | 11.4 | 0.01 | 3.14 | 0.00 | 0.06 | 0.978 |
| PH08-0046 | 10.0 | 12.5 | 0.00 | 4.19 | 0.00 | 0.21 | 0.952 |
| PH08-0065 | 8.5 | 7.7 | 0.00 | 2.98 | 0.00 | 0.98 | 0.752 |
| PH08-0067 | 8.1 | 9.5 | 0.00 | 3.01 | 0.00 | 0.38 | 0.888 |

The high contents of codeine and low contents of morphine indicate that there has been stable inheritance of the high codeine characteristic from the F2 plants into these F4 plants. The higher morphine contents observed in Example 11 (Table 21) are consistent with there being a small number of morphine type volunteer plants growing at the trial site. The trial crop locations used in Example 12 were carefully chosen as paddocks that either had never grown poppies, or had grown poppies many years earlier and were free of volunteer poppy plants.

Example 13

Preparation of CPS Codeine Sample and Confirmation of Identity of Codeine Using LCMS:

To 250 g codeine poppy straw (machine harvested PH08-0026, load 0895, 2009 field-grown) was added 43% v/v ethanol in water (1500 mL). Agitation was applied and calcium hydroxide (15 g) added. The mixture was agitated at room temperature for 1 hour, then filtered under vacuum through a Whatman #52 filter. Residual solvent in the damp straw was extracted using a hydraulic press (Labox). No attempt was made to quantitatively extract alkaloid, with only one pass and no rinsing of the pressed straw "cake". To the combined filtrate (miscella, 1 L) was added conc. phosphoric acid until pH 5.1 was obtained. After overnight standing, a slight residue had formed and was filtered off before concentrating the miscella to a volume of 250 mL using the rotary evaporator (80° C.). The concentrated miscella was analysed by UPLC (using the analysis method described in Example 8) and found to contain codeine: 5.65 g (2.26% w/w); thebaine: 0.86 g (0.34%); an unknown with relative retention time (RRT) to codeine of 2.41 (tentatively identified as a codeinone-thebaine dimer MW 606): 2.34% relative to codeine by peak area.

The concentrated miscella was partitioned 3 times using 0.20 vol (50 mL) toluene each time, at 20° C. and pH 6.5 (adjusted using 40% potassium hydroxide). After partitioning, UPLC analysis gave codeine 5.29 g (2.12% w/w); thebaine 0.28 g (0.11% w/w); RRT 2.41: <0.01% relative to codeine.

The alkaloids were extracted 3 times into toluene at 50° C. and pH 12.6 (2×0.22 vol., 1×0.10 vol.) and the toluene back-extracted with water at 20° C. and pH 6.5 (2×0.22 vol.). UPLC analysis of the pH 6.5 back-extracts gave:
  Extract #1. Codeine: 3.86 g; Thebaine: 0.033 g
  Extract #2. Codeine: 0.48 g; Thebaine: 0.006 g The back-extracts were combined and adjusted slowly to pH 11 at 50° C. using 20% sodium hydroxide. Codeine came out of solution as an oil. The mixture was cooled slowly and agitated overnight, during which the oil converted to a fine, off-white solid.

The solid was isolated with a cold water rinse (10 mL) and dried in vacuo at 40° C. to provide the CPS codeine sample 0905060.

Figure 4:
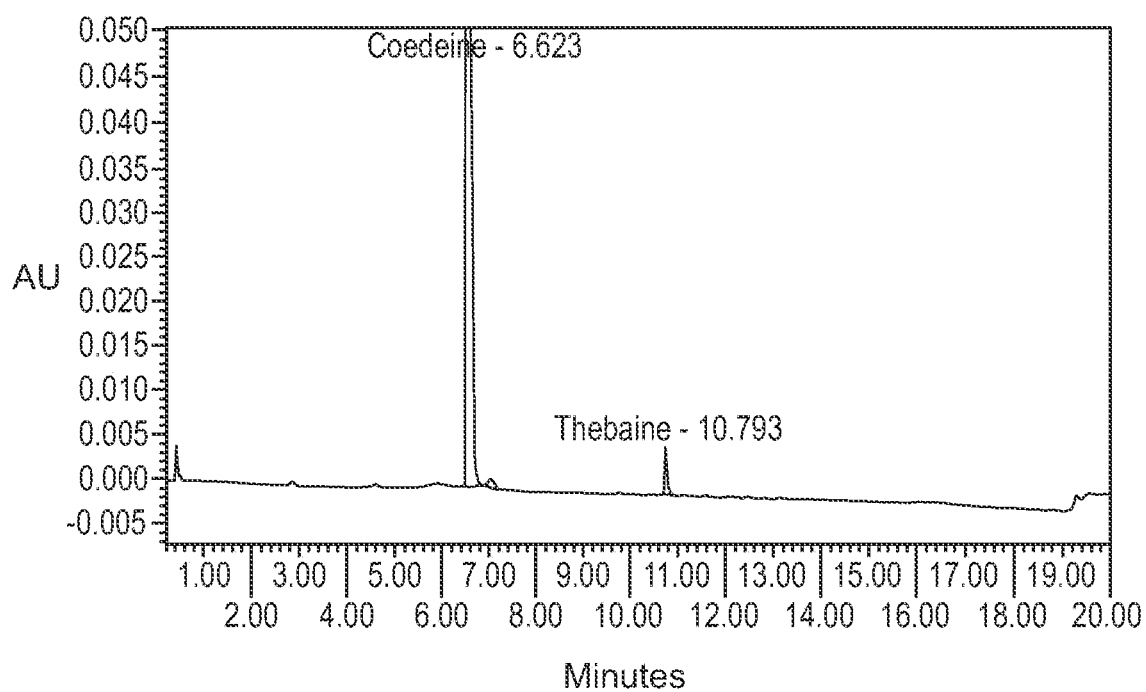
FIG. 4 provides a chromatogram of Concentrate of Poppy Straw—Codeine, prepared from poppy straw from PH08-0026.

Dry mass: 3.51 g. Assay: 97.8% (assumes LOD of 0%); Thebaine: 0.6% rel. to codeine w/w; RRT 2.41: 0.01% by peak area. Overall yield from concentrated miscella: 61%. FIG. 4 shows a chromatogram of the CPS codeine sample after dissolving in 1% formic acid at 1 g/L, utilizing the UPLC Analysis Method described in Example 8.

The CPS codeine sample 0905060 was analysed by LCMS for accurate mass determination, utilizing the UPLC Analysis Method described in Example 8. The instrument used for the MS work was a Waters Micromass Q-ToF Premier API Mass Spectrometer. It was fitted with an electrospray probe, and operated in positive ion mode. The LCMS was operated via MassLynx software version 4.1

A codeine identification standard, 0903343, was used for comparison with the codeine CPS sample. Both the sample and the standard were prepared for analysis by dissolving in 1% formic acid at 1 g/L.

The retention time of the main peak observed in the CPS codeine sample 0905060, matched the retention time of the codeine peak observed in the codeine identification standard, both having a retention time of 6.72 minutes.

A summary of accurate mass data obtained for the CPS codeine sample 0905060, and the codeine identification standard, 0903343, is shown in Table 25. Both the codeine identification standard and the CPS codeine sample figures are within an acceptable ppm error range of the theoretical codeine accurate mass having ppm error values of <10 ppm.

TABLE 25

Accurate Mass Data.

| Sample | Accurate Mass $[M + H^+]$ | Error (ppm) where $[M + H^+] = C18H22NO3$ |
|---|---|---|
| Codeine (Calculated) | 300.1600 | 0 |
| Codeine ID Std 0903343 | 300.1581 | −6.3 |
| CPS Codeine Sample 0905060 | 300.1589 | −3.7 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A poppy straw from a *Papaver somniferum* plant, the poppy straw having a codeine fraction of about 55% by weight or greater of an alkaloid combination, and a codeine content above 0.8% by dry weight of the poppy straw, and wherein the alkaloid combination comprises morphine, codeine, thebaine and oripavine.

2. The poppy straw of claim 1, wherein codeine constitutes about 75% by weight or greater of the alkaloid combination.

3. The poppy straw of claim 1, wherein codeine constitutes about 90% by weight or greater of the alkaloid combination.

4. The poppy straw of claim 1, wherein codeine constitutes about 96% by weight or greater of the alkaloid combination.

5. An alkaloid combination obtained from a poppy straw of a *Papaver somniferum* plant, the poppy straw having a codeine fraction of about 55% by weight or greater of the alkaloid combination, and a codeine content above 0.8% by dry weight of the poppy straw, wherein the alkaloid combination comprises morphine, codeine, thebaine and oripavine.

6. The alkaloid combination of claim 5, wherein the poppy straw comprises 0.8 to 4.2% of codeine by dry weight of the poppy straw.

7. The alkaloid combination of claim 5, wherein codeine constitutes about 75% by weight or greater of the alkaloid combination.

8. The alkaloid combination of claim 5, wherein thebaine constitutes about 25% by weight or less of the alkaloid combination.

9. The alkaloid combination of claim 5, wherein codeine constitutes about 90% by weight or greater of the alkaloid combination.

10. The alkaloid combination of claim 5, wherein thebaine constitutes about 10% by weight or less of the alkaloid combination.

11. The alkaloid combination of claim 5, wherein codeine constitutes about 96% by weight or greater of the alkaloid combination.

12. The alkaloid combination of claim 5, wherein thebaine constitutes about 2% by weight or less of the alkaloid combination.

13. The alkaloid combination of claim 5, wherein there is substantially no morphine and substantially no oripavine in the alkaloid combination.

14. The poppy straw according to claim 1, wherein the codeine content of the alkaloid combination is 0.8% to 4.2% by weight.

15. The poppy straw of claim 1, wherein the codeine content of the poppy straw is above 2% on a dry weight basis of the poppy straw.

16. The poppy straw of claim 15, wherein the codeine content of the poppy straw is above 2.5% by dry weight of the poppy straw.

17. The poppy straw of claim 15, wherein thebaine constitutes about 40% by weight or less of the alkaloid combination.

18. The poppy straw of claim 15, wherein there is substantially no thebaine in the alkaloid combination.

19. The poppy straw of claim 1, wherein there is substantially no morphine and substantially no oripavine in the alkaloid combination.

20. The poppy straw of claim 15, wherein there is substantially no morphine and substantially no oripavine in the alkaloid combination.

21. The poppy straw of claim 15, wherein there is substantially no papaverine in the alkaloid combination.

22. The poppy straw according to claim 1, wherein the *Papaver somniferum* plant is stably reproducing by self-pollination in respect of the codeine fraction and the codeine content of the poppy straw.

23. The poppy straw according to claim 15, wherein the *Papaver somniferum* plant is stably reproducing by self-pollination in respect of the codeine fraction and the codeine content of the poppy straw.

24. A concentrate of poppy straw obtained from a poppy straw of a *Papaver somniferum* plant, the poppy straw having a codeine fraction of about 55% by weight or greater of an alkaloid combination, and a codeine content above 0.8% by dry weight of the poppy straw, and wherein the alkaloid combination comprises morphine, codeine, thebaine and oripavine.

25. The concentrate of poppy straw of claim 24, wherein the codeine content of the poppy straw is above 2.0% by dry weight of the straw.

26. The concentrate of poppy straw of claim 24, wherein there is substantially no morphine and substantially no oripavine in the alkaloid combination.

27. The concentrate of poppy straw of claim 24, wherein there is substantially no thebaine in the alkaloid combination.

28. The concentrate of poppy straw according to claim 24, wherein the *Papaver somniferum* plant is stably reproducing by self-pollination in respect of the codeine fraction and the codeine content of the poppy straw.

29. A method for providing a codeine preparation, comprising;
  providing (1) a poppy straw of a *Papaver somniferum* plant, the poppy straw having a codeine fraction of about 55% by weight or greater of an alkaloid combination, and a codeine content above 0.8% by dry weight of the poppy straw, wherein the alkaloid combination comprises morphine, codeine, thebaine and oripavine, or (2) a concentrate of poppy straw obtained from said poppy straw; and
  extracting codeine from the poppy straw or the concentrate of poppy straw.

30. The method of claim 29, wherein the codeine content of the poppy straw is above 2.0% by dry weight of the poppy straw.

31. The method according to claim 29, wherein there is substantially no morphine and substantially no oripavine in the alkaloid combination.

32. The method of claim 29, wherein there is substantially no thebaine in the alkaloid combination.

33. The method of claim 29, wherein there is substantially no papaverine in the alkaloid combination.

34. The method according to claim 29, wherein the *Papaver somniferum* plant is stably reproducing by self-pollination in respect of the codeine fraction and the codeine content of the poppy straw.

* * * * *